US012797535B2

(12) United States Patent
Luxon et al.

(10) Patent No.: US 12,797,535 B2
(45) Date of Patent: Nov. 17, 2026

(54) DEVICES AND METHODS FOR MANAGING CHEST OR WOUND DRAINAGE

(71) Applicant: Centese, Inc., Omaha, NE (US)

(72) Inventors: Evan S. Luxon, Omaha, NE (US); Ryan Coughlin, Omaha, NE (US); Justin Randy Preston, San Francisco, CA (US); Ryan Behringer, Omaha, NE (US); Kyle Fitch, Omaha, NE (US); Nicholas Want, Omaha, NE (US)

(73) Assignee: Centese, Inc., Omaha, NE (US)

(*) Notice: Subject to any disclaimer, the term of this patent is extended or adjusted under 35 U.S.C. 154(b) by 0 days.

(21) Appl. No.: 17/813,684

(22) Filed: Jul. 20, 2022

(65) Prior Publication Data

US 2022/0355018 A1 Nov. 10, 2022

Related U.S. Application Data

(63) Continuation of application No. PCT/US2021/001476, filed on Jan. 22, 2021.

(60) Provisional application No. 62/706,429, filed on Aug. 17, 2020, provisional application No. 62/705,940, filed on Jul. 23, 2020, provisional application No. 62/705,587, filed on Jul. 6, 2020, provisional application No. 62/965,885, filed on Jan. 25, 2020.

(51) Int. Cl.
*A61M 1/00* (2006.01)

(52) U.S. Cl.
CPC ................ *A61M 1/73* (2021.05); *A61M 1/74* (2021.05); *A61M 2210/101* (2013.01)

(58) Field of Classification Search
CPC ..... A61M 1/73; A61M 1/74; A61M 2210/101
USPC .......................................................... 604/319
See application file for complete search history.

(56) References Cited

U.S. PATENT DOCUMENTS

| | | | | |
|---|---|---|---|---|
| 2003/0212337 | A1 | 11/2003 | Sirokman | |
| 2015/0174305 | A1* | 6/2015 | Bharat | A61M 1/73 604/26 |
| 2017/0143880 | A1 | 5/2017 | Luxon et al. | |
| 2018/0104391 | A1* | 4/2018 | Luxon | A61M 1/742 |
| 2019/0134363 | A1* | 5/2019 | Grziwa | A61M 1/73 |
| 2019/0358438 | A1* | 11/2019 | Fortune | A61M 25/0147 |

FOREIGN PATENT DOCUMENTS

WO WO 2021/150999 7/2021

* cited by examiner

*Primary Examiner* — Andrew J Mensh
(74) *Attorney, Agent, or Firm* — Levine Bagade Han LLP

(57) ABSTRACT

Devices and methods for managing chest or wound drainage are disclosed where in one embodiment, the system generally comprises a chest tube configured for insertion at least partially within a body of a subject, a drainage tube fluidly coupled with the chest tube, a reservoir fluidly coupled with the drainage tube, a pump in communication with the reservoir, and a controller in fluid communication with the drainage tube. The controller may be configured to determine a readiness for removal of the chest tube from the body based upon one or more removal parameters which are obtained over a period of time via the controller.

46 Claims, 42 Drawing Sheets

| Displayed Message | Description | Alarm Level | What to Do |
|---|---|---|---|
| **Use Warnings** | | | |
| SYSTEM CHECK FAILED 0010 | The system check has failed to maintain seal. | Medium | Check connections and re-test. Replace canister if error persists. |
| CANISTER FULL 0015 | The canister is full (over 1200 ml). | Medium | Replace canister. |
| BATTERY LOW 0020 | The battery is low (<20%). | Medium | Connect control module to wall power. |
| PROLONGED STANDBY 0025 | The device has been in standby for over 5 minutes. | Medium | Exit standby if no longer desired. |
| USB NOT PERMITTED 0030 | The USB cable has been detected during use. | Medium | Disconnect USB cable |
| CANISTER DISCONNECTED 0035 | The canister has become disconnected. | High | Re-connect canister. |
| DRAINAGE TUBING CLOGGED 0040 | A clog has been detected in the drainage tubing. | High | Check tubing for clogs. Confirm clamp is unclamped. |
| CHEST TUBE CLOGGED 0045 | A clog has been detected in the chest tube. | High | Check chest tube for clogs. |
| CANISTER FILTER CLOGGED 0050 | The filter in the drainage canister is clogged. | High | Replace canister. |
| EXCESSIVE AIR LEAK 0055 | An large air leak (over 3 l/min) has been detected. | High | Check all connections for leaks |
| BATTERY DEPLETED 0060 | The battery is depleted. Device shutoff is imminent. | High | Connect control module to wall power. |
| DEVICE TIPPED OVER 0065 | The device is tipped and at risk of losing suction. | High | Place control module upright. |
| **Alarms Based on Alert Settings** | | | |
| EXCESSIVE DRAINAGE 0110 | Drainage has surpassed the alarm threshold rate. | High | Check patient for signs of hemorrhage. |
| **Control Module System Faults** | | | |
| CONTROL MODULE FAULT 0210 | Internal error with control module during startup | Medium | Record error number and contact manufacturer |
| CONTROL MODULE FAULT 0215 | Internal error with control module during use. | High | Record error number and contact manufacturer |

FIG. 34

DEVICES AND METHODS FOR MANAGING CHEST OR WOUND DRAINAGE

CROSS-REFERENCE TO RELATED APPLICATIONS

This application is a continuation of International Application No. PCT/US2021/014765 filed Jan. 22, 2021, which claims the benefit of priority to U.S. Provisional Application No. 62/965,885 filed Jan. 25, 2020, U.S. Provisional Application No. 62/705,587 filed Jul. 6, 2020, U.S. Provisional Application No. 62/705,940 filed Jul. 23, 2020, and U.S. Provisional Application No. 62/706,429 filed Aug. 17, 2020, each of which is incorporated herein by reference in its entirety.

FIELD OF THE INVENTION

The present invention relates to wound and surgical drainage.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

Chest tubes are required any time air and/or liquid accumulates in the chest cavity, disrupting normal pulmonary or cardiac function. Suction is commonly applied continuously to remove excess air and/or fluid from the chest until the internal wounds have healed, at which point the chest tubes can be removed. One of the most common uses of chest tubes is to drain the area around the heart after cardiac surgery.

Despite their benefits, current chest tube systems suffer from a number of flaws. First, as liquid drains from the chest toward the suction container, it can pool in the drainage tubing and prevent the applied negative pressure from being transmitted to the chest. When this occurs, the pressure in the chest can be reduced to zero or even become positive, preventing proper drainage. Second, clogs can form in the chest tube which can obstruct the chest tube, which prevents the negative pressure from being transmitted to the chest and inhibits drainage. In fact, 36% of cardiac surgery patients experience chest tube clogging. When proper drainage is inhibited due to these factors, patients are at increased risk for accumulation of fluid around the heart, known as pericardial tamponade, which results in shock and can be fatal. Additionally, the lungs may be compressed, which can lead to respiratory compromise and can be fatal as well.

Pooling of liquid in the drainage line can theoretically be remedied by keeping the tubing straight from the patient to the collection container. However, this is nearly impossible in practice, as some slack is required to prevent accidental dislodging of the tube from the body. To combat clogging, clinicians use two methods known as milking and stripping.

Milking refers to line manipulations such as lifting, squeezing, or kneading. Stripping refers to a pulling along the length of the tube with the thumb and forefinger to increase the amount of suction at the end of the tube. However, these methods have not been shown to be effective at improving chest tube suction or drainage. In fact, stripping has actually been discouraged because it is possible to create extremely high negative pressures (up to −370 cmH2O) that may damage the tissue.

In addition to these functional flaws, current systems also measure collected fluid volume and rate of chest air leak inaccurately and/or subjectively. As a result, clinicians make cautious clinical decisions based on these measurements, keeping patients in the hospital longer than necessary.

SUMMARY OF THE INVENTION

A chest drainage system is needed which reduces or eliminates pooling of blood/liquid and/or clogging/clotting in the drainage tube and/or chest tube, and provides objective and accurate measures of collected fluid volume and chest/thoracic air leak. In addition, a system which provides info of a patient's progress would be valuable.

In one embodiment, a drainage system may generally comprise a chest tube having a chest tube drainage lumen and a drainage reservoir in fluid communication with the chest tube drainage lumen. A pump may be in fluid communication with the chest tube drainage lumen and a pressure sensor may be positioned proximal to the chest tube and in communication with the chest tube drainage lumen. Furthermore, a controller may be in communication with the pressure sensor and the pump, wherein the controller is configured to actuate the pump at a first suction level sufficient to drain a fluid from the chest tube drainage lumen, and wherein the controller is further configured to actuate the pump at a second suction level which is different from the first suction level such that an absence of attenuation in the second suction level over time is indicative of an obstruction in the chest tube.

In one embodiment for a method of draining, the method may generally comprise receiving a fluid through a chest tube having a chest tube drainage lumen, and applying a first suction level to the chest tube drainage lumen sufficient to drain the fluid from the chest tube. A pressure may be monitored within a drainage pathway from the chest tube drainage lumen via a pressure sensor in communication with a controller. Furthermore, a second suction level may be applied to the chest tube drainage lumen which is different from the first suction level such that an absence of attenuation in the second suction level over time is indicative of an obstruction in the chest tube.

In one embodiment for a drainage system, the system may generally comprise a chest tube configured for insertion at least partially within a body of a subject, a drainage tube fluidly coupled with the chest tube, a reservoir fluidly coupled with the drainage tube, a pump in communication with the reservoir, and a controller in communication with the reservoir, wherein the controller is configured to determine a readiness for removal of the chest tube from the body based upon one or more removal parameters which are obtained over a period of time via the controller.

In one embodiment for a method of removing a drainage system, the method may generally comprise receiving a fluid from a body of a subject through a drainage tube fluidly coupled with a chest tube inserted at least partially within the body, monitoring the drainage system via a controller for one or more removal parameters over a period of time, and determining a readiness for removal of the chest tube from the body via the controller based upon the one or more removal parameters.

BRIEF DESCRIPTION OF THE DRAWINGS

FIG. 26 shoes an embodiment of the chest tube in which the drainage holes are not completely punched through.

FIG. 34 shows some common alarm codes.

FIG. 66 shows an embodiment of the system which includes a sealed cartridge which is configured to capture contaminants in collected air.

DETAILED DESCRIPTION OF THE INVENTION

Figure 1:
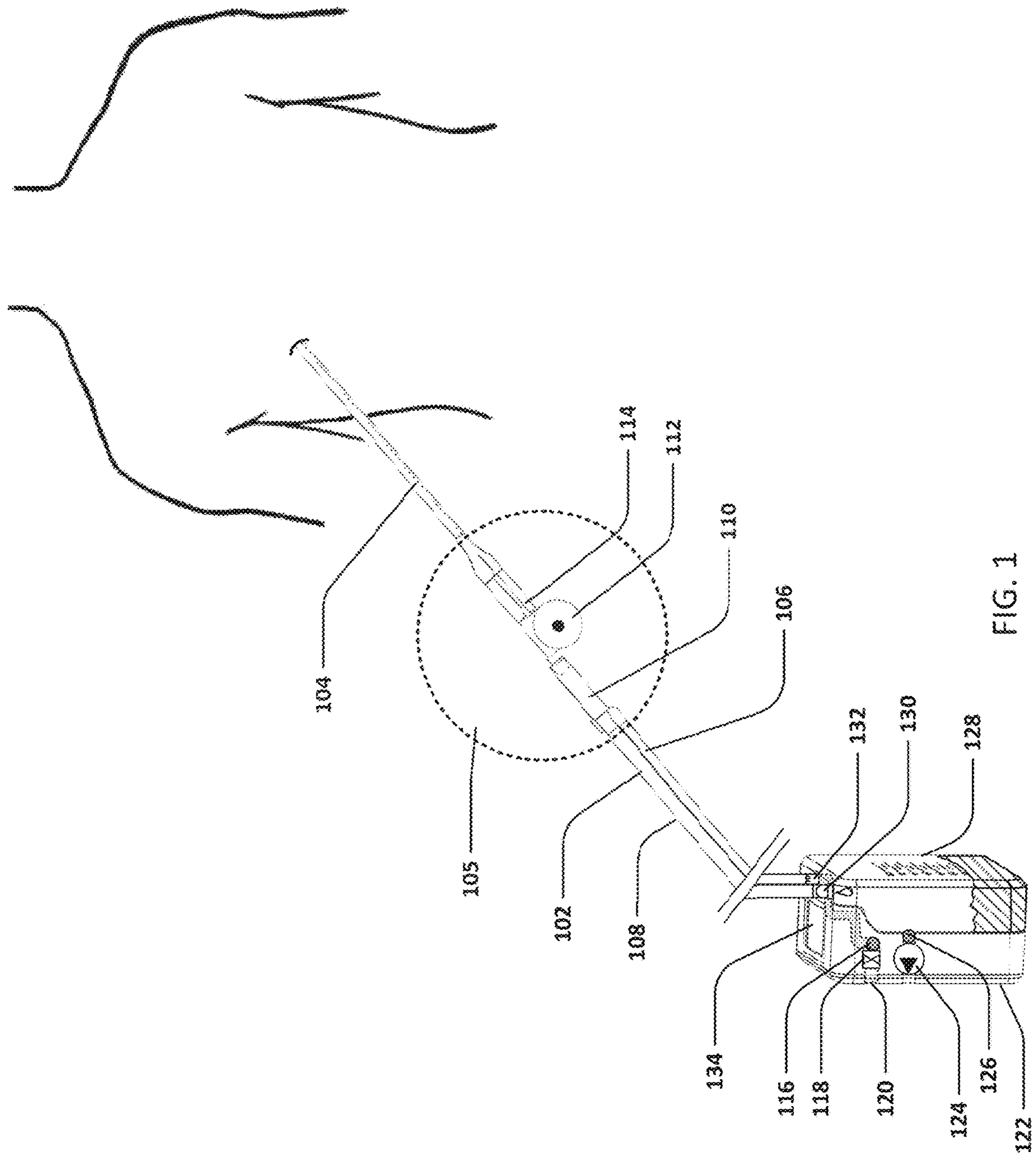
FIG. 1 shows an embodiment of the chest drainage system.

Disclosed is a chest drainage system which reduces or eliminates pooling of blood/liquid and/or clogging/clotting in the drainage tube and/or chest tube, and provides objective and accurate measures of drained fluid volume and chest air leak, in addition to providing info regarding patient status and/or progress.

The chest drainage system continuously monitors chest tube and drainage tube status and clears pooled liquid in the drainage tube, and/or a clogged chest tube when necessary to restore negative pressure to the chest, or in some instances, zero, or near zero, pressure to the chest, allowing it to drain. The system may include active and/or passive valve functions, as well as a controller (also referred to herein as a monitor, and/or control module) for monitoring the pressures in the system. The controller may control a pump for assisting in clearance of pooled liquid and/or clots in the drainage tube and/or chest tube. The controller may also control any active valves and/or suction device in response to measured pressure signals. The controller may also measure and communicate collected fluid volume and air leak information. The chest drainage system performs at least six primary functions:

Functions:

1. Drainage Tube Blockage Detection

The chest drainage system detects pooled liquid in the drainage tube by monitoring the pressure at or near the chest tube-drainage tube interface (the tube-tube interface or junction area, or barb area). Pooled liquid in the drainage tube is indicated by a decrease in vacuum (increasing pressure) at the tube-tube interface. The chest drainage system may measure pressure with a sensor incorporated into the controller. The sensor may be in fluid communication with the tube-tube interface area via a fluid filled lumen (the relief lumen). The relief lumen may be open to atmosphere on the other end, and be filled with air. A valve (drainage tube valve, drainage tube relief valve or drainage tube relief lumen valve) may be used to open the relief lumen, exposing the tube-tube interface to atmospheric pressure. The drainage tube relief valve may also close the relief lumen, and may include a vent which prevents the transmission of bacteria and viruses from the atmosphere into the relief lumen. The drainage tube relief valve may be opened and closed by the controller based on the measured pressure at the tube-tube interface area.

Alternatively, the pressure sensor may be placed at the tube-tube interface area. In this embodiment, the pressure sensor is in communication with the controller. Alternatively, the drainage tube relief valve may be passive, either with or without a relief lumen. Alternatively, the drainage tube relief valve may be operated manually.

Alternatively or additionally, a pressure sensor may be placed in the chest fluid collection chamber/reservoir/cassette/receptacle/canister. At a time when the vacuum pump is running, whether to perform a chest tube clearance, a drainage line clearance, or simply to regulate the suction, pressure in the canister may become more negative if a clog in the drainage line is present. A preset pressure (vacuum) threshold may be set by the user or the controller, the exceeding of which, indicates a blocked drainage lumen.

Alternatively, pressure sensors may be present both in the canister and at or around the tube-tube interface. The controller may continuously monitor the pressure differential between these two pressure sensors and detect a blocked drainage tube if the difference exceeds a pre-set threshold for the pressure difference.

2. Drainage Tube Blockage Clearance

When a blocked drainage line is detected (or at timed intervals), the controller of the chest drainage system may clear the drainage tube by opening the drainage tube relief lumen valve which is in fluid communication with the tube-tube interface area. Opening the drainage tube relief lumen valve allows air to sweep away the liquid, and any blockage, in the drainage tube into the drainage container/reservoir. A pump which may be integrated with the controller, applies negative pressure to the drainage tube (via a collection reservoir/cassette/chamber). Optionally the pump may also apply positive pressure to the relief lumen (rather than its being open to atmospheric pressure) to help clear the blockage. Proper negative pressure at the chest is then restored. Optionally, the system may apply negative pressure (or an increased negative pressure) to the drainage tube without opening the relief lumen valve, or in addition to opening the relief lumen valve to restore proper suction. This measure may be performed when the controller senses a blockage in the drainage tube, or may be performed at set intervals. Pressure measured at the tube-tube interface may drive the controller to initiate a drainage tube clearance cycle. The pressure measured at the tube-tube interface may also or alternatively control the pump so that a desired suction level is maintained at the tube-tube interface during a clearance cycle.

3. Chest Tube Blockage Detection

Clots or clogs may form in the chest tube. To detect a blocked chest tube, the controller may pull suction intermittently to a level that exceeds the crack pressure of the chest tube relief valve. Once it hits this first pre-set threshold the pump turns off or reduces the suction (to a more positive pressure level). At this point, if there is no blockage, or if the blockage is able to be cleared via the transfer of the increased suction, the valve will open and the measured vacuum will attenuate down to a second pre-set threshold (more positive than the first threshold). If the controller does not sense this attenuation over a specified time interval, the controller determines that the chest tube is blocked and may issue an alarm, or attempt alternative measures of clearing the chest tube, such as increasing the suction applied to the chest tube to a third threshold. Pressure may be measured at the tube-tube junction or in the canister or elsewhere in the system.

4. Chest Tube Blockage Clearance

To clear blockages in the chest tube, the suction magnitude applied at the tube-tube interface may be increased by the controller. A passive chest tube relief valve, in fluid communication with a chest tube relief lumen, may be configured to open when the pressure differential across it reaches a set level. The chest tube relief valve may be open to atmospheric pressure and include a filter or vent to prevent bacteria etc. from entering the system. Once the chest tube relief valve is open, the chest tube will be cleared. The chest tube relief valve may be configured to close at a pressure differential which is less than that of the opening pressure, to ensure the valve stays open long enough for the chest tube to be cleared and to minimize the flow resistance of the valve. Alternatively, the chest tube relief valve, may be an active valve, which the controller opens and closes based on pressures measured in the tube-tube interface area and/or in the chest tube relief lumen. An active chest tube relief valve may open and close at the same pressure differential or open and close at different pressure differentials.

Alternatively, the chest tube relief valve may be connected to the drainage line relief lumen and either controlled directly by the controller via a connection to the controller, or via pressure changes introduced through the drainage line relief lumen by the controller.

In some embodiments, one or more of the valves are passive and set to open at a set pressure and stay open until the same, or another, set pressure is reached. In some embodiments, one or more of the valves are active and directly controlled by the controller. In either case, one or more valves may be set to open at one pressure, and close at another pressure.

The intervals for clearing the chest tube may be different than the intervals for clearing the drainage line.

5. Chest Air Leak Detection

To detect air leaks from the patient's chest, the controller monitors the flow of air pumped from the canister to maintain the prescribed level of suction within the canister. This is done with a flow meter and/or measuring the revolutions of the pump necessary to evacuate the air.

6. Drainage Fluid Volume Measurement

The controller may measure the volume (or flow) of drained chest fluids that is collected within the canister over time. Collected fluid volume measurements are preferably made with a non-contact capacitive sensor, but may alternatively be made with optical sensors, pressure sensors, acoustic (such as ultrasonic) sensors, a camera, or any other liquid level sensing methods known in the art.

7. Chest Tube Removal Guidance

The controller may monitor certain parameters related to patient progress, including fluid volume drainage status and changes, air leak status and changes, response to certain air leak challenges, drainage tube and/or chest tube patency status and changes, pressure status and changes at one or more points in the system, respiratory rate status and changes, tidal volume status and changes, etc. Based on analysis of one or more than one of these parameters, the controller informs, and communicates to the user, chest tube removal readiness. The information communicated may include the expected timing for chest tube removal readiness, when the chest tube is ready for removal, confidence level for chest tube removal, and/or general patient progress. Communication may be via display, audible, remote communication, etc.

FIG. 1 shows an embodiment of the chest drainage system with an active drainage tube relief valve and a passive chest tube relief valve. Chest tube 104 is connected to, and in fluid communication with, drainage tube 108. Chest tube 104 includes both a chest tube drainage lumen and a chest tube relief lumen. Drainage tube 108 includes both drainage tube drainage lumen 102 and drainage tube relief lumen 106. Drainage tube relief lumen 106 is in fluid communication with drainage tube drainage lumen 102. Drainage tube drainage lumen 102 is in fluid communication with the chest tube drainage lumen. The connection among the 3 lumens—chest tube drainage lumen, drainage tube drainage lumen and drainage tube relief lumen, occurs at the barb, or near tube-tube junction 105, which is at or near the chest tube/drainage tube junction. In some embodiments, the drainage tube relief lumen may connect to the drainage tube or chest tube at a different location. The chest tube, drainage tube and drainage tube relief lumen may be connected with drainage tube connection barb 110.

In some embodiments, the drainage tube relief lumen may be in fluid communication with the chest tube relief lumen.

Figure 6A:
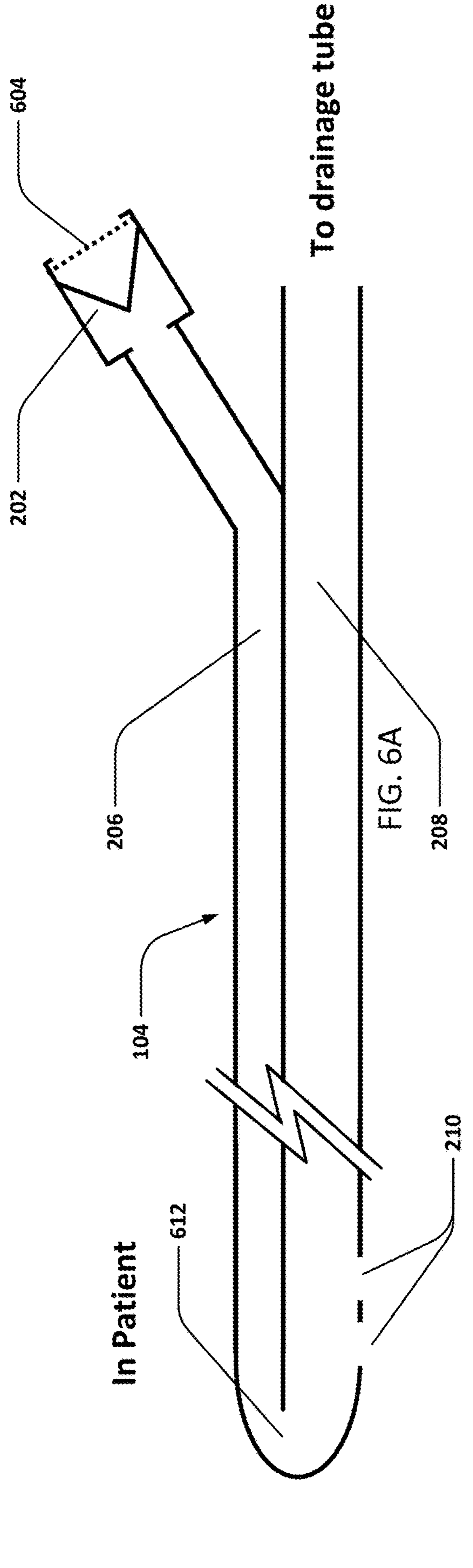
FIGS. 6A and 6B shows a diagram of an embodiment of the chest tube.
Figure 6B:
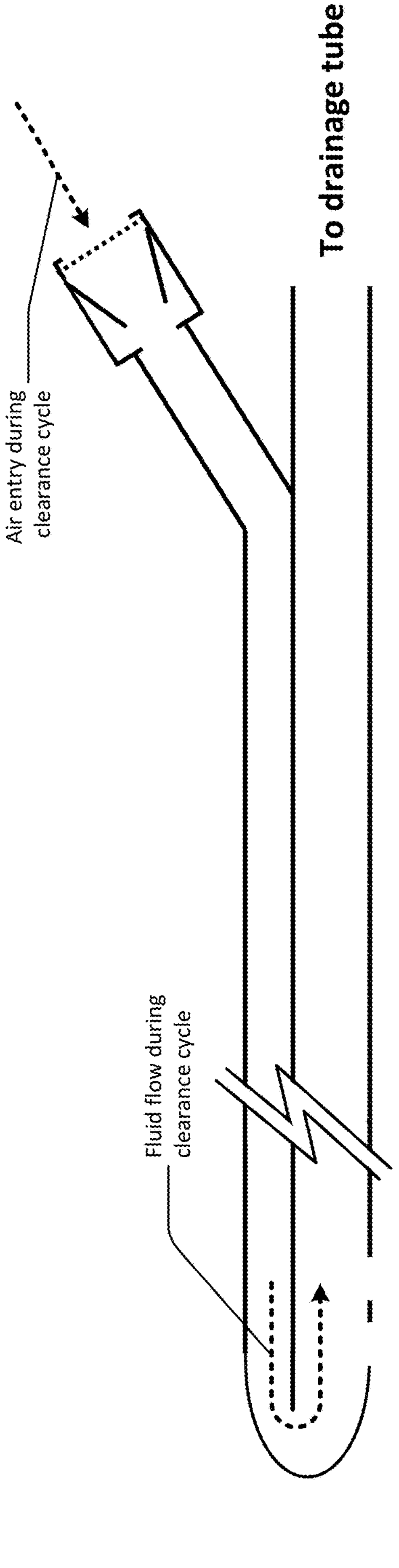

Chest tube relief valve 112 may be incorporated to the chest tube, or a separate adapter designed to connect to the chest tube, for example, into chest tube connection barb 114. In this embodiment, the chest tube has at least two lumens, chest tube drainage lumen and chest tube relief lumen, as shown in FIGS. 6A and 6B. Pressure sensor 116, drainage tube relief lumen valve 118, and filter/vent 120 are in fluid communication with drainage tube relief lumen 106.

Controller 122 may include pump 124, pressure sensor 116, drainage tube relief lumen valve 118, filter/vent 120 (which may be on either side of valve 118 and pressure sensor 116), and fluid reservoir (or suction canister) 128, which is in fluid communication with drainage tube 108 via drainage tube drainage lumen connector 130 and drainage tube relief lumen connector 132. However, the drainage line relief lumen may connect to the controller directly, without connecting through the canister. The controller may also include display 134, which may receive input, for example via a touch screen, in addition to displaying information.

Controller 122 may include a suction device, such as pump 124 to create a negative pressure, or suction, force on the drainage tube (possibly via collection canister 128) which is in fluid communication with the chest tube and the chest tube relief valve. In this way, suction may be maintained on the chest cavity to promote chest fluid drainage and aid with patient breathing. The mechanism for creating the negative pressure may be a pump or any other suitable mechanism. The controller and the suction device may be incorporated or may be separate. Any communication between the controller and the suction device and/or any of the valves may be wired or wireless.

Controller 122 may also include pressure sensor 126 on the canister side of the pump, to measure and/or monitor the pressure within the canister. The controller may also include a flow sensor or flow meter on either side of the pump, and/or one-way valve on either side of the pump to measure air/gas pumped out of the canister. The air flow may also or alternatively be measured by measuring the pump revolutions.

Pressure sensor 116 senses the pressure in tube-tube interface area 105 (via drainage tube relief lumen 106). When the drainage tube is blocked or restricted, the pressure in the tube-tube interface area increases. When this pressure increases to a set pressure (generally, a negative pressure, or a pressure near zero), controller 122 opens drainage tube relief valve 118 (which is normally closed) to allow filtered atmospheric pressure air to enter drainage tube relief lumen 106. Drainage tube relief valve 118 may be a solenoid valve. This influx of air, in combination with the negative pressure in the drainage tube caused by pump 124, acts to clear the drainage tube of blockages/restrictions. Once the pressure in the tube-tube interface area returns to normal, or a set pressure, and/or after a set time, the controller closes drainage tube relief valve 118. Alternatively, the drainage tube valve may be a passive valve set to open and close at set pressures.

Alternatively, the controller may be configured to open the drainage tube relief valve periodically, regardless of the pressure measured in the tube-tube interface, which in some embodiments, is not monitored.

The monitor/controller may monitor pressure in the drainage tube relief lumen and may pull additional suction in the fluid reservoir/suction canister as needed to maintain the suction pressure in the proper range at the tube-tube interface area. For example, when the desired pressure is set to −20 cmH2O, the monitor may activate the suction pump to keep the pressure at the tube-tube interface area between −15 cmH2O and −25 cmH2O or between −18 cmH2O and −22 cmH2O. In some embodiments, the monitor may activate the pump and drainage tube relief valve 118 at regular temporal intervals as a preventative measure to clear any pooled liquid from the drainage line. This is done by the controller activating suction pump 124 while simultaneously opening drainage tube relief valve 118 to allow air to sweep accumulated liquid into the suction canister via the drainage tube.

The chest tube may become blocked or restricted. To clear restrictions, the suction magnitude applied by the controller to the drainage tube and experienced by the tube-tube interface may be increased. When the pressure in the tube-tube interface reaches a set low level (i.e. high level of suction), chest tube relief valve 112 opens and allows filtered atmospheric air to enter the relief lumen of the chest tube (see FIGS. 6A and 6B for detail). This influx of air, in combination with the negative pressure in the drainage tube and tube-tube interface area caused by pump 124, acts to clear the chest tube of blockages/restrictions. In instances where a chest tube blockage cannot be cleared, an alarm may sound. A passive valve is shown here, although an active valve, directly controlled by the controller, may be used. Alternatively, a valve which is operated manually, may be used. Any of the operations disclosed herein which may be controlled by the controller, may alternatively be controlled passively, or manually. For example, valve functions, suction functions, etc.

The chest tube relief valve may have a different opening pressure and closing pressure. For example, the chest tube relief valve may open at a higher pressure differential (i.e. a more negative pressure in the tube-tube interface area), and close at a lower pressure differential. This allows the valve to stay closed until a clear chest tube blockage is present and to minimize the flow resistance of the valve. Once the valve is open, this allows the valve to stay open to completely clear the chest tube blockage, even if the tube-tube interface area pressure increases so that the pressure differential across the chest tube valve drops below the valve opening pressure. In other words, the pressure within the tube-tube interface area may be more negative when a chest tube blockage is created, but less negative, as the chest tube blockage is being cleared.

FIG. 1 shows one chest tube in use with the chest drainage system, but in some embodiments, more than one chest tube may be used with the system. Each chest tube may have its own drainage lumen and relief lumen and valve, or they may share a relief lumen and/or valve.

Figure 2:
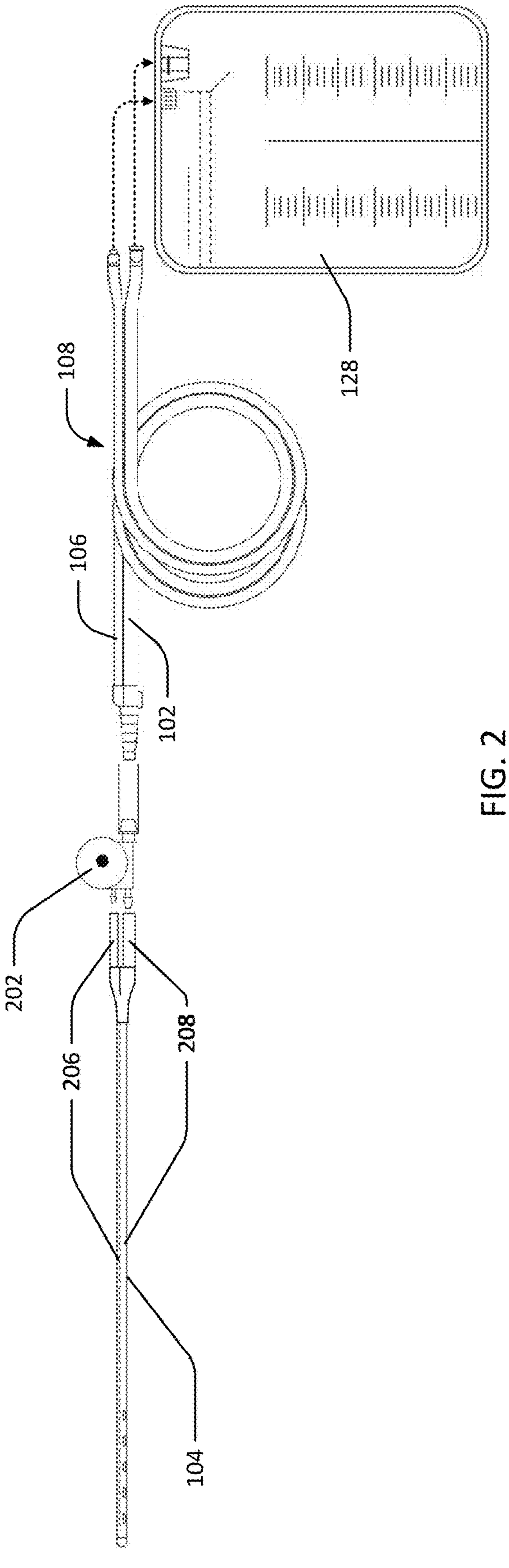
FIG. 2 shows various components of the chest drainage system.

FIG. 2 shows various components of the chest drainage system, including chest tube 104, chest tube relief lumen 206, chest tube drainage lumen 208, chest tube relief valve 202, drainage tube 108, drainage tube relief lumen 106, drainage tube drainage lumen 102, and canister 128.

Figure 3:
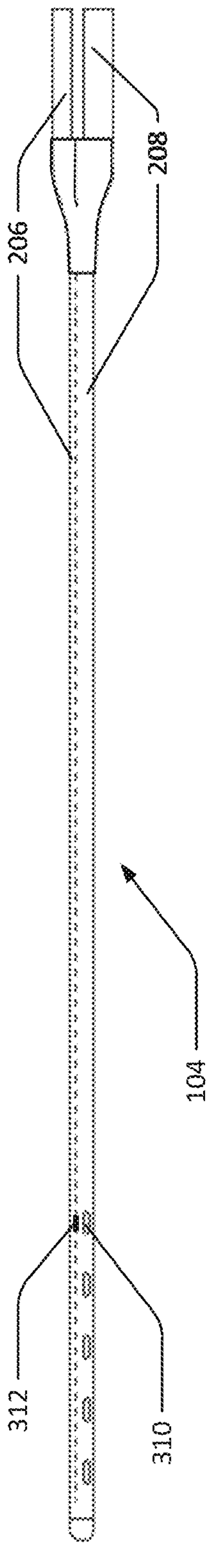
FIG. 3 shows an enlarged view of the chest tube.

FIG. 3 shows an enlarged view of chest tube 104, including openings 310 for fluid drainage from the chest. Openings 310 are in fluid communication with chest tube drainage lumen 208. A radiopaque marker or markers may be incorporated into the chest tube. For example, a marker, such as marker 312, may be included at the most proximal drainage hole in the chest tube to act as a reference point for verification of depth of insertion and location of the chest tube within the patient. A marker may also be included at or near the distal end of the chest tube.

Figure 4:
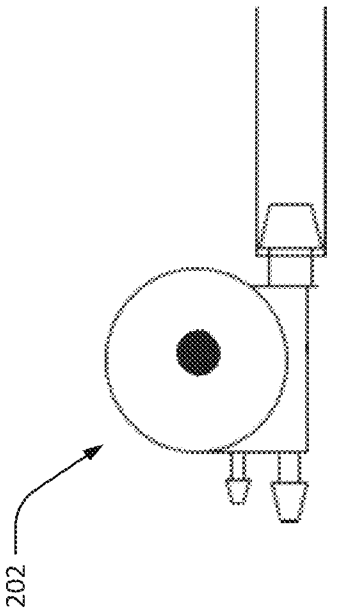
FIG. 4 shows an enlarge view of the chest tube relief valve.

FIG. 4 shows an enlarge view of chest tube relief valve 202.

Figure 5:
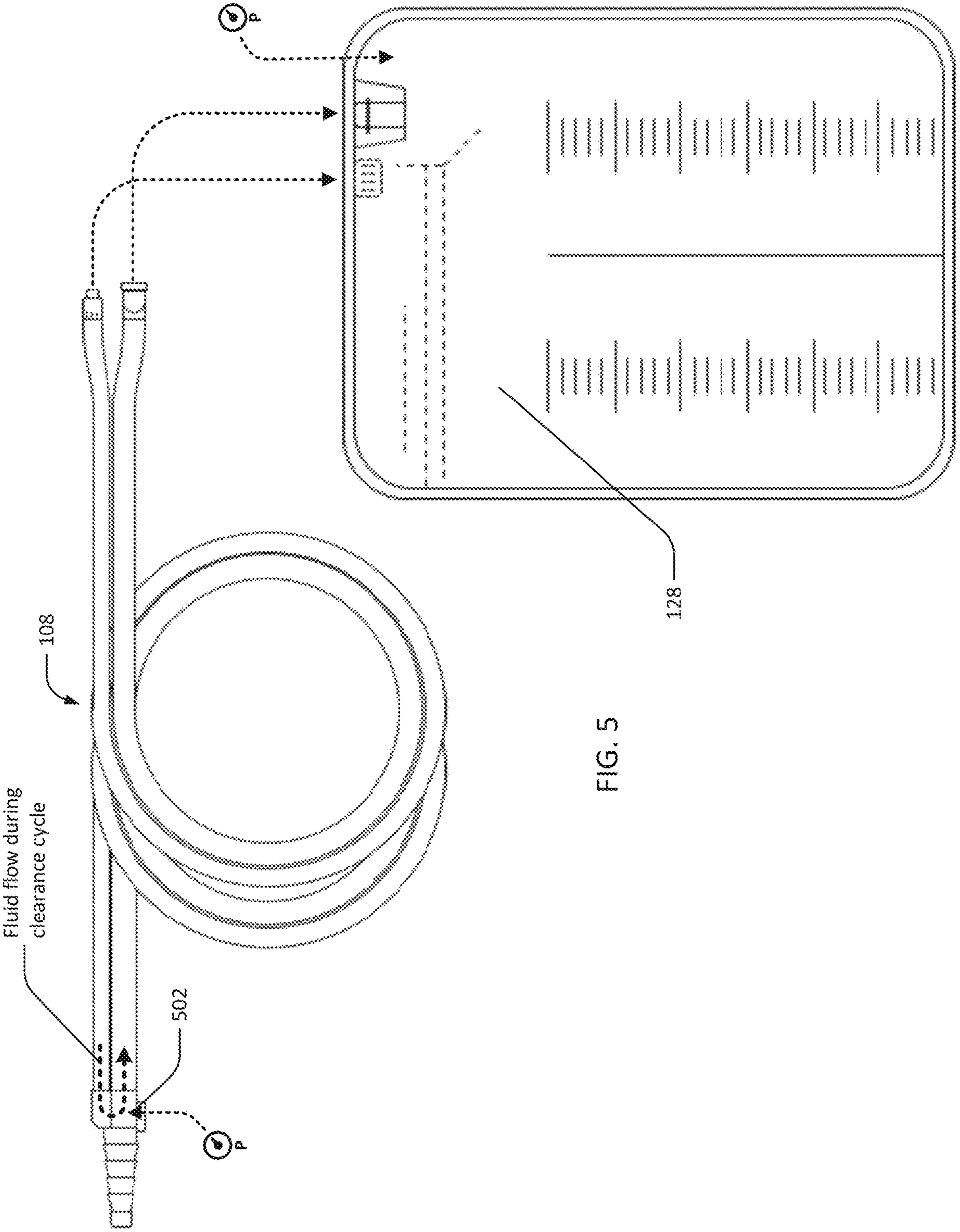
FIG. 5 shows an enlarged view of the drainage tube and the canister.

FIG. 5 shows an enlarged view of drainage tube 108 and canister 128. Preferably, the prescribed suction level is identical to or close to the suction level seen by the patient. The controller monitors pressure at the patient (at the drainage tube barb 502) using pressure sensor 116 connected pneumatically to the drainage tube barb via the drainage tube relief lumen of the drainage tubing. This pressure may be intermittently or constantly compared to pressure level set via the controller. If the pressure veers out of an acceptable range, the pump turns on or increases to reestablish the desired (set) negative pressure level. Any overshoot (pressure going too negative) during adjustment may be corrected by the controller (or manually) opening solenoid valve 118 in fluid communication with the drainage tube (at barb 502 or elsewhere) which allows atmospheric air to enter the system through a filter membrane (for example, through a 0.2-micron membrane).

When a drainage line purge cycle is initiated, the pump will turn on or increase suction and the drainage line relief valve will be opened to allow atmospheric air to enter the drainage tube relief lumen after passing through a filter membrane (for example, a 0.2-micron filter membrane). This air is pulled to drainage barb 502 and swept down the drainage lumen of the drainage tubing, along with other fluids, to the drainage canister. The pressure within the system during this process is affected by the pump RPM and the smallest inner diameter of the drainage tube relief valve 118 (for example, a solenoid valve) and other tubing or channels that make up the drainage relief lumen. The pump may operate at a specified rate to maintain suction within the system without ramping up to dangerous levels.

During this process, pressure may also be monitored at canister 128 to reduce the frequency of solenoid valve activation due to its proximity to barb 502.

Additionally, two pressure sensor readings (at barb 502 and at canister 128) may be used and/or compared and analyzed by the controller and used to diagnose various situations occurring within the system:

1. If the canister sensor is reading the prescribed suction level and the barb pressure is reading a lower suction level (a less negative pressure) than the prescribed suction level, the system may initiate a drainage line clearance cycle.

2. If the controller pulls additional (up to 100 $cmH_2O$) suction and the canister pressure sensor reading shows an increase in negative pressure (more negative) while the barb pressure reading does not change, or changes less than the applied suction, the system will alert for an obstruction in the drainage line.

3. If the controller initiates a drainage line clearance cycle by pulling additional (up to 100 $cmH_2O$) suction and the barb suction level reading increases (pressure level decreases) past a set threshold, the controller may determine that the chest tube relief valve did not open to clear the chest tube and therefore the system will alert for a clog in the chest tube drainage line.

4. If the controller is being triggered to correct the system suction level frequently (more frequently than a set frequency threshold), a drainage line clearance or chest tube clearance cycle may be performed to clear any fluid buildup in the line and/or chest tube.

5. If the controller is being triggered to correct the system suction level frequently, it may be indicative of an active air leak, in which case the current air leak rate will be displayed on the controller display screen and/or an alert may sound.

Pressure sensor(s) may reside at various locations in the system. A pressure sensor may be incorporated within the chest tube valve device near the chest tube, and/or near the controller, in the receptacle, in the chest tube, or within or near the tube-tube interface area. Pressure sensed at one or more location may be used to determine whether there is a change in pressure anywhere in the system, which may be used to identify drainage tube blockages and/or chest tube blockages. If an impediment is detected, an audible alarm may sound, and/or the controller may automatically clear the drainage tube and/or chest tube.

Chest Tube Detail

FIG. 6A shows a diagram of an embodiment of chest tube 104. Chest tube 104 includes chest tube drainage lumen 208 and chest tube relief lumen 206 incorporated into the chest tube. Chest tube relief valve 202 and filter/vent 604 are also shown in fluid communication with chest tube relief lumen 206, which is in fluid communication with chest tube drainage lumen 208 via opening 612. Drainage openings 310 allow fluid from the chest cavity to enter the chest tube and drain through chest tube drainage lumen 208. Generally when in use, openings 210 and opening 612 are inside the patient.

During successful chest drainage, chest tube relief valve 202 is in the closed position. In this position, fluid draining from the chest generally does not enter chest tube relief lumen 206 because of the fluid column in the chest tube relief lumen. A smaller diameter chest tube relief lumen may help prevent fluid from entering the chest tube relief lumen. The pressure in chest tube relief lumen 206 may be slightly negative during chest tube drainage due to the negative pressure exerted by the pump on the drainage line, the chest tube drainage lumen, and to some extent, the chest tube relief lumen. The chest tube may become blocked or restricted, because of blood clots etc.

When a chest tube clog clearance cycle is initiated, the pump generates additional suction above the set level (to a more negative pressure) to open the chest tube relief valve. As this negative pressure drops to a set valve opening pressure, chest tube relief valve 202 opens, allowing atmospheric (i.e., more positive pressure) air to enter the chest tube relief lumen of the chest tube by passing through filter membrane 604 and valve 202. The air is pulled to the distal tip of the chest tube, through opening 612, and into the chest tube drainage lumen, where the air and other fluids are swept through the chest tube drainage lumen towards the drainage canister. This clearing is shown in FIG. 6B.

The chest tube relief valve is normally closed, as shown in FIG. 6A. The chest tube relief valve opens when the suction level applied by the pump to the drainage lumen is great enough (negative enough P) to overcome the forces applied to open the chest tube relief valve, as shown in FIG. 6B. When this occurs, the chest tube relief valve opens, allowing air to enter the system. The chest tube relief valve remains open until the suction level drops to the valve closing pressure. This closing pressure may be less negative than the valve opening pressure.

Once the pressure in the chest tube relief lumen increases back to a set valve closing pressure, chest tube relief valve 202 closes and normal drainage continues. The chest tube relief valve opening pressure may be different than the chest tube relief valve closing pressure. For example, the chest tube relief valve opening pressure may be at a higher pressure than the chest tube relief valve closing pressure.

For example, the chest tube relief valve may open when the pressure differential across the valve is about −10 cmH2O, about −20 cmH2O, about −30 cmH2O, about −40 cmH2O, about −50 cmH2O or as even high as about −100 cmH2O. Or for example, the chest tube relief valve may open when the pressure differential across the valve is within a range of about −10 cmH2O to about −20 cmH2O, or within a range of about −20 cmH2O to about −30 cmH2O, or within a range of about −30 cmH2O to about −30 cmH2O, or within a range of about −40 cmH2O to about −40 cmH2O, or within a range of about −50 cmH2O to about −100 cmH2O.

The chest tube relief valve may close at the same range, or at a lower differential than the opening pressure. For example, the chest tube relief valve may close at a pressure differential of about to 0 cmH2O, about −5 cmH2O, about −10 cmH2O, about −15 cmH2O, or about −20 cmH2O. Or for example, the chest tube relief valve may close at a pressure differential range of about to 0 cmH2O to about −5 cmH2O, or a range of about −5 cmH2O to about −10 cmH2O, or a range of about −10 cmH2O to about −15 cmH2O, or a range of about −15 cmH2O to about −20 cmH2O.

The chest tube relief valve may take a variety of known forms, including but not limited to a check valve, umbrella valve, ball valve, Belleville valve, X-fragm valve, cross-slit valve, or dome valve. The valve system preferably has a filter in place to prevent the entrance of bacteria or viruses from the atmosphere into the patient.

In some embodiments of the chest tube, chest tube relief valve is active, not passive, and is controlled directly by the controller. In some embodiments of the chest tube, chest tube relief valve is operated manually.

In some embodiments of the chest tube, chest tube relief valve is incorporated into the chest tube. In some embodiments, the chest tube relief valve is incorporated into a connecter which is connected to the chest tube. In some embodiments of the chest tube, both the chest tube relief lumen and the chest tube relief valve are incorporated into a connecter which may be connected to a chest tube.

In some embodiments, chest tube relief valve 202 takes the form of a magnetic check valve that has a substantial difference in the pressure differential required to open the valve, and the pressure differential required to keep the valve open (or close the valve), thereby amplifying the toggling effect of the valve. This is preferable to increase the effectiveness of the clog clearance cycle, because it allows for a greater pressure differential when the air is sweeping the chest tube drainage lumen via the chest tube relief lumen than if the valve opened and closed at the same pressure. The valve is normally closed in order to maximize drainage of liquid as it enters the chest tube and to reduce the need for continuous pumping.

Chest Tube Relief Valve

Figure 7:
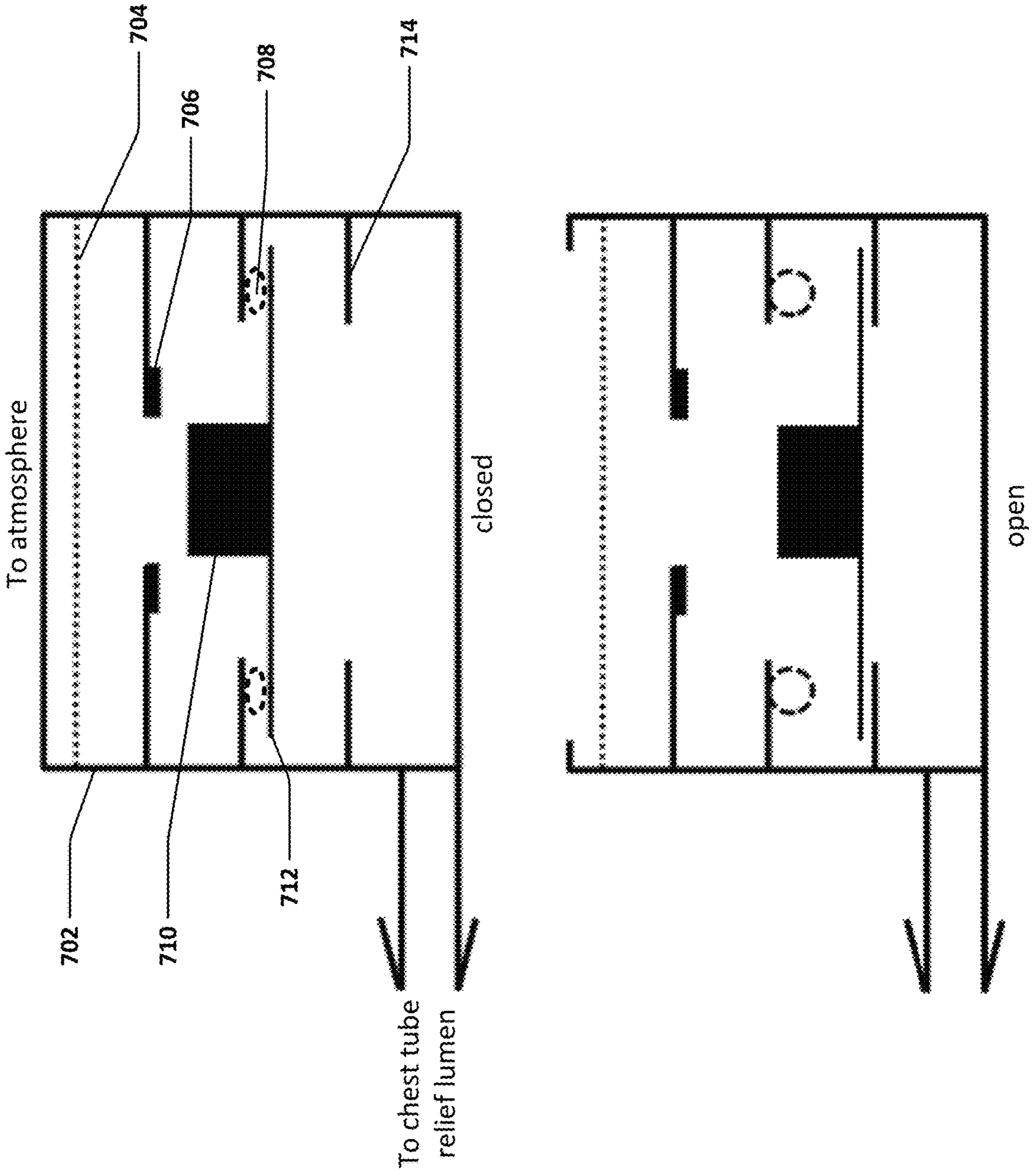
FIG. 7 shows a magnetic embodiment of the chest tube relief valve.

FIG. 7 shows a magnetic embodiment of the chest tube relief valve. The magnetic chest tube valve includes housing 702, filter 704, ferrous plate 706, gasket 708, magnet 710, seal plate 712, and positioning lip 714. When the pressure differential across the valve increases above a desired threshold, for example −50 cmH2O, the force caused by the pressure differential is enough to overcome the magnetic force between the magnet and the ferrous plate, thereby moving the two away from each other. Once the magnet and the ferrous plate move away from each other, the magnetic force rapidly diminishes, as the magnetic force is proportional to $(1/r^3)$ where r is the distance between the magnet and the plate. At the same time, the opposing spring force also diminishes, but less rapidly, as it is proportional to (x), where x is the length of spring that has been compressed. Therefore, once the seal plate moves slightly away from the gasket, the spring force can overcome the magnetic force and push the seal plate into the completely open position (the pressure during this time remains relatively constant due to the reservoir of suction in the system). As a result, the amount of pressure necessary to keep the valve open is less than the pressure that was required to open it. This second pressure value, for example −50 cmH2O, is determined by the maximum distance the magnet and seal plate can travel away from the ferrous plate, which is in the embodiment shown in FIG. 7 determined by positioning lip 714 in the housing that sets this distance.

Frequency of periodic clog clearance function activation at the controller may be 5 minutes or may be longer such as every 10 or 15 minutes. Air leak measurements may be temporarily suspended during the clog clearance cycle. The clog clearance cycle (either chest tube clearing or drainage tube clearing) frequency may be set by the user via the display/input interface.

Some embodiments of the chest tube relief valve may allow for selectable crack pressures. The activation mechanism may take the form of a button, switch, dial, or similar implement that mechanically alters the crack pressure by adjusting the stand-off distance of the magnetic seal allowing either higher or lower transmitted suction levels to open the valve. The adjustment can be a permanent alteration to the activation level of the relief valve or as a temporary override. A similar outcome may be achieved by altering the electromagnetic field in the proximity of the valve.

In some embodiments of the chest tube relief valve the clinician may temporarily open the chest tube relief valve allowing for the inflow of air to the chest tube relief lumen. This can either open the internal valve of the chest tube relief valve or bypass the chest tube relief valve by opening a separate bypass port in communication with the chest tube relief lumen. The activation mechanism may take the form of a button, switch, dial, or similar. The function can be used to assist in the activation of, or be used in place of, a chest tube clog clearance cycle. For example, the temporary or bypass function may be used to initiate clog clearance on a more frequent interval than that of the controller, to ensure clear chest tubes and drainage lines prior to measurement of fluid output, in place of the automated clog clearance feature, or for use with a different type of suction system. The bypass or adjustment can be a permanent alteration to the activation level of the relief valve or as a temporary override.

In some embodiments of the relief valve, the internal gasket that creates the seal has knob or rib features that interface with the actuator to support it uniformly, helping to prevent irregular orientation of the actuator and to facilitate a full “popping” of the actuator instead of an angled or partial actuation.

In some embodiments of the relief valve, an integrated feature or accessory may be incorporated into the chest tube relief valve when multiple valves are used. This feature positions the valves in a desired configuration in relation to each other. This feature may be incorporated to prevent the magnetic attraction between the valves from pulling them all together, potentially altering performance and/or function, and may take the form of, for example but not limited to, a ball and socket, rod and channel, or other form where multiple valves may be connected via a press-fit function. Alternatively, an accessory component may exist which has channel or pocket features which the valves connect into, that hold them in a desired orientation. In some embodiments of the accessory component, the valves may move relative to one another in ways that do not cause magnetic interference which allows for variation in position relative to the patient to accommodate varying chest tube lengths and placements.

Figure 38:
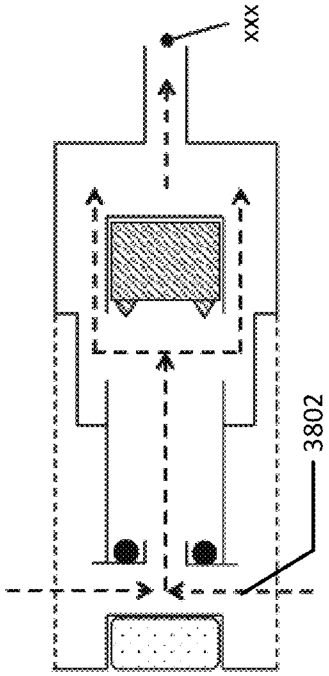
FIGS. 37 and 38 show embodiments of the chest tube relief valve.
Figure 37:
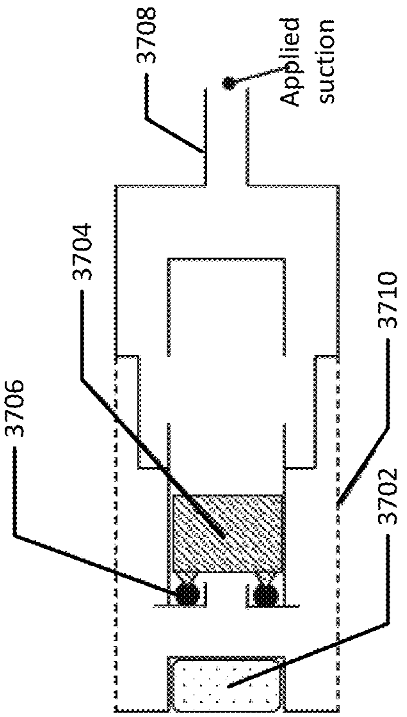

In some embodiments of the relief valve, the valve takes the form of a cylindrical shaped device in which a piston-like component (actuator) moves between two locations, either opening or closing the valve, as shown in FIGS. 37 and 38. F shows the closed position of the valve and FIG. 38 shows the open position of the valve. In the closed position, magnet 3702 pulls actuator 3704 into or onto the surface of gasket 3706, creating a seal and preventing airflow through the valve. When a prescribed level of suction is applied to outlet 3708 of the valve, the magnetic force holding the actuator against the gasket is overcome and the actuator is able to freely move into the open position, which allows air to enter the valve, after passing through filter membrane 3710, and flow through the valve outlet, as shown by arrows 3802. Once the applied suction drops down to a predefined level, the magnetic force overcomes the pressure force of the airflow on the actuator (which holds the valve in the open position) and the actuator re-seals against the gasket, closing the valve.

In some embodiments of the chest tube relief valve, a second magnet is used opposite the first magnet to facilitate full actuation of the valve (for example, maximizing air flow) and optimized closing of the valve (for example, keeping the valve open for a longer period of time).

Multiple Chest Tubes

Embodiments of the chest drainage system may include the ability to support more than one chest tube. For example, the system may support up to 2 chest tubes. Alternatively, the system may support up to 3 chest tubes. Alternatively, the system may support up to 4 chest tubes. Alternatively, the system may support up to 5 chest tubes. Alternatively, the system may support up to 10 chest tubes. Some embodiments include the ability to configure the system to be used with one or more “off the shelf” chest tubes. “Off the shelf” (OTS) chest tubes may not include a chest tube relief lumen or a chest tube relief valve. For example, in a system which supports 3 chest tubes simultaneously, the controller may be configured to support any combination of OTS chest tubes and proprietary chest tubes (chest tubes with a chest tube relief lumen and a chest tube relief valve) (P). For example, a 3 chest tube system may be configured for:

P P P
P P OTS
P OTS OTS
OTS OTS OTS

The system may alternatively be configured to be used with fewer than the maximum number of chest tubes it supports.

Figure 8A:
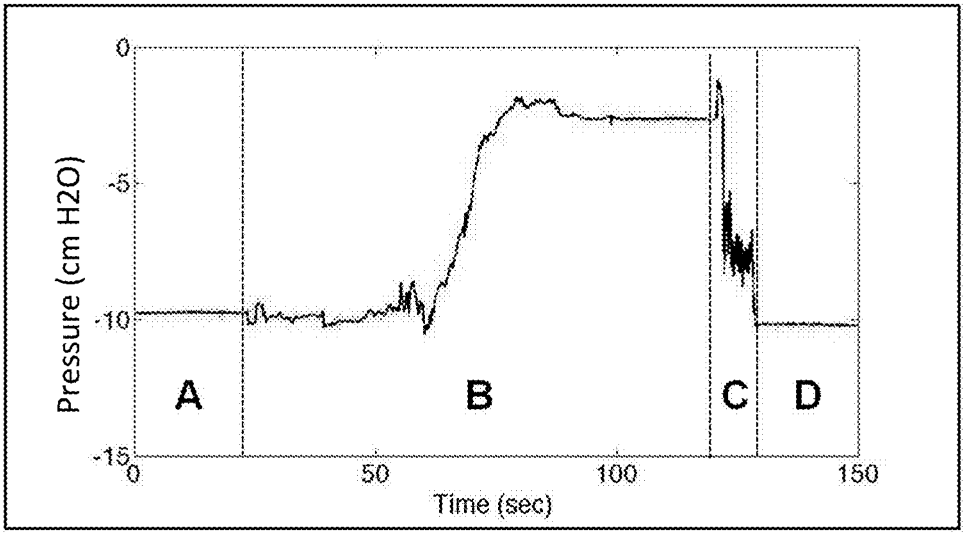
FIG. 8A shows the chest drainage system's ability to detect and clear pooled liquid in the drainage tube.
Figure 8B:
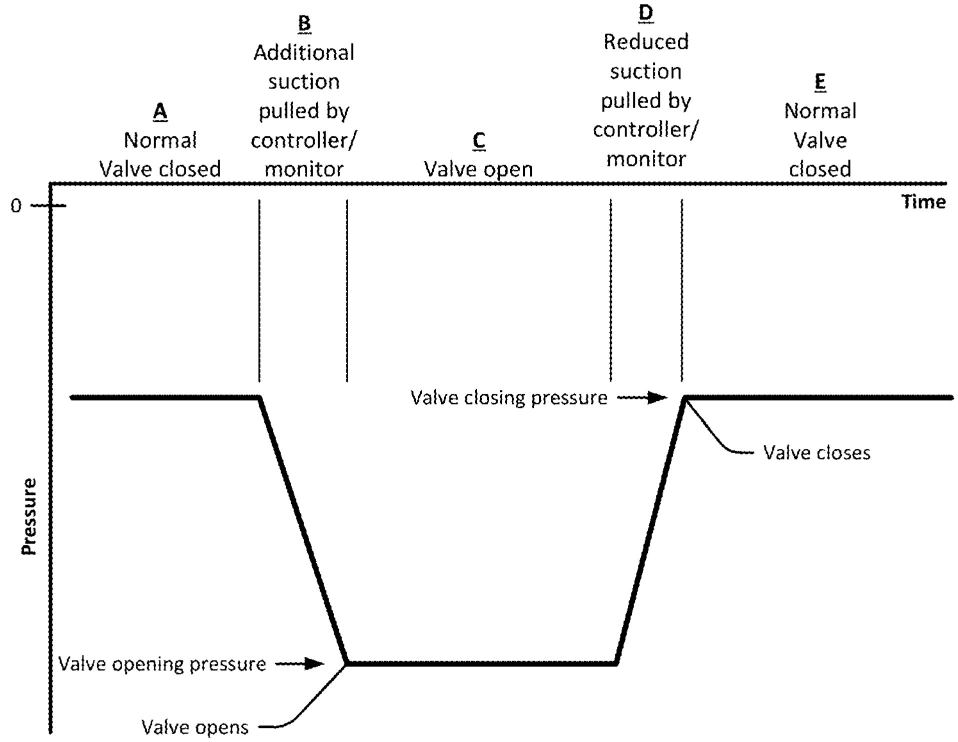
FIGS. 8B-8I show the chest drainage system's ability to detect and clear pooled liquid in the chest tube.
Figure 8C:
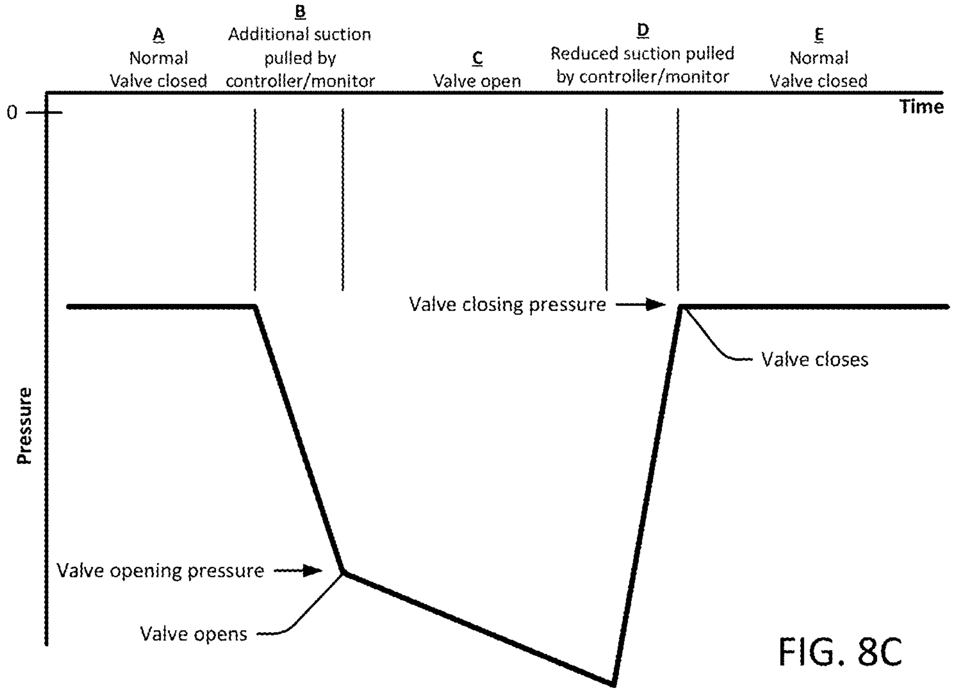
Figure 8D:
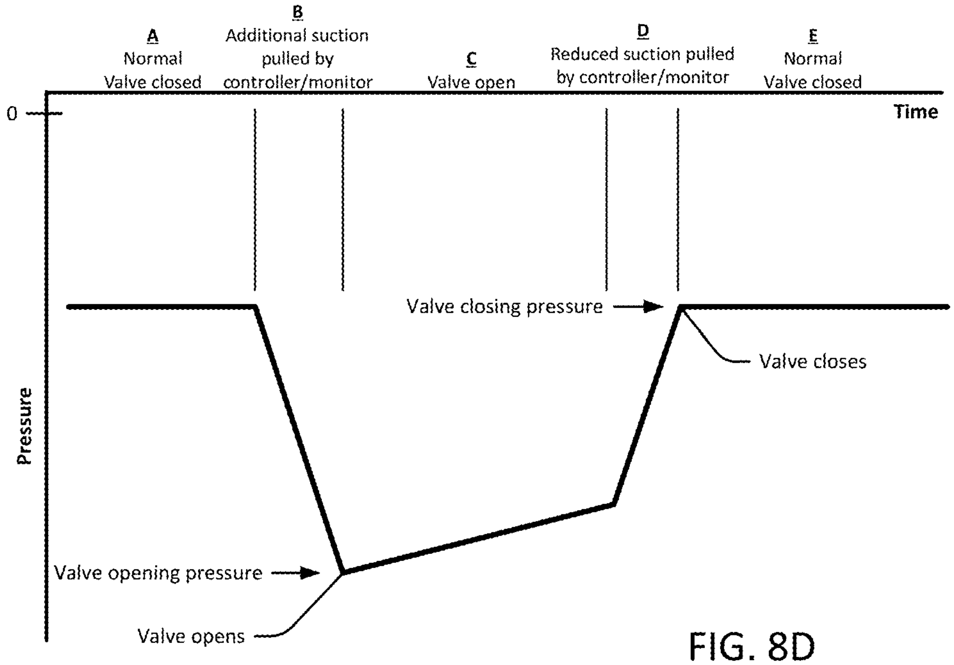
Figure 8E:
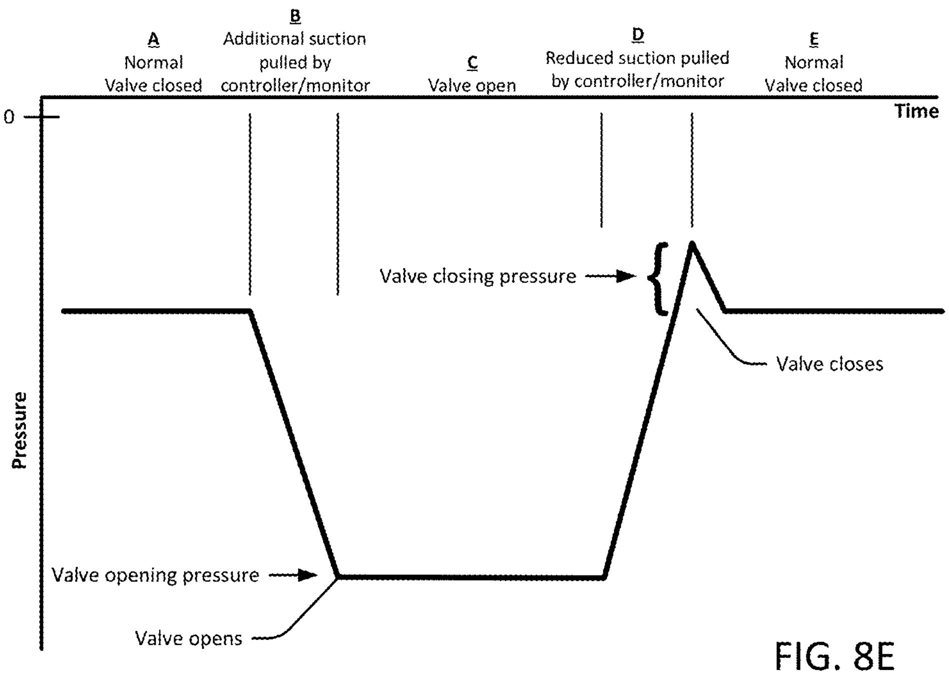
Figure 8F:
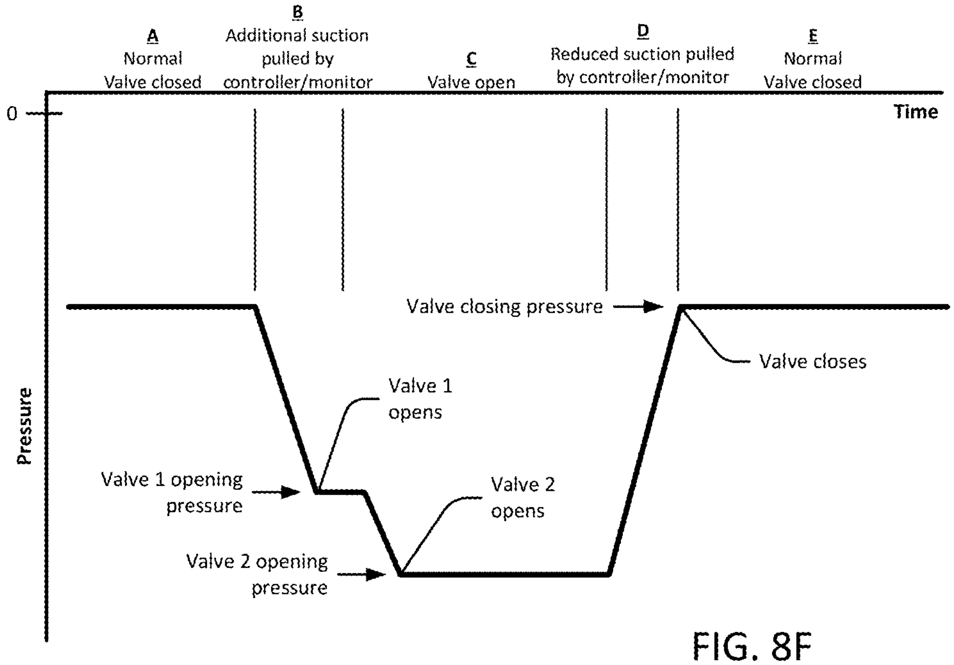

The controller may pull additional suction sufficient for activating/opening multiple chest tube relief valves simultaneously, or in succession, for example as shown in FIG. 8F. In configurations where an OTS chest tube is used with embodiments herein which include a chest tube relief lumen and chest tube relief valve, the controller may only need to supply enough suction to open the chest tube relief lumen valves. In other words, for example, the graph shown in FIG. 8F may apply to any combination of chest tubes which only includes two chest tube relief valves, such as:

P OTS OTS
OTS OTS
P P OTS OTS

Note that in configurations where the chest drainage system is used with one or more OTS chest tubes without a chest tube relief lumen/valve, the drainage lines connected to the OTS chest tubes may still be cleared using devices and methods disclosed herein. In other words, an OTS chest tube may be connected to a drainage line which has a drainage line relief lumen and drainage line relief valve. This system may be used with a single OTS chest tube.

Figure 18:
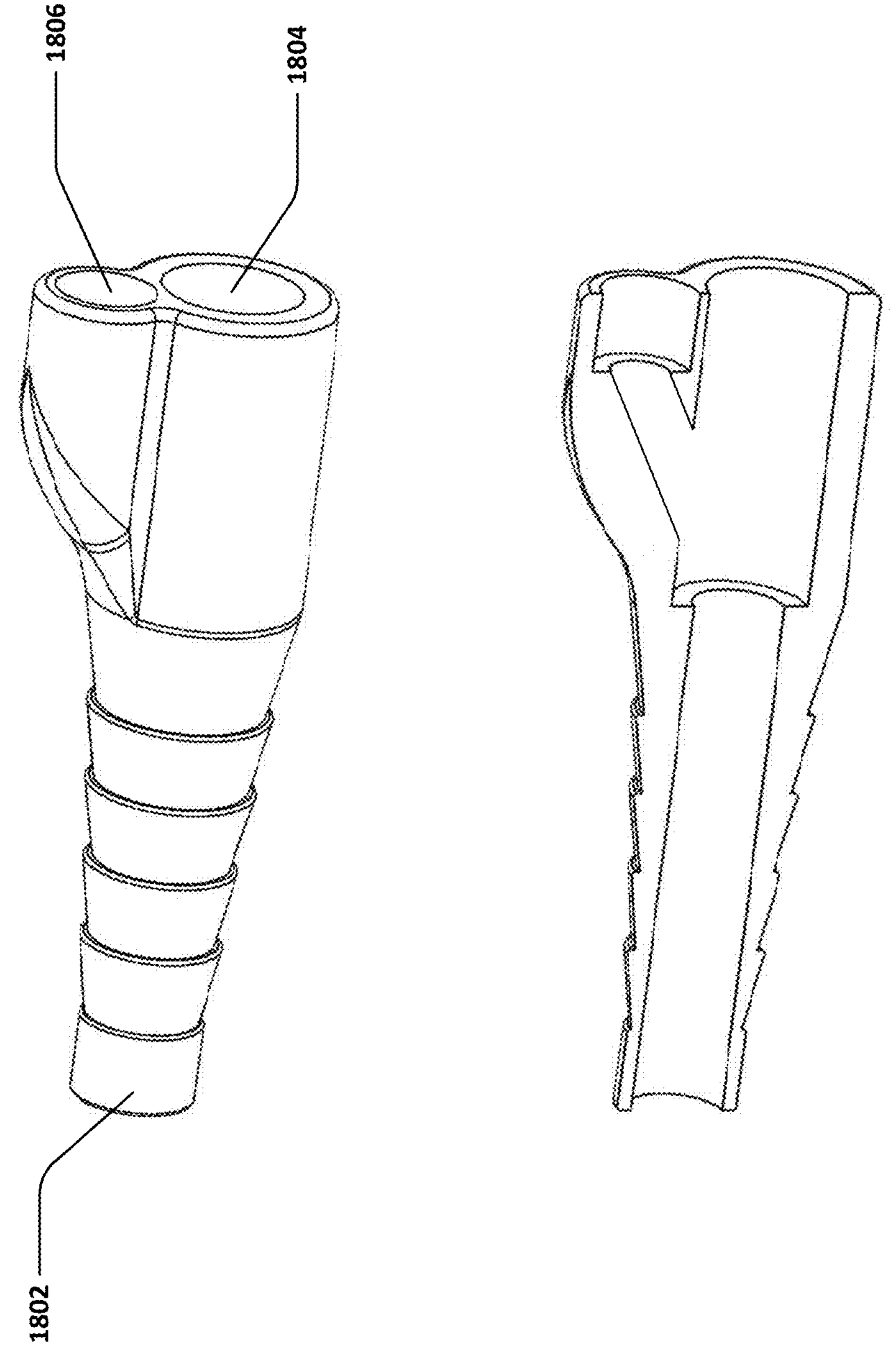
FIG. 18 shows an embodiment of a connection barb.

In embodiments where the chest drainage system is used with a standard OTS chest tube without a chest tube relief lumen, the drainage tube relief lumen and drainage tube lumen may join together at a connection barb between the drainage tube and the chest tube. An example of this type of connection barb is shown in FIG. 18. The connecter includes chest tube connecter 1802, drainage lumen connecter 1804 and drainage lumen relief lumen connecter 1806. This connecter arrangement may be particularly appropriate in thoracic surgery where there is less concern of clogging within the chest tube, and clearance of the drainage line to maintain suction pressure is the primary concern. In some embodiments, the same type of connection barb may be used with a chest tube with a chest tube relief lumen that includes any of the chest tube relief lumen passive valves described herein. In this configuration, the passive valves are normally closed, but the pump in the monitor may generate additional suction at temporal intervals (or when a blockage is sensed) in order to surpass the crack pressure of the valve such that it opens and air can sweep the chest tube drainage lumen clear via air from the chest tube relief lumen. This activation may alternatively or additionally occur when the monitor detects that the magnitude of tidal oscillations has diminished, indicating that a blockage is forming within the chest tube. The controller may also temporarily reduce the suction magnitude after such an activation is performed in order to ensure that the passive valve closes again.

In some embodiments of the chest tube, the distal end of the chest tube may be bifurcated into 2 or more branches to enhance the drainage coverage area of the chest tube, while minimizing the number of insertion sites into the chest. These bifurcated branches may be similar to one another, including but not limited to, number of holes, size of holes, geometry of holes, pattern of holes, length of hole coverage, outer diameter, length and material durometer. Alternatively, each branch may have different properties relative to other branches. For example, a bifurcated chest tube may have two branches at the distal end. One branch may have geometrical features to facilitate evacuation of air from the top of the pleural cavity while the other branch may be optimized for evacuation of pleural fluid from the bottom of the pleural cavity.

In some embodiments of a bifurcated chest tube, any number of the bifurcated branches may have a secondary lumen, i.e. a chest tube relief lumen, capable of chest tube clog clearance.

The bifurcated branches may interface with the primary tube, for example, by an overmold feature. Alternatively, or additionally, a series of smaller branches may be introduced through the primary chest tube and may be extended into the chest cavity via a guide/pull wire.

In some embodiments of the bifurcated chest tube, the bifurcated branches tend to align with one another when the tube is removed from the chest cavity such that the multiple branches easily fit through the hole in the chest through which the primary chest tube has been inserted. This alignment facilitates ease of removal and minimizes patient discomfort.

Tube Blockage Detection and Clearing

FIG. 8A shows the chest drainage system's ability to detect and clear pooled liquid or blockages in the drainage tube. In section 'A', a −10 cmH20 vacuum is properly transmitted to the chest. In section 'B', liquid begins to pool in the drainage tube, resulting in a decreased negative pressure (or an increased pressure) as sensed at or near the tube-tube interface area. If unresolved clinically, drainage would be impeded. However, in section 'C' the drainage tube relief valve is opened and the liquid is flushed into the drainage container, resulting is restoration of proper suction in Section 'D', as well as proper negative pressure as measured. The valve is closed after normal drainage/pressures have been restored. In this example, the pressure is measured at the tube-tube interface area, however pressure may be measured in other and/or additional locations in the system. For example, pressure may be measured at or near the chest or chest tube and also at or near the suction device and/or canister. In some embodiments, the differential pressure measurement may be used to detect flow impediments or pooling or clotting of blood/fluid. For example, in embodiments where the pressure is measured in the collection canister, the measured pressure would get more negative in the presence of a blocked drainage tube.

The controller can identify impediments to fluid drainage via a measured absolute pressure, change in pressure, pressure differential between or among 2 or more locations, or at one location. When an impediment to fluid drainage is identified, an alarm may sound and/or the controller may initiate clearing procedures, including opening and/or closing valve(s) in the chest drainage system, as described elsewhere herein. The negative pressure in the drainage tube may be increased, or changed in other ways, such as pulsed, reversed etc.

For example, if pressure measured at the tube-tube interface area is reading around −10 cmH20 to around −20 cmH20 and the reading changes to zero to −5 cmH20, the controller may open the drainage tube valve to filtered atmospheric air. The controller may leave the valve in this open position for a set period of time, for example, 5-10 seconds or 10-30 seconds and then may return the valve to its regular closed position. Alternatively, the controller may close the valve when a set pressure is measured at the tube-tube interface area or elsewhere. The controller may then check the pressure readings and if they have returned to normal, do nothing more. If they have not returned to normal, indicating a blockage or slowing condition is still present, the controller may repeat the clearing procedure. This may be done repeatedly until the tubing is cleared. Alternatively or additionally, the procedure may change if repeat clearings are necessary. For example, the magnitude of negative pressure used by the suction device to clear the tubing may be increased, and/or the negative pressure may be pulsed. The clearing procedure may be performed in response to the pressure readings and/or it may be done automatically on a periodic basis.

FIGS. 8B-8F shows the chest drainage system's ability to detect a blocked chest tube. FIG. 8B shows the pressure in the chest drainage system over time, as measured at the tube-tube interface. This pressure may be measured by the controller, preferably via the drainage tube relief lumen via sensor 116, but can alternatively be measured elsewhere.

Section A of FIG. 8B shows normal drainage using at a negative pressure created by the suction pump. Section B shows additional suction being pulled by the controller/monitor. This additional suction may be pulled periodically, or may be pulled based on pressure readings in the system. For example, additional suction may be pulled when the presence of tidal oscillations is no longer detected in the drainage system by the controller. The additional suction transfers negative pressure to the drainage tube drainage lumen, the chest tube drainage lumen, and ultimately the chest tube relief lumen and chest tube relief lumen valve. When the pressure differential across the chest tube relief lumen valve reaches the valve opening pressure, the chest tube relief lumen valve opens. The valve may open automatically if the valve is passive, or directly by the controller, if the valve is active. In some embodiments, the valve may be opened manually. Section C shows the pressure when the valve is open. The valve may remain open for a set period of time. Alternatively, the valve may remain open until the controller senses that the clog has been cleared. The negative pressure, or suction, within the system may remain steady during this phase, as shown in FIG. 8B, or the negative pressure may become more negative, as shown in FIG. 8C, or the pressure may become less negative, as shown in FIG. 8D.

Section D shows the magnitude of the negative pressure decreasing as a result of a reduction in suction being pulled by the controller/monitor. When the pressure in the system reaches the valve's set closing pressure, the valve closes (or is closed) and fluid drainage continues in a normal manner. The valve closing pressure may be at a lower magnitude negative pressure than that of the opening pressure, as shown here. The valve closing pressure may be at or near normal drainage negative pressure.

FIGS. 8B-8D show different slopes of negative pressures in different situations. In FIG. 8B the rate at which air is entering the system via the chest tube relief lumen valve is the same as the rate at which the suction pump is draining the system during the open valve section C. In FIG. 8C, the rate of drainage is higher than the rate of air entering the system. In FIG. 8D, the rate of drainage is lower than the rate of air entering the system. The slope of the pressure curve in section C may be controlled by the controller and the amount of suction that it is pulling. The slope may also be reflective of whether a clogged chest tube is being cleared or not being cleared, as is described elsewhere herein.

FIG. 8E shows an embodiment where the controller "overshoots" the normal draining suction pressure to close the chest tube relief lumen valve. The valve closing pressure in this embodiment may be around the normal draining pressure, or it may be at a less negative pressure (lower differential pressure).

FIG. 8F shows an embodiment where there is more than one chest tube. In this embodiment, the first chest tube relief valve opens when the pressure in the system reaches valve 1 opening pressure. It may be necessary to increase the magnitude of the negative pressure in the system further to open the second chest tube relief lumen valve. This is shown as valve 2 opening pressure on the graph. There may be 1, 2, or more valve opening pressures depending on how many chest tubes are used on a single patient. The closing pressures of the multiple chest tube relief valves may be the same, or they may be different. The ability to detect the opening of the valves may be useful to determine whether one or more of the chest tubes is clogged, in which case an alarm or notification may be provided, or the clog may be actively cleared by the system.

Figure 8G:
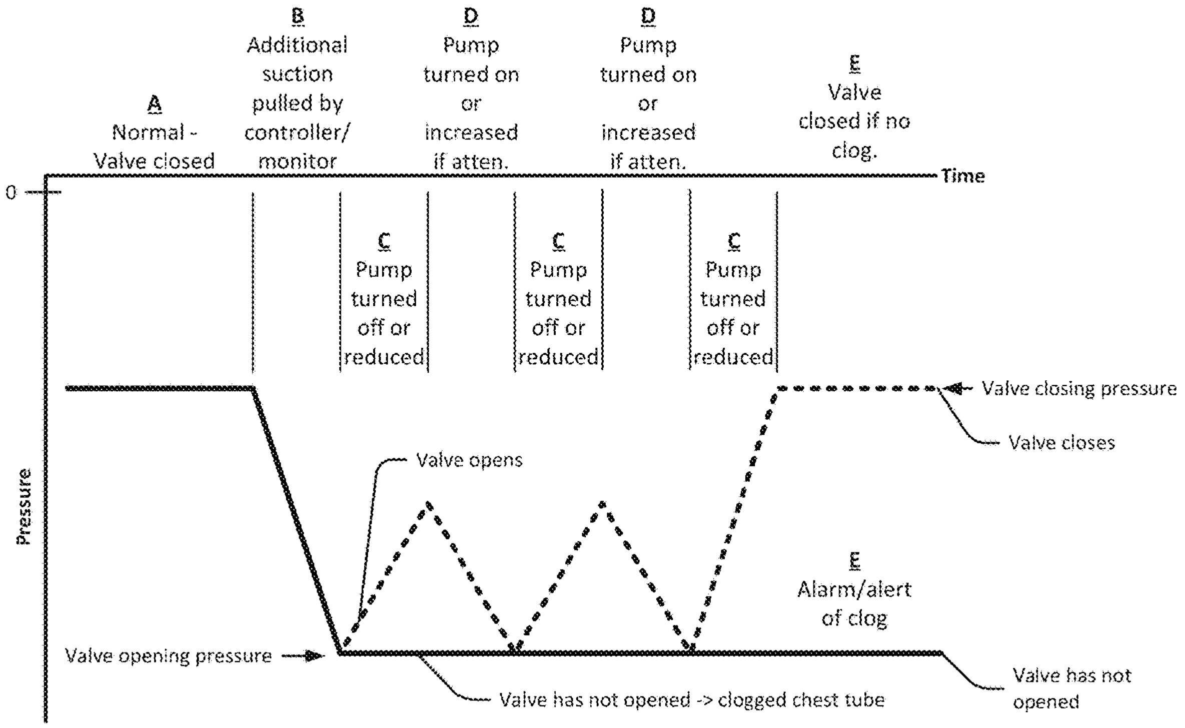

FIG. 8G shows the chest drainage systems ability to detect chest tube clogs using pressure readings. Pressure readings may be taken at or near the tube-tube interface, or at or around the drainage canister, or elsewhere. Pressure readings for this purpose are preferable downstream from the chest, so in the downstream portion of the chest drainage system (shown as a heavy dashed line in FIG. 8H). Section A shows the controller pulling normal drainage level of suction, while the chest tube relief valve is closed. Section B shows additional suction being pulled (more negative pressure being applied) via the canister. The measured pressure becomes more negative. When the suction is near, or above, the chest tube relief valve opening pressure (the pressure differential across the valve is at or near the crack pressure of the valve), the valve may open and the suction may then be reduced by the controller, as shown by the dotted line, as air passes through the chest tube relief lumen, into the chest tube drainage lumen, and through the drainage tube drainage lumen. The dotted line represents a chest tube which is not clogged, or which was clogged, but has been cleared via the increased suction and the opening of the chest tube relief valve. Section C represents the turning off, or reducing, or the suction applied to the chest tube drainage lumen (via the drainage tube drainage lumen).

However, if there is a significant clog in the chest tube, the chest tube relief valve may not open, even with the increased suction. This case is represented by the solid line. The controller of the chest drainage system may increase and reduce the suction multiple times during the clog detection process. Section D shows the pump increasing the suction if suction attenuation has been sensed (i.e., an increase in pressure, or a reduction in suction in the canister or at the tube-tube interface)

If no chest tube clog is present, or if the increased suction level has cleared the chest tube, the suction will attenuate back down to the valve closing pressure after the suction is reduced. This is shown, by the dotted line, in section E. Alternatively, if a chest tube clog remains, the measured suction (negative pressure) will remain relatively un-attenuated, as shown by the solid line, and the controller may trigger an alarm or alert to notify the user that a chest tube clog is still present.

Figure 8I:
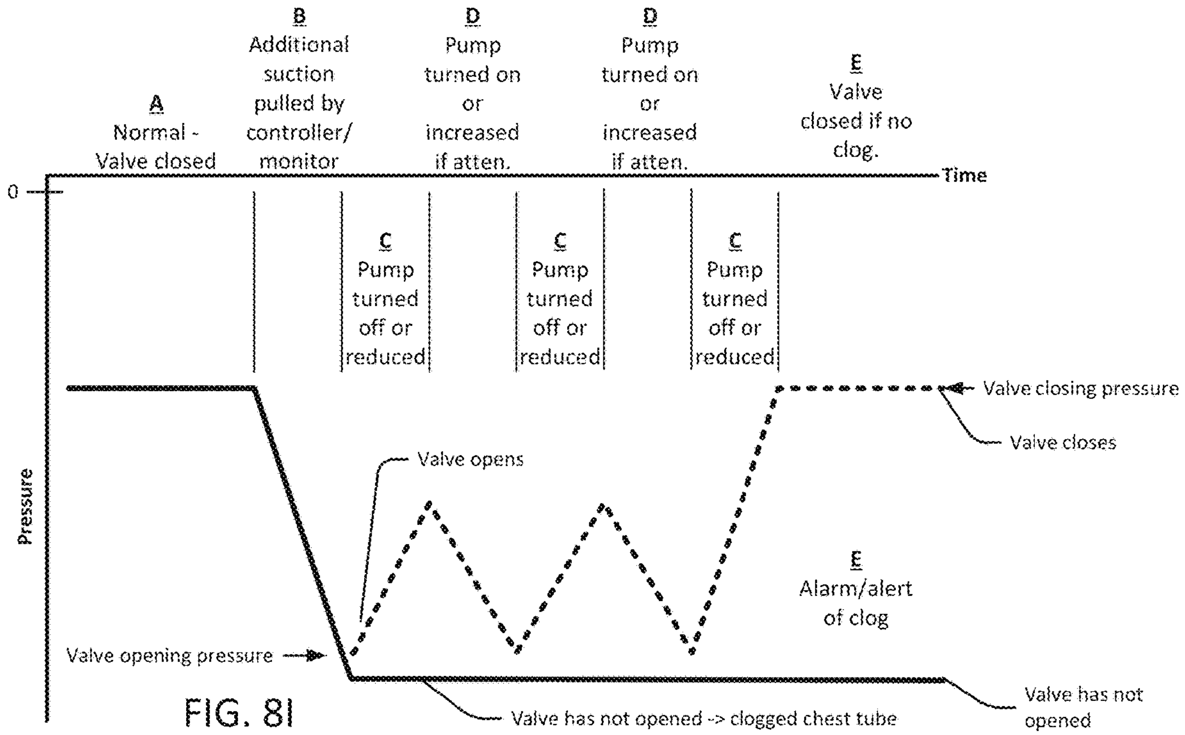
Figure 8H:
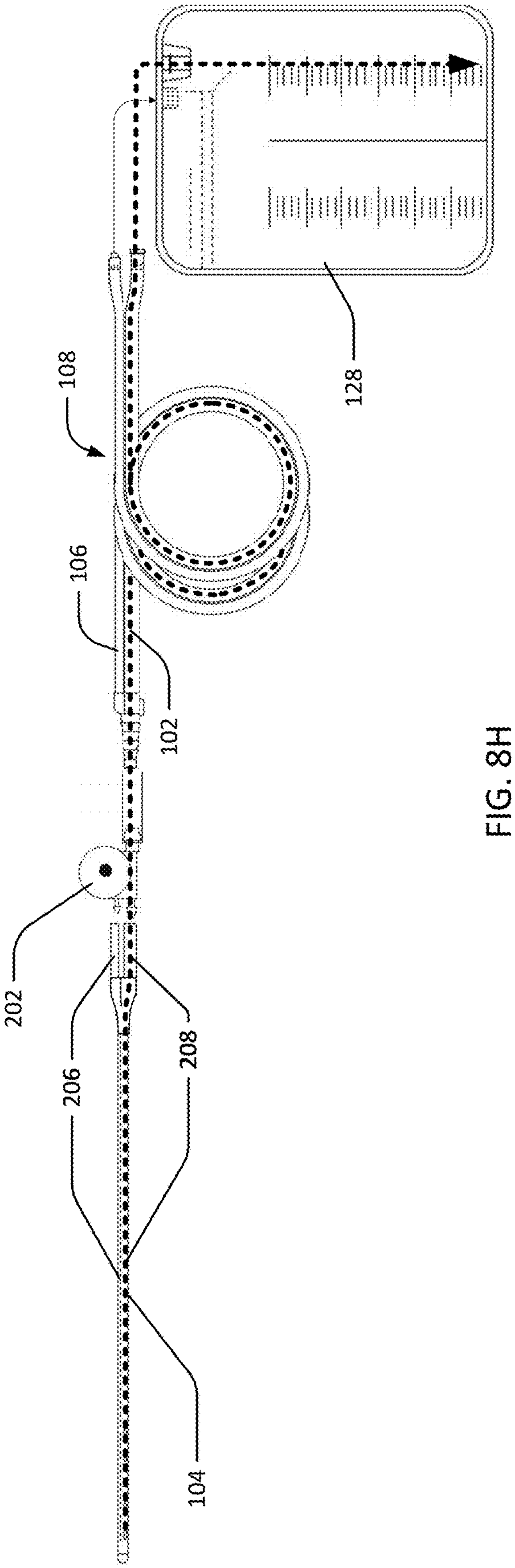
Figure 9:
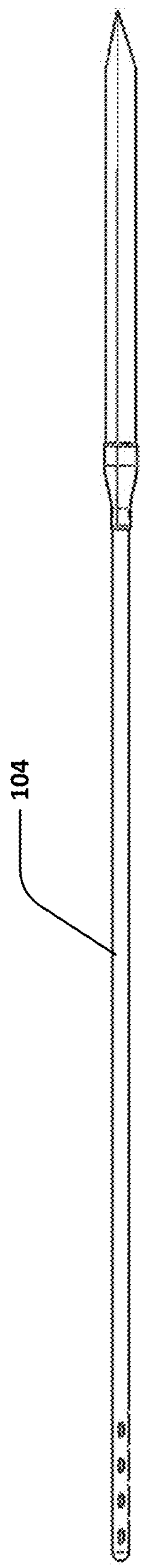
FIGS. 9, 10, 11 and 12 show an embodiment of a dual-lumen chest tube.

FIG. 8I shows pressure readings measured when the chest tube clog detection cycle causes the controller to increase the section level beyond (more negative than) the chest tube relief valve opening pressure.

In some embodiments of the chest drainage system, the chest tube and/or drainage tubing clog detection techniques described herein may be used to confirm the patency of the chest tube prior to removing the tube from the patient. This may be particularly valuable, for example, when the air leak value has diminished to zero or near zero for a prolonged period of time, at which point the system may either automatically or manually activate a drainage tubing and/or chest tube clog clearance cycle in order to confirm patency of the chest tube. In doing so, the system provides confirmation that the cessation of air leak is due to actual physiological healing and not because the tube itself has become obstructed.

In some embodiments, the chest drainage system may include a pH sensor. Post-surgery infection and empyema are of particular concern to clinicians. The pH of fluid drained from the body can be useful in diagnosing these, and other, conditions. To aid in the diagnosis, the chest drainage system may include a pH monitor in the controller, with a sensor in the reservoir, in the tubing, the pump, the valve device, or anywhere in the system. The results may be displayed on the display device. The system may also include a sampling port to sample the fluid drained from the chest. The system may also include an infusion port to infuse an additive into the drainage fluid. These ports may be in the reservoir, tubing, controller, valve device, or elsewhere in the system, for example at the tube-tube interface.

In some embodiments, pH of the drained fluid is measured to monitor for infections. Additional parameters, such as conductance, spectroscopic signatures, protein content, and specific gravity of the drained fluid may also be measured to monitor patient recovery. Any of these measurements may be one time measurements or measurements made over time. For measurements made and collected over time, the controller may analyze these data for trends. These data may be integrated with the hospital's electronic medical record system (either communicated to, or data may be obtained from) and/or displayed on a screen on the device or on a connected monitor, which may be connected either by wire or wirelessly. In some embodiments, alarms or notifications may be activated by the controller when the parameters surpass certain thresholds, which may be preset or set by the user. These may be visual and/or audible alarms or notifications. These data may also provide input to the line-purging and clog-clearing functions of the device, such that, for example, line purging is activated when the suction at the chest drops below a certain level, or clog clearing is activated when tidal oscillations are diminished.

Figure 10:
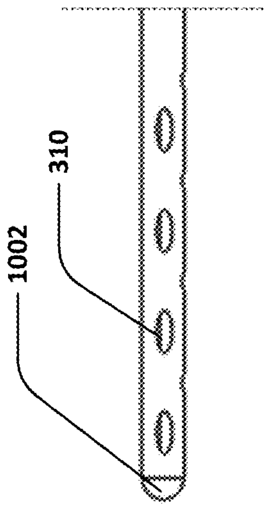
Figure 11:
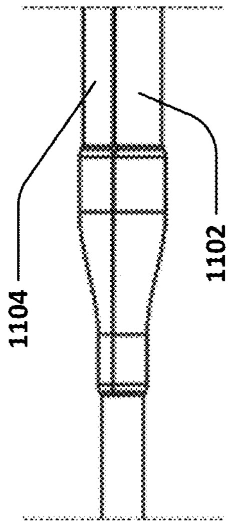
Figure 12:
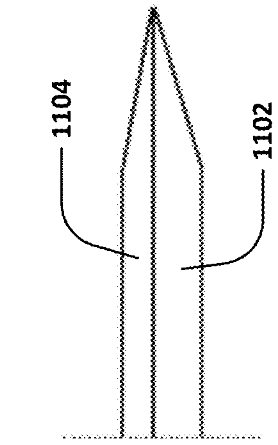

FIGS. 9, 10, 11 and 12 show an embodiment of a dual-lumen chest tube. Chest tube 104 may be made using silicone, PVC, or other suitable material with a suitable durometer, for example 20 A-80 A. The effective outer diameter of the chest tube may vary between 8 Fr-40 Fr. For example, chest tube sizes may include 15 Fr., 19 Fr., 23 Fr., 27 Fr., etc. The chest tube shown in FIG. 9 may include three sections: a chest tube region, as shown in FIG. 10, a transition region, as shown in FIG. 11, and a pull-through region, as shown in FIG. 12. The chest tube region comprises a dual-lumen extrusion with holes 310 near the patient side for drainage of fluid from the body. The chest tube region is preferably capped with rounded tip 1002, but may also have an open patient end without a cap. The transition region separates the two chest tube lumens, for example chest tube drainage lumen and the chest tube relief lumen, into separate tube sections that are more easily attached to barbed connectors.

Figure 13:
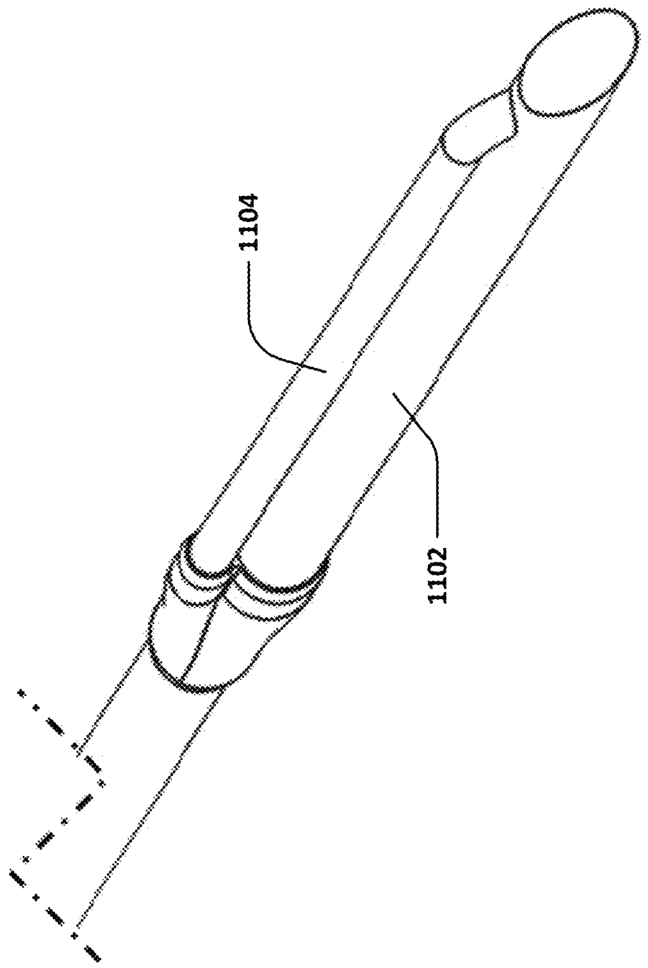
FIG. 13 shows an embodiment of a dual lumen chest tube.

FIG. 11 shows chest tube drainage lumen tube section 1102 and chest tube relief lumen tube section 1104. Specifically, at the non-patient end of the transition region, both lumen preferably become circular to allow for proper attachment to standard barbs. The pull-through region shown in FIG. 12 includes chest tube drainage lumen tube section 1102 and chest tube relief lumen tube section 1104. The two tube sections may also be joined, for example with webbing or adhesive. The ends of the two tubes may be tapered to allow for easier insertion into the chest and also easier pulling of the chest tube through, from the inside to the outside, the chest wall. Alternatively, the tubes may not be tapered or only one of the tubes may be tapered. In some embodiments, the relief lumen tube may "dive" into the larger tube so the outer profile on the non-patient end is just that of the drainage tube. This is shown in FIG. 13. The relief tube is also preferably sealed near the non-patient end, for example with a plug of silicone, in order to prevent fluid ingress into the relief lumen as the tube is pulled through the patient wall.

Chest Tube Clog Detection Methodology

In some embodiments of the system, the controller monitors the pressure within the drainage lumen of the system, at the barb, canister, or elsewhere. The controller may monitor the rate of change of the pressure as the suction level is changed. If the rate of change in pressure indicates a clog or flow restriction in the system, the controller may issue an alert, alarm or display information relating to the obstruction and also possibly the location of the obstruction. The controller of the system may automatically attempt clog clearing mechanisms, which may be specific to the sensed location of the obstruction. Alternatively, the obstruction clearing sequences may be initiated manually.

In some embodiments of the chest tube, the chest tube may incorporate two or more electrodes, either along its length, or otherwise. The controller may sense the continuity between electrodes, caused by liquid, or other material, and may issue an alarm, or attempt alternative measures of clearing the chest tube if the controller senses electrode continuity for longer than a set period of time, indicative of chest tube obstruction. Similarly, the drainage tube may include electrodes.

In some embodiments of the device the controller monitors the pressure (i.e. suction) vs. flow rate of the system. The range of the pressure vs. flow rate of the system is known for on unobstructed chest tube. The controller senses changes in pressure vs. flow characteristics and may issue an alarm, and/or attempt measures of clearing the chest tube when the controller determines the pressure vs. flow rate is outside of the unobstructed range.

In some embodiments of the device, a visual indicator may reflect the flow of air through the relief lumen into the chest tube. The indicator may show when air is flowing through the relief lumen, and/or may show when air is not flowing through the relief lumen. This indicator may take the form of an in-line impeller/propeller/fan, which spins in the presence of airflow and is otherwise stationary. In this manner, the user can easily detect when air is flowing through the relief lumen by viewing the indicator. In some embodiments, this indicator may be audible instead of or in addition to the visual indicator. In some embodiments, the audible indicator takes the form of a whistle that generates sound when air is flowing through it and is otherwise silent. In this manner, the user can easily detect when air is flowing through the relief lumen by listening to the indicator. The drainage relief line may be monitored similarly.

In some embodiments, the indicator comprises a duckbill or similar valve, such that in the presence of airflow the valve is kept open. The valve further has electrical contacts, such as electrodes, within the flaps/seals, such that these contacts connect to one another when the valve is fully closed. The electrical contacts are further connected via the controller to an electrical visual or audible indicator, such as an LED or buzzer, respectively, such that when the contacts make contact a circuit is closed and the indicator changes status. In this manner, the indicator is activated when the valve is closed and no airflow is present, for example the LED becomes lit or the buzzer sounds, such that the user can easily detect when there is no air flowing through the relief lumen.

In some embodiments, the controller receives signals from one or more sensors (may be digital or analog) measures or indicates pressure within the chest tube at a specific point or at various points along the length of the chest tube. The controller may display or sound an alert when the pressure in the chest tube changes by a predetermined magnitude. This change in pressure may be indicative of fluid buildup inside or outside of the chest tube or an alteration of the patient's physiological parameters. The controller may initiate some automatic functions instead of or in addition to the alert/display, based on the change in pressure. The drainage line may be monitored similarly.

In some embodiments, the chest tube includes multiple openings between the relief and drainage lumens along the length of the tube. These openings fluidly connect the two lumens along the length of the tube. These openings may be used to determine the presence and/or location of fluid and obstructions. For example, the controller may increase suction within the system and receive input from a sensor or sensors measuring a parameter (i.e. pressure, air flow rate, etc.). This parameter info may provide information regarding the length and/or location of an obstruction within the chest tube, for example, whether the obstruction is located in the distal end, middle, or proximal end of the chest tube.

Chest Tube Clearance Methodology

Figure 43:
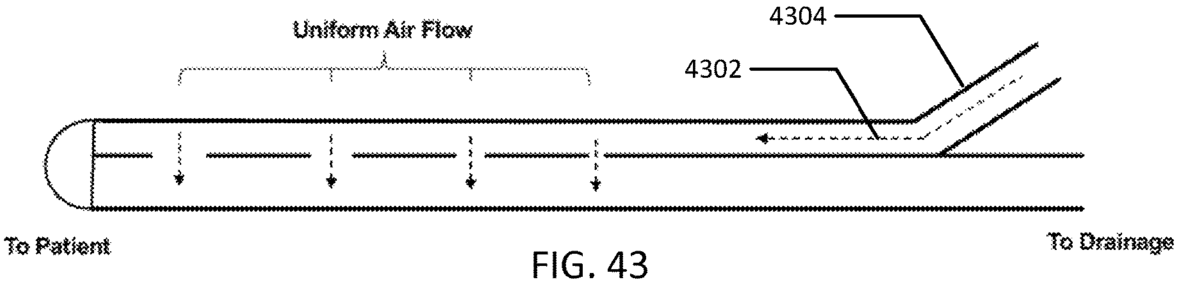
FIG. 43 shows an embodiment of a chest tube with multiple openings.

In some embodiments, the chest tube includes multiple openings between the relief and drainage lumens along the length of the tube, where the openings are larger near the distal end and increasingly smaller towards the proximal end, shown in FIG. 43. The variation in connection opening size is determined such that the flow rate through each hole during a chest tube clearance cycle is approximately equivalent, and provides air flow 4302 from relief lumen 4304, along the entire length of the chest tube and promote drainage. In some embodiments, the openings may be of similar size to one another.

In some embodiments, the chest tube incorporates a rotational mechanism that can be rotated manually or automatically, continually or intermittently, by the controller of the system to open or close the connection opening(s) between the relief and drainage lumens. The rotational mechanism may be rotated to move an auger-like component to facilitate movement of any obstructions within the tube via mechanical motion.

Figure 44:
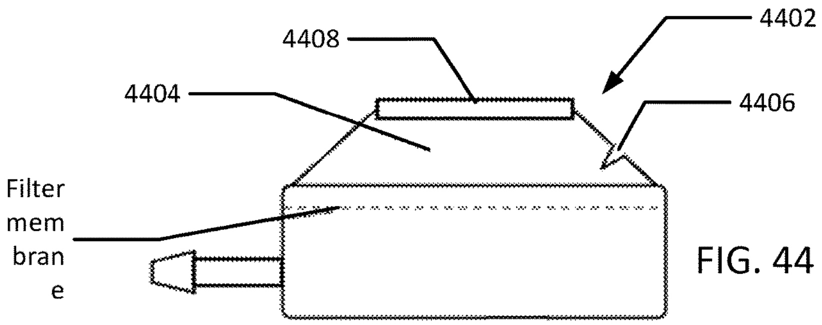
FIGS. 44-46 shows a forced fluid mechanism.
Figure 45:
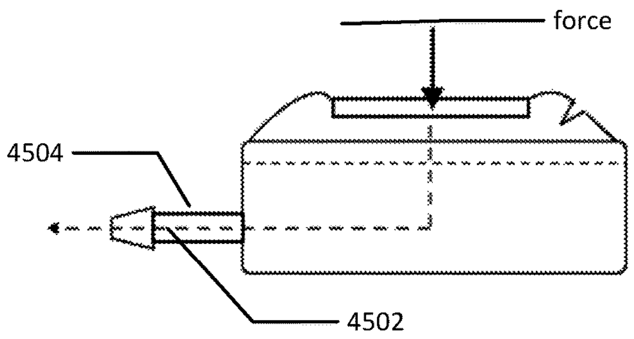
Figure 46:
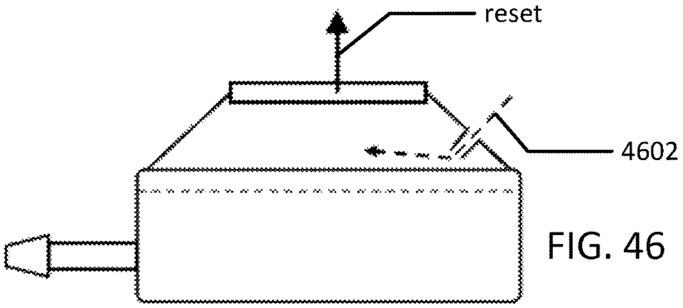

In the embodiment shown in FIGS. 44-46, chest tube relief valve 4402 incorporates a mechanism for manually or automatically forcing air into the relief lumen of the chest tube to push fluid and/or obstructions into the drainage lumen. This mechanism may include bladder 4404, in some embodiments biased toward open, such as with a spring. This mechanism may include one or more one-way valve(s) 4406 to control the flow of air during operation. When used manually, the user presses on surface 4408, as shown in FIG. 45, to force air 4502 through adapter 4504 into the relief lumen of the chest tube. When the force on surface 4408 is released, the bladder again expands, allowing air 4602 to be pulled through one-way valve 4406 which fills the bladder. In this manner, a user may manually force air into the relief lumen of the chest tube to remove an obstruction in the chest tube. Alternatively, this mechanism may be automatically controlled by the controller and enacted when a negative event is occurring (i.e. reduced air flow, or pressure changes, detected which result from an obstruction in the drainage lumen of the chest tube and/or drainage line).

In some embodiments, the chest tube relief valve has a port for receiving a container of fluid, which may be a liquid (i.e. Saline), which is used to flush the chest tube via the chest tube relief lumen, for example, in the event that an obstruction in the chest tube is detected. In some embodiments of the device, the flushing action may be performed manually. Alternatively or additionally, the controller may control the introduction of controlled amounts of flushing fluid into the chest tube via the chest tube relief lumen. The control module may factor the fluid volume introduced into the chest fluid drainage calculations, by subtracting from the output volumes the volume of fluid introduced for flushing purposes. Similarly, liquid may be use to clear the drainage line.

In some embodiments, the controller may apply a non-steady suction to the chest tube via the drainage line. The non-steady suction may include repetitive negative pressure, alternating with a less negative pressure, zero pressure, or a positive pressure. The magnitudes of the suction oscillations may be steady or may alter, for example, increasing in magnitude over time. The period of the suction oscillations may be steady, or may change over time. The oscillations, or fluctuations, in suction may be of any number and may be a fixed number. This sequence may occur automatically, when certain parameters are met indicating a chest tube blockage, or may be initiated manually via the controller (for example, by pressing a button).

In some embodiments, the frequency and duration of the clog clearance cycle is adaptive, for example, to activate more frequently and/or at a higher suction level when clogging is more likely or fluid output is higher and less frequently when the risk of chest tube clogging has diminished. The learning to inform this adaptation may use data from a single patient, or data from multiple patients.

In some embodiments, the controller receives, from a pressure sensor, the rate of pressure decay caused by air entering the system during a clog clearance cycle and may adjust the clog clearing cycle frequency, duration, and/or suction level accordingly to maintain an optimum pressure profile.

In some embodiments, the clog clearance functionality can be activated in varying degrees, such as but not limited to: On, Intermittent, or Continuous.

Pleural Assessment Display

Figure 39:
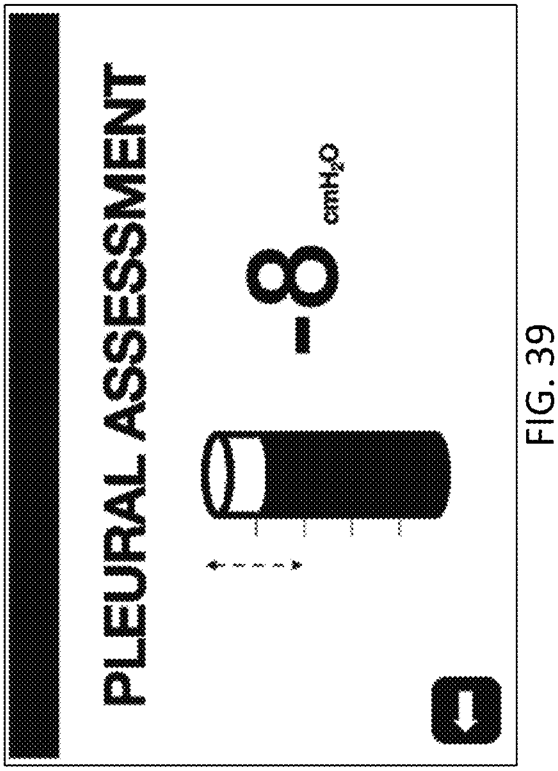
FIGS. 39-42 show various possible display options for pleural assessment.
Figure 40:
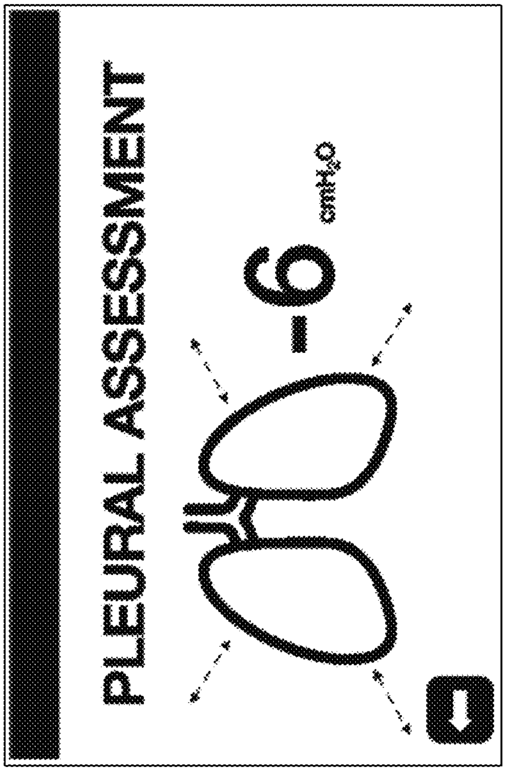

In some embodiments of the device, the user may monitor for patency of the tubing in the system (drainage tubing and/or chest tube) by viewing changes in pressure indicative of oscillations in pleural pressure, due to patient breathing, which may be displayed by the controller of the system. The controller may display the measured pressure numerically, which increases and decreases as the patient breathes. Alternatively, the display may be graphical, showing movement of an indicator as the pressure changes, for example a ball or water column that rises and falls as the pressure increases and decreases, as shown in FIG. 39. Or, alternatively, lung icons that expand and contract may be displayed, as shown in FIG. 40. An ongoing indicator of patient breathing allows the user to confirm that the chest tube and drainage lumen are unobstructed. The user may have greater confidence in the drainage volume values, air leak values, and other indicators as a result.

In some embodiments of the system, the user (for example a nurse or physician) may perform a challenge of the patient's air leak by, for example having the patient breathe normally, having the patient breathe deeply, having the patient cough, and/or having the patient perform a Valsalva maneuver. The controller may monitor the pressure within the drainage lumen, via the canister. A pressure threshold may be stored in the memory of the controller, either having been entered by the user, or otherwise. This threshold may be different for different patients/challenges etc. The controller may create an alert, or display, alerting the user when the pressure within the drainage lumen exceeds a threshold pressure during a challenge. The threshold values may be stored in the controller, which may automatically indicates whether the threshold has been exceeded. Alternative, the user may also manually monitor for such an increase above a threshold. The threshold used may, for example, be dependent on the set suction level of the system and/or other parameters, or alternatively be a fixed value, for example 0 cmH2O or +2 cmH2O.

Figure 41:
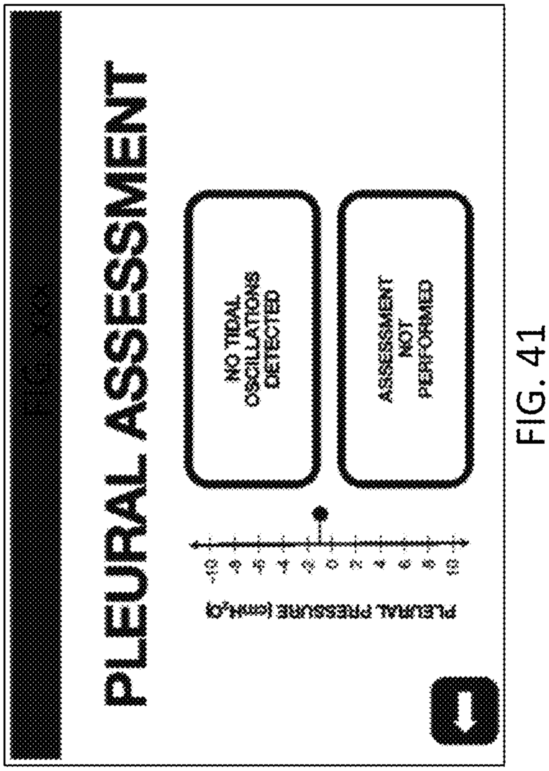
Figure 42:
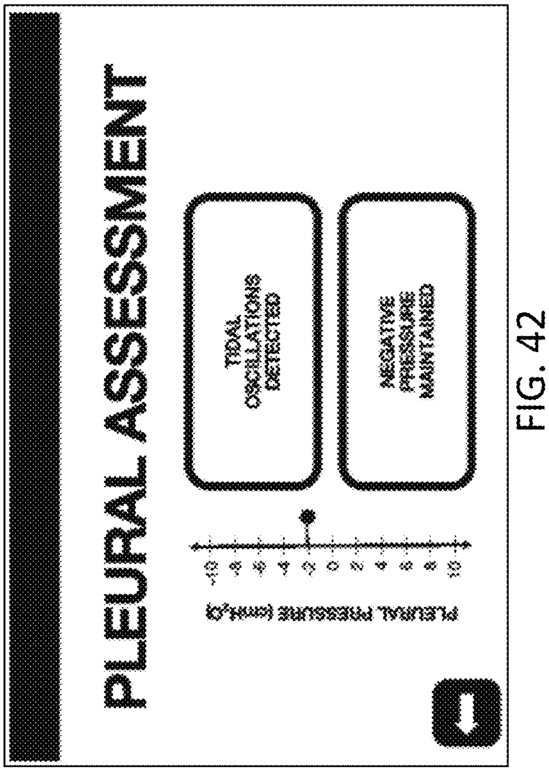

FIGS. 41 and 42 show alternative pleural assessment displays, including the presence or lack of presence of pressure oscillations related to breathing, and/or other information, for example challenge results.

Air Leak

In some embodiments, the system is capable of measuring the flow rate of air evacuated from the canister/reservoir, in addition to pressure in the canister and pressure in the drainage tube relief lumen. Evacuation flow rate may be used to determine the presence and rate of an air leak from the chest cavity. The evacuation flow rate necessary to maintain the system at the prescribed suction level is equivalent to the flow rate of air entering the system (air leak), as the flows of air into and out of the system must be equal in the presence of steady pressure. Evacuation flow rate may be determined by the flow rate of the air being evacuated from the canister via the integrated suction pump and the volume of liquid in the canister. These parameters may be tracked over time by the controller to determine chest air leak presence and other parameters, such as air leak rate and changes to the air leak rate over time. Flow rate measurements can be made with any number of off-the-shelf sensitive air flow sensors that are known in the art. Flow rate may alternatively or additionally be measured by measuring the revolutions of the pump motor necessary to keep the suction at a prescribed level via a tachometer.

To determine the air leak rate within the system, the may utilize the pump tachometer to count the rotations that the pump is undertaking in creating the suction within the system. The rotation number, as well as pressure measurements and time measurements may be used to identify and quantify air leaks. The quantification of air leak rate to milliliters per minute may be achieved by the controller by using a transfer function to convert pump revolutions per minute (RPM), and canister pressure, to milliliters per "tick" of the pump rotation counter. This transfer function may depend on the suction level of the system and the speed of the pump. The number of "ticks" may then be multiplied by the milliliters per "tick" metric (based on the current RPM and pressure) and divided by the time over which the "ticks" occurred, resulting in an average air leak rate in milliliters per minute. In some embodiments, a mean and/or median air leak rate is determined.

In some embodiments, the volume and/or flow rate of an air leak (from the patient's lung) is measured to monitor wound healing.

Air Leak Display

In some embodiments of the air leak display, the user may toggle between various methods for displaying air leak information, including but not limited to, air leak rate in mL/minute, a graphic that displays general information about the presence or lack of an active air leak, a digital "bubble" icon, or historical data. In some embodiments of the air leak display, should the air leak read a value of 0 mL/min, or near 0 mL/min, continually for a predetermined period of time (ex. 60-minutes), the system will automatically attempt to verify chest tube patency, through the activation of a clog clearance cycle (if active), a passive measurement of pressure change similar to a pleural assessment, other pressure sensor readings or changes, drainage volume measurements, or present a visible or audible signal to the user to suggest the patient perform a pleural assessment breathing event such as cough. This monitoring may be used in conjunction with, or separately from, a mL/min air leak threshold set point. This information may be utilized by the controller, to provide guidance for removal of a chest tube. This guidance may be in the form of information displayed on the screen including a confidence level. In some embodiments, this info is input into the controller by a clinician/user.

In some embodiments of the device, the system may quantify air leak values into categories, for example but not limited to, air leak rates between 10-50 mL/min will display "LOW", etc. This quantification may or may not account for patient characteristics such as BMI, pre-procedural lung volume, respiratory conditions (ex. COPD), other factors which may affect the classification of air leak readings from patient to patient. Some embodiments of the system allow the user to input info such as BMI, patient weight, lung volume, relevant conditions, and other factors. Some embodiments of the controller are connected with the electronic medical or health record and may automatically obtain these, and other, factors.

In some embodiments of the device the system may monitor spirometry data. The system may monitor the patient's pleural pressure to determine and store expiratory forced vital capacity (FVC) and forced expiratory volume in one second (FEV1), as well as calculate the FEV1/FVC ratio. The controller may utilize patient data to predict normal values and indicate/display the outcome of a spirometry test.

In some embodiments of the device the system provides the minimum amount of suction to prevent the development of a pneumothorax. In this embodiment of the device the system may provide no active suction while it is monitoring the changes in pressures within the pleural space. In this embodiment the system monitors changes in peak-to-peak pleural pressures during normal breathing. This embodiment of the system may recognize decreases in peak-to-peak pressures which may indicate the development of a pneumothorax, and provide suction to return the peak-to-peak pressures of the pleural space to the pre-pneumothorax values. In this embodiment, the system may continue to increase suction as necessary to obtain the desired peak-to-peak pressures of the pleural space. The system may return to no active suction when the management of pneumothorax become unresolved at lower levels of suction, and may issue an alert or display to inform the user of a potential pneumothorax.

Tight Drainage Pressure Control

Some embodiments of the drainage system include logic incorporated into the controller which controls various components of the system in an effort to maintain the pressure experienced by the patient at the drainage site as close to zero, or as close to a target pressure, as possible. By monitoring pressure close to the chest, and adjusting the applied pressure and controlling the drainage tube relief valve, the controller can maintain the pressure at the chest of the patient at a target pressure, for example zero. In this manner, the system functions as a one-way valve that prevents the accumulation of positive pressure, while allowing for some acceptable amount of patient-generated negative pressure to accumulate within a normal physiologic range.

Figure 47:
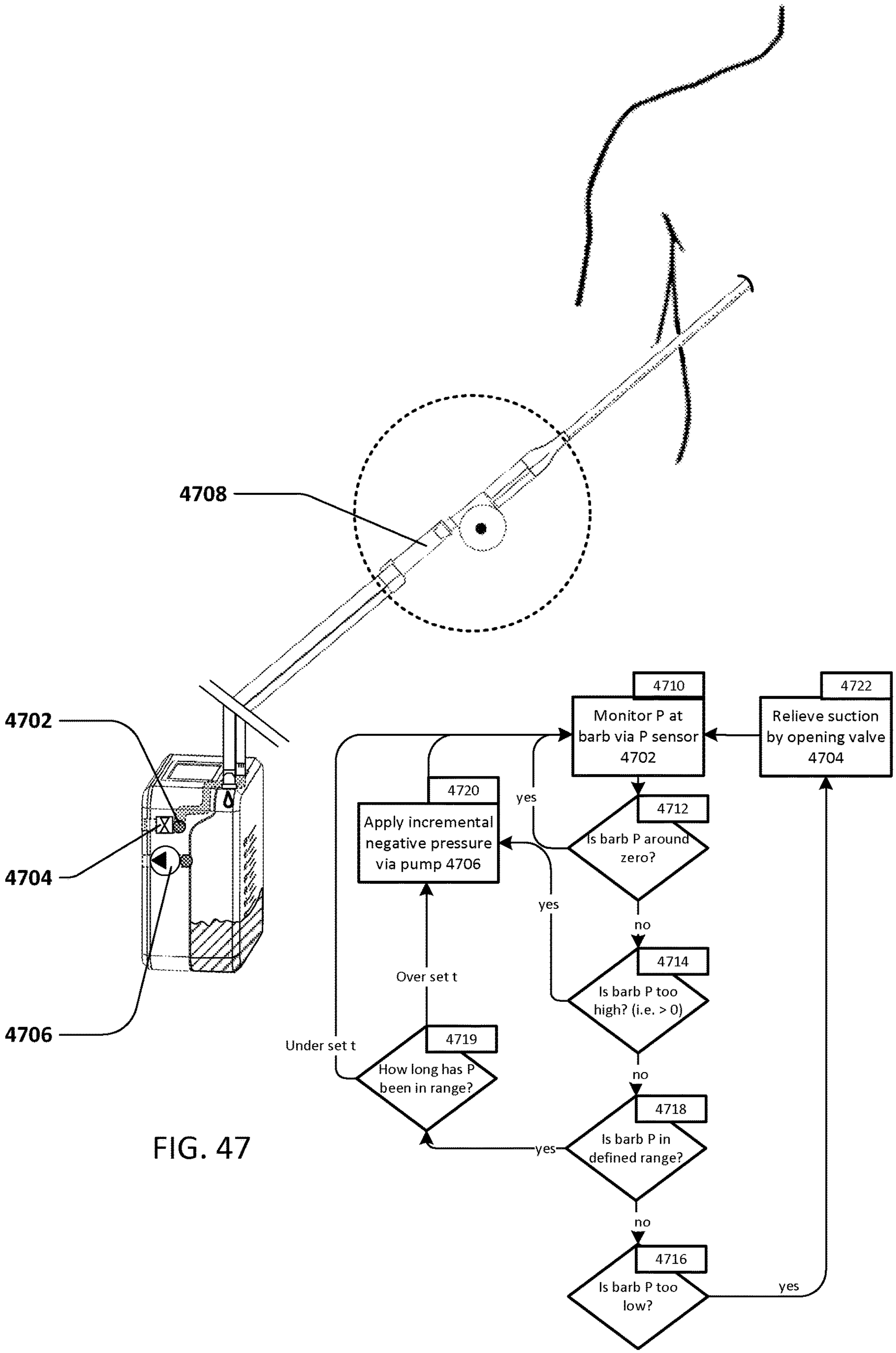
FIG. 47 shows the flow of logic that the controller may follow to control the pressure applied to the chest of the patient.

FIG. 47 shows the flow of logic that the controller may follow to control the pressure applied to the chest of the patient. The controller monitors the pressure at barb area 4708 via pressure sensor 4702 in the controller/monitor. This is represented by box 4710. The controller monitors this pressure with the goal of maintaining it as close to zero as possible. It is also possible that the controller may maintain the pressure at barb area 4708 at another pressure, either positive or negative, but for this example, we will use zero pressure as the maintenance goal. It is also possible to monitor the pressure at other locations, for example, in the chest tube, in the chest tube relief lumen, in the chest, etc.

Decision box 4712 is triggered by the pressure monitored at barb area 4708. If the pressure is around zero (allowing for some slight variance, such as between 0 and −10 cmH20), the controller continues to monitor the pressure. If the pressure is not around zero, the controller determines whether the pressure is too high, i.e. above zero, as represented by decision box 4714, or too low, i.e. below zero, as represented by decision box 4714. If the pressure is too high, the controller will instruct pump 4706 to apply negative pressure to bring the pressure back into the desired range. This is represented by box 4720.

If the measured pressure is not too high, i.e. not above zero, then the controller checks to see if the pressure is within a defined adjacent range, for example, between 0 cmH20 and −0.5 cmH20. This is represented by decision box 4718. If the pressure is within the defined range, the controller then checks how long the pressure has been within the defined range. This is represented by decision box 4719.

If the pressure has been within the defined range for longer than a set period of time, for example, 10 seconds, the controller will instruct pump 4706 to apply incremental negative pressure as represented by box 4720.

If the measured pressure has been in the defined range for less than the set period of time, the controller continues to monitor the pressure without activating pump 4706. This is to allow for some short variations in pressure due to the patient breathing. The time period criterion prevents the pump from activating simply because of pressure variations caused by the patient breathing.

If the monitored pressure is too low, for example below −10 cmH20, at decision point 4716, then the controller will open valve 4704 to atmosphere to reduce the negative pressure within the system, via the drainage tube relief lumen. The valve will remain open until the target pressure close to 0 cmH2O has been reached, for example −0.5 cmH2O or −1 cmH2O. This is represented by box 4722. The controller will then close valve 4704.

In some embodiments, pump 4706 is activated (represented by box 4720) when the pressure measured at barb area 4708 by pressure sensor 4702 is measured above 0 cmH20 or is between 0 cmH20 and −0.5 cmH20 for greater than 10 seconds, and valve 4704 is opened when the pressure measured at barb area 4708 is measured below −0.5 cmH20.

In some embodiments, pump 4706 is activated (represented by box 4720) when the pressure measured at barb area 4708 by pressure sensor 4702 is measured above 2 cmH20.

In some embodiments, pump 4706 is activated (represented by box 4720) when the pressure measured at barb area 4708 by pressure sensor 4702 is measured above 1 cmH20.

In some embodiments, pump 4706 is activated (represented by box 4720) when the pressure measured at barb area 4708 by pressure sensor 4702 is measured above 0 cmH20.

In some embodiments, valve 4704 is opened when the pressure measured at barb area 4708 is measured below −5 cmH20.

In some embodiments, valve 4704 is opened when the pressure measured at barb area 4708 is measured below −10 cmH20.

In some embodiments, valve 4704 is opened when the pressure measured at barb area 4708 is measured below −20 cmH20.

In some embodiments, the negative pressure cutoff is 0 cmH20, −2 cmH20, −5 cmH20, −10 cmH20, −20 cmH20, −100 cmH20.

Some embodiments include a mechanical positive pressure relief valve in the system to provide a maximum positive pressure within the system. For example, a positive pressure relief valve may be used instead of, or in addition to, applying suction to the drainage lumen to reduce positive pressure within the drainage lumen. In some embodiments, the positive pressure is reduce when the pressure is measured above 0 cmH20, +2 cmH20, +5 cmH20, +10 cmH20, +20 cmH20, +100 cmH20.

In some embodiments, the positive pressure threshold and/or the negative pressure threshold is selected by the user.

Drained Fluid Volume Measurement

Collected fluid (either gas, liquid, or both) volume and/or flow rate measurements may be made over time, and the data stored and/or displayed and/or shared with other systems. The volume measurements may be made with a non-contact capacitive sensor, but may alternatively be made with optical sensors, pressure sensors, acoustic (such as ultrasonic) sensors, or any other liquid level sensing methods known in the art.

To determine the drainage fluid volume collected in the drainage canister, the controller may utilize a built-in capacitive level sensor that senses changes in capacitance between two electrodes as the height of fluid in the drainage canister changes. The controller may utilize a transfer function to convert capacitance and directional tilt (measured by accelerometers, gyroscope, camera, etc.) of the controller/monitor into fluid volume in milliliters or other appropriate units.

In some embodiments, a capacitive sensor is mounted on the inside of the controller and may use out-of-phase techniques to reduce interference from within the proximity, such as a human hand near or in contact with the container. Such a technique uses a level electrode, reference electrode, environment electrode, ground electrode, and two shield electrodes. In some embodiments, the drainage volume is calculated by dividing the change in capacitance of the level electrode by the change in capacitance of the reference electrode and multiplying by the known volume that corresponds to the height of the reference electrode. In this embodiment, the height of reference electrode is a fraction of the height of the level electrode, for example but not limited to $1/10^{th}$, $1/20^{th}$ or $1/50^{th}$ of the height of the level electrode. In some embodiments, a compliant layer of material is present on either the controller or the suction canister in the area of the capacitive electrode in order to minimize or eliminate any air gaps between the controller and the suction canister.

In some embodiments of the system, the drainage canister may contain sensing methods used to measure fluid volume in the canister and communicate that information to the controller, for example, via an electrical connection that is completed when the canister and controller are connected. The sensing method may include but is not limited to, a tuning fork submerged in the fluid where the resonant frequency is monitored as the fluid rises; a "float" device which sits on the top surface of the fluid as the level changes and where the position of the float is determined by the controller; a strain gauge that measures the change in weight of the canister as it fills with fluid; a proximity sensor that measures the fluid level within the drainage canister; a pressure sensor at the bottom of the drainage canister that measures the increase in pressure as the fluid height increases.

In some embodiments of the drainage canister, the front plate graduation markings are embossed and contrasting surface finishes are used to enhance visibility for the user.

In some embodiments of the drainage canister, the physical volume graduations are printed on a sticker and applied to the front plate.

In some embodiments of the drainage canister, there are padding or rubber bumper features around various parts of the canister to provide extra cushioning in the event that the canister is dropped to prevent fracturing or spillage.

Drainage fluid volume may be measured and tracked in the presence or absence of air leak determination.

Figure 14:
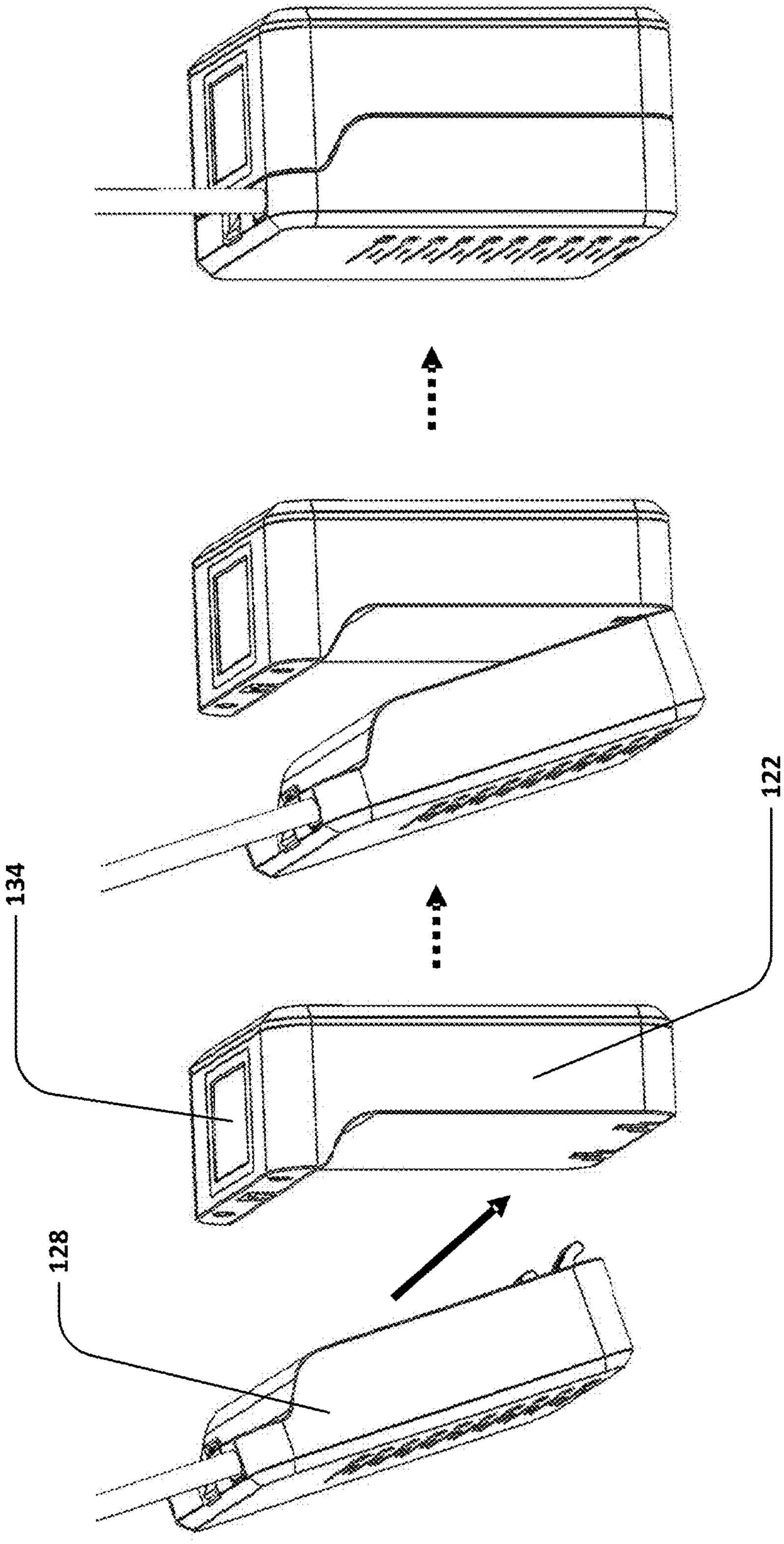
FIG. 14 shows an embodiment of the controller/monitor and the collection canister.

In some embodiments, the chest drainage system includes the monitor/controller shown in FIG. 14. In one embodiment, the monitor includes screen 134, integrated pump (not shown) and mating ports between suction canister/reservoir 128 and controller/monitor 122, including ports to provide suction to the reservoir, open the drainage tube relief lumen valve via integrated solenoid or other means, and capture/secure the drainage tubing and suction canister. In some embodiments, the pneumatic lines are protected by filters integrated into the canister itself to prevent egress of liquid from the canister.

Figure 15:
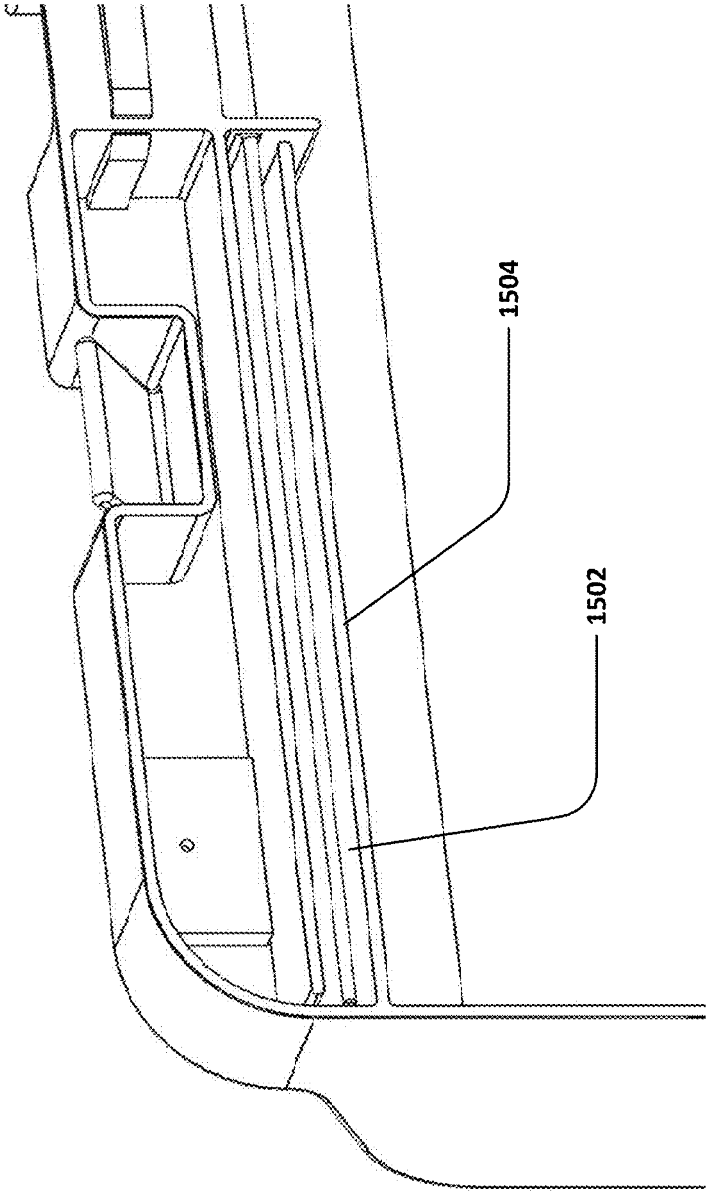
FIG. 15 shows an embodiment of a collection reservoir/canister.

In some embodiments, the suction canister/reservoir is protected from liquid egress by means of a tortuous path created by the internal geometry of the suction canister/reservoir as shown in FIG. 15. The tortuous path may include a series of ribs 1504 and channels 1502 to separate the fluid collection chamber of the reservoir from the vacuum/suction port which connects to the monitor. The tortuous path geometry makes it more difficult for liquid to reach the suction port regardless of monitor orientation. The series of ribs may be connected to the drainage canister on one end and just short of reconnecting at the other end, creating a slight gap. These physical barriers are effective when the drainage canister is laid on its front, back, left, or right sides.

Figure 16:
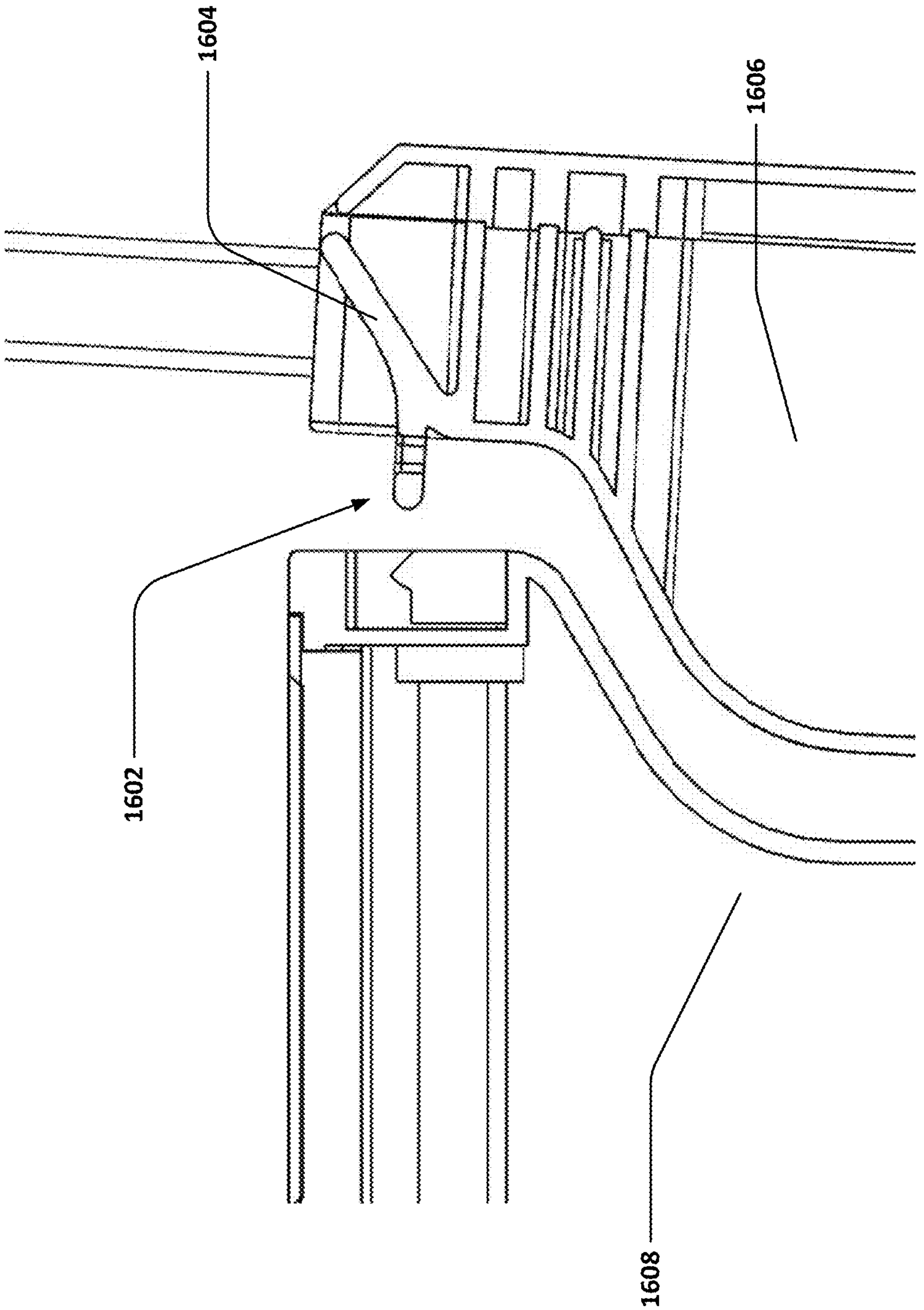
FIG. 16 shows a latching mechanism between the canister/reservoir and the monitor.

In some embodiments, an accelerometer is used to monitor orientation of the monitor and the controller provides an alert when the monitor is in a position that may compromise the suction port. In this example embodiment, the drainage tubing is first connected to the drainage canister and the drainage canister is then connected to the monitor. Alternatively, the drainage tubing drainage lumen and/or drainage tube relief lumen may be connected to the monitor itself, and/or the two tubes (drainage tube drainage lumen and drainage tube relief lumen) may be connected separately. In the embodiment shown, the canister/reservoir is connected to the front of the monitor, but in other embodiments may be connected to the back or either side of the monitor, or be separate. In one embodiment, the suction canister/reservoir has a latching hinge that mates with a latch on the controller as shown in FIG. 16, such that once the canister is connected to monitor 1608, hinge 1604 must be manually depressed in order to disengage latch 1602 and remove canister 1606 from monitor 1608.

Figure 17:
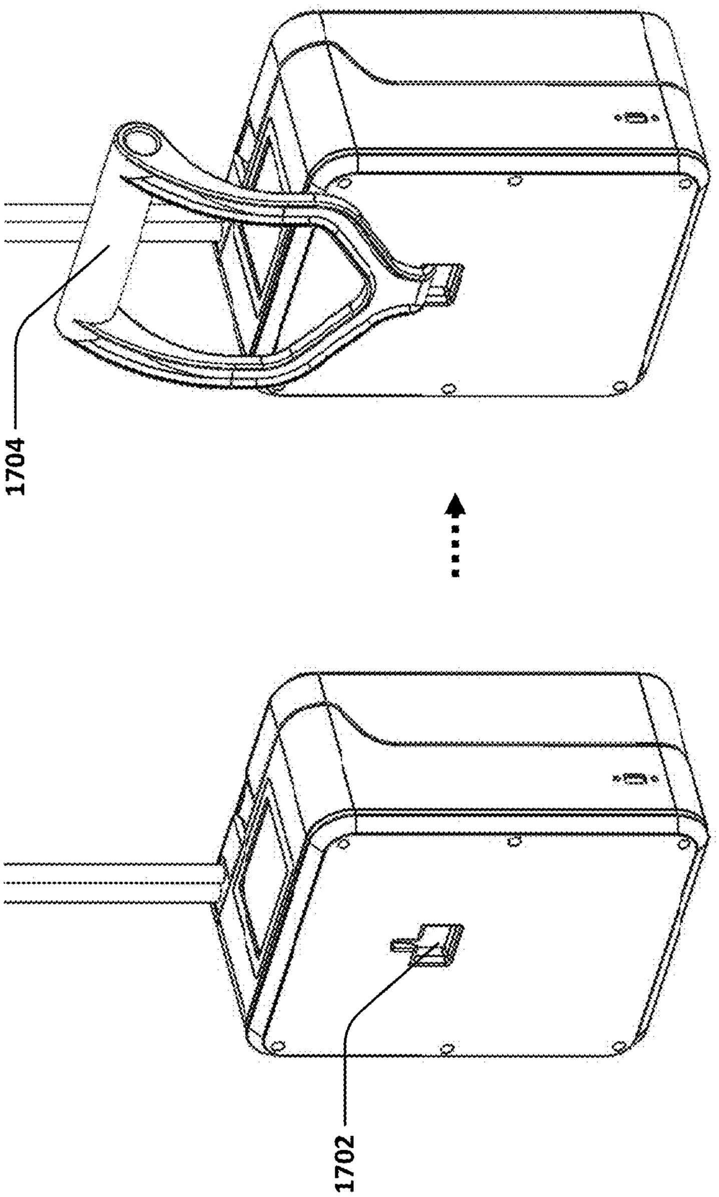
FIG. 17 shows a modular attachment.

In some embodiments of the device shown in FIG. 17, the monitor has modular attachment receptacle 1702 for accepting any number of accessories for mounting or handling the device, including but not limited to bed mounts, IV pole mounts, carrying straps, or handle 1704, as shown in FIG. 17. In some embodiments, the device may have multiple such attachment receptacles to allow for multiple accessories to be connected at once, for example but not limited to a bed mount and a handle or a handle and carrying straps.

In some embodiments, the controller is connected to a network, either wired or wireless, in order to transmit data for example to and/or from the patient's electronic medical record (EMR). The controller may also provide notifications of patient status on the controller/monitor itself and/or by transmitting notifications and/or safety alarms to the EMR or the clinician's phone, tablet, watch, etc.

Chest Tube Removal Readiness.

Some embodiments of the device may include the ability to analyze chest tube removal parameters to inform the clinician about the removal of one or more chest tubes.

Information may be displayed or communicated to the user via the controller. This information may include progress toward chest tube removal, chest tube removal recommendations, and confidence levels for chest tube removal at different times, or with different inputs.

The user may choose which parameters, and/or thresholds of the parameters, to be included in the chest tube removal analysis. These parameters may be determined by the system, such as air leak rate, period of time, drainage rate, air leak rate over time, current drainage volume, drainage volume over time, change in air leak rates, change in drainage volume rates, rate of change of air leak rates, rate of change of drainage volume rates, pressures or pressure changes within the system, pressure at the patient, pressure in the canister, pressure in the drainage lumen, pressure at the barb, pressure elsewhere in the system, chest tube patency, results of air leak challenge, respiratory rate, tidal volume, tidal volume change, and/or other parameters. These parameters may be determined by the controller, or in some instances, entered by a user. Some parameters may be dependent on other parameters. The thresholds for these parameters may be entered by a user, or may be incorporated into the software of the controller. This info may be updated occasionally either by a user, or via a wireless or wired connection, directly to the software of the controller.

For example, a clinician may input a maximum leak rate threshold, and length of time to be monitored by the controller. If the maximum leak rate threshold is not exceeded within the entered length of time, the controller logic may conclude that the criteria for chest tube removal has been met and inform/alert/display this info to inform the clinician.

In another example, drainage rate may be incorporated as a parameter considered in chest tube removal. For example, the clinician may input a maximum drainage rate and/or length of time to be monitored by the device. If the maximum drainage rate threshold is not exceeded within the entered length of time, the controller logic may conclude that the criteria for chest tube removal has been met and inform/alert/display this info to inform the clinician. In some embodiments, drainage rate may be combined with other parameters, including air leak rate, etc. in determining chest tube removal readiness. Any single or multiple parameters and/or thresholds may be incorporated into the chest tube removal readiness analysis.

In some embodiments of the system, the controller may provide information to the clinician relating to chest tube removal readiness. This information may be determined by the system, for example but not limited to, pressure at the patient, pressure in the canister, pressure in the drainage lumen, pressure at the barb, pressure elsewhere in the system, digital drainage volume readings, etc. Alternatively, or additionally, information may be input into the system by the user. For example, the user may input parameters into the system so that the user is notified when a detected active air leak has had a flow rate of <5 mL/min for 4 hours. Alternatively, or additionally, parameters may be pulled into the system from other sources, such as a data provider. Data provided to the controller may be pulled from historical data collected from a larger patient population that inform the controller to notify a user when chest tube may be ready for removal. The controller may utilize an algorithm which "learns" based on parameter data from other patients in similar conditions, i.e. with chest tubes. The data from the other patients may include parameter data such as weight, age, other conditions, time the chest tube has been in place, air leak presence, frequency, flow rate, drainage flow rate, drainage volume, pressure measurements, changes in any of these parameters, etc. The controller may determine when a chest tube is likely to be safely removed based on data from other patients which are similar in one or more than one way. The controller may include the ability to determine the likelihood of complications, reoperations, readmissions, etc., to provide clinical support in a safe and effective way.

In some embodiments, patient information such as body weight, BMI, pre-existing conditions may be input into the controller and inform the model of care that the system provides. The controller may use one or more of the various parameters to provide unique care for the patient, based on what was most effective for other patients similar to the current patient. Data may also be pulled from an electronic health or medical record.

In some embodiments of the device, the controller automatically adjusts the suction level provided to the canister, the drainage line, and ultimately to the patient, based on any one or combination of more than one, parameters. For example, parameters may include the current air leak rate, air leak rate over time, current drainage volume, drainage volume over time, change in air leak rates, change in drainage volume rates, rate of change of air leak rates, rate of change of drainage volume rates, pressures or pressure changes within the system, etc. The controller of the system may instruct the pump to provide the minimum amount of applied suction necessary to maintain sub atmospheric pressure in the chest or at the junction between the drainage line and the chest tube.

In some embodiments of the device, the controller monitors the amount of assistance it is providing to, or has provided to, the patient. For example, the controller may monitor how often vacuum must be applied to the drainage tube to achieve a desirable level of vacuum at the interface of the drainage line and chest tube, or elsewhere in the system. For example, the controller may monitor what level of vacuum must be applied to the drainage tube to achieve a desirable level of vacuum (for example zero, or around zero, or below zero) at the interface of the drainage line and chest tube, or elsewhere in the system.

The information relating to the amount of assistance required may be provided to the user in a format such as percentage of time vacuum has been applied over the past X hours, or the percentage of time that the patient is maintaining a desired level of vacuum, for example, sub-atmospheric pressure, in his/her chest (measured at the drainage line-chest tube interface, or elsewhere in the system) without applied vacuum, for example.

In some embodiments of the device, more than one parameter/criteria may be factored into the controller's analysis of when the chest tube is ready to be removed. Some examples of criteria: suction has been set to around 0 cmH2O for X hours, time since previous air leak rate was above X mL/min is greater than Y hours, time that air leak rate has been below X mL/min is greater than Y hours, pressure within chest has been ≤0 cmH2O for X hours, the chest tube has been verified to be patent, the patient passes a challenge to the air leak (i.e. Valsalva), respiratory rate, tidal volume change, drainage volume rate is less than X mL/hour for the past Y hours, etc.

The number of hours used in the analysis may be 1 hour, 2 hours, 3 hours, 4 hours, 5 hours, 6 hours, 8 hours, 12 hours, 24 hours, 48 hours, 72 hours or other hour increments.

In some embodiments of the device, the chest tube removal criteria which need to be met may be fixed within the software of the device. In some embodiments, the clinician may select which, if any, of the available criteria he/she wants to be considered/incorporated into the analysis. In some embodiments, the criteria may be customizable to better care for a specific patient. In some embodiments, the list of relevant criteria incorporated in the chest tube removal analysis is correlated to specific surgical procedures based on a collection of historical data; the clinician may be able to select the type of procedure on the device to enable the desired criteria.

In some embodiments of the device, the criteria used in the chest tube removal readiness analysis may be received automatically or may be manually entered by a clinician (i.e. Valsalva challenge). In some embodiments of the device, the controller automatically updates criteria and initiates tests, and provides a notification when chest tube removal readiness has been met. In some embodiments, this notification may be accessible on the screen of the device, through a connection to the EMR system, or through a custom application on a mobile device to provide quick and easy access for the physician.

In some embodiments of the device, the controller is capable of automatically running a challenge to an air leak. For example, the controller may audibly or visually indicates a request to the patient to cough (and/or perform another action, such as Valsalva), potentially more than once. The controller monitors the pressure response to the cough(s) and analyzes the signal for signs of an air leak. The results and date/time stamp when the challenge was performed may be displayed on the controller display and/or may be sent to remote devices such as mobile phones, tablets, servers, computers, used in chest tube removal readiness analysis, etc.

In some embodiments of the device, the air leak and/or pressure trends are recorded and analyzed to predict if a patient is likely to have a prolonged air leak. In some embodiment of the device, the controller/monitor returns an alert if a long recovery time is anticipated or communicates/displays anticipated recovery time. In some embodiments, the controller/monitor may adjust the system parameters automatically to accommodate accordingly. In some embodiments of the device, the controller/monitor incorporates the current patient status into the analysis around a rate of healing analysis.

In some embodiments of the device, the device may allow for the patient to leave the hospital with the chest drainage device in place while chest drainage and/or an air leak is still ongoing. The controller may monitor the chest tube removal criteria listed herein, and automatically perform ongoing tests to monitor the air leak status. The controller may provide instructions to the patient to walk the patient through air leak challenges. These instructions may be communicated via a display, audible instructions and/or a remote connection to the user's phone or other computer device. The controller may provide a notification to the patient to call the hospital and schedule a time to remove the tube, or the controller may alert the hospital and/or physician automatically.

In some embodiments of the system, the physician may remotely access the device to observe the patient's current status, activate an air leak challenge while talking with the patient over the phone, or through the device. In some embodiments, the controller may be set to a mode which allows limited interaction with the device by the patient. For example, the patient may be able to initiate an air leak challenge or monitor the status of the prescribed criteria indicating the chest tube is ready to be removed.

User Interface

Figure 19A:
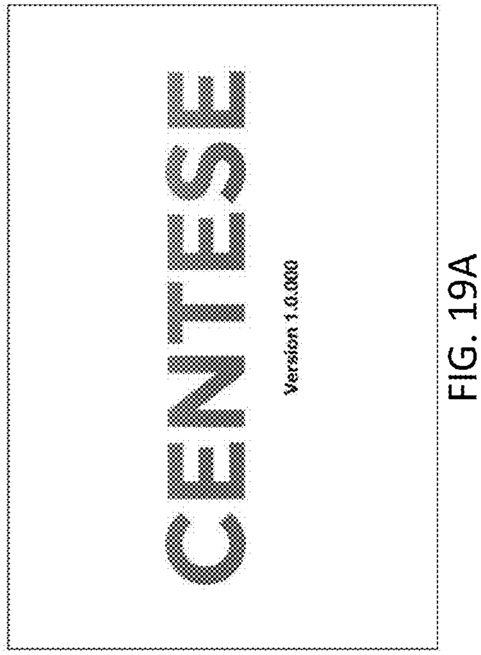
FIGS. 19A-19Z show possible graphic user interface screens.
Figure 19B:
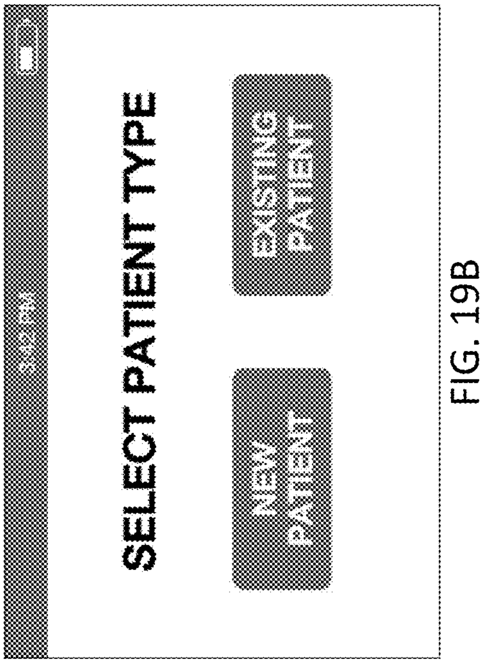
Figure 19C:
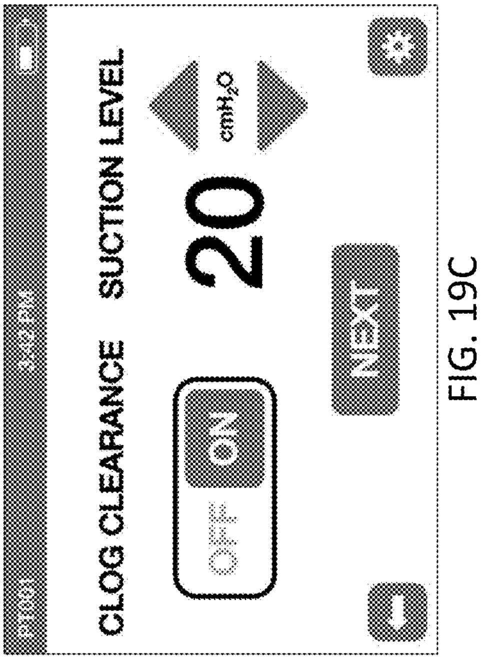
Figure 19D:
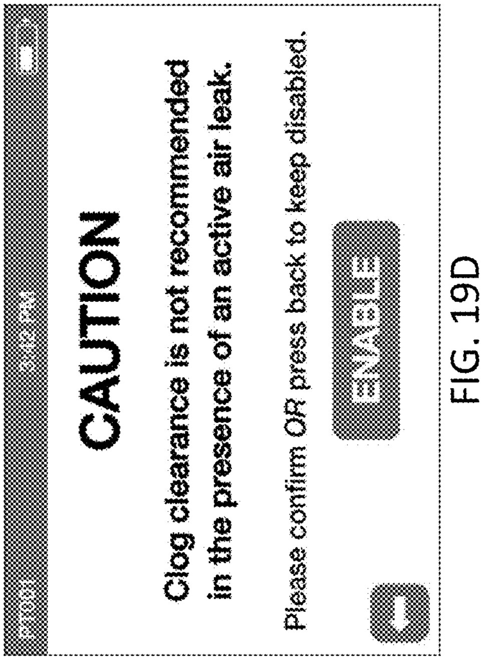
Figure 19E:
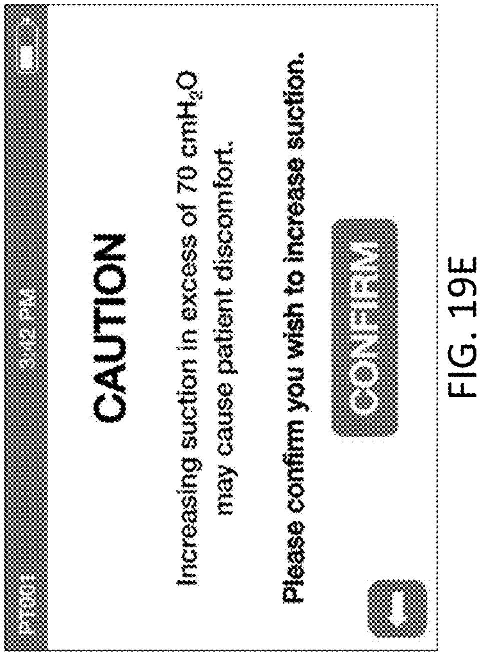
Figure 19F:
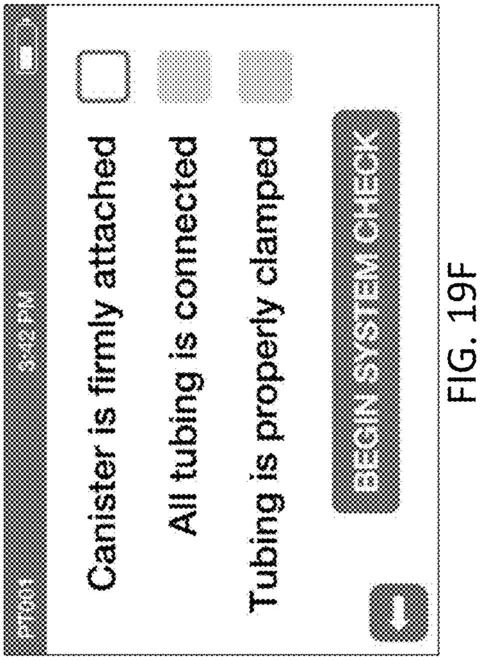
Figure 19G:

In some embodiments, a graphical user interface is displayed on the display of the controller. In some embodiments, the Graphical User Interface (GUI) may include the screens depicted in FIGS. 19A-Z. These screens may display information, as well as collect input from the user, for example via touch screen input. Upon boot up of the device, a flash screen is displayed, which includes the current version of the software (FIG. 19A). The user is then prompted to select whether the patient is new or existing (FIG. 19B). Next, the user sets the clog clearance feature to on or off and also sets the initial suction level for the patient (FIG. 19C). If clog clearance feature is turned on, the user may be prompted to confirm (FIG. 19D). Similarly, if the user attempts to increase the suction level to higher than 70 cmH2O, he/she may be asked to confirm the setting (FIG. 19E).

Figure 19H:
Figure 19I:
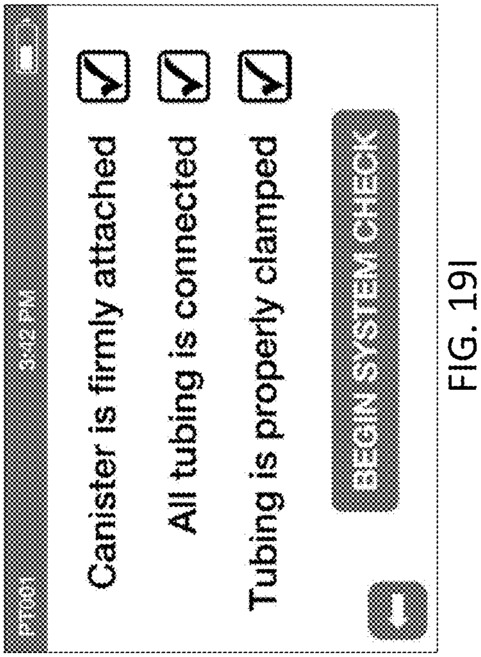
Figure 19J:
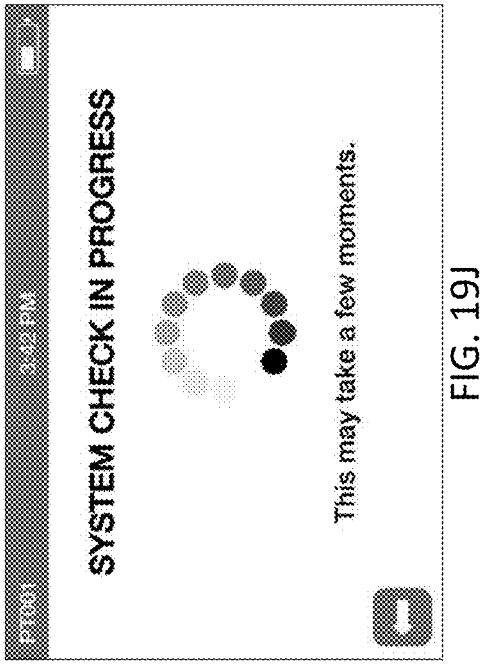

Next, the system prompts the user to complete a self-check, which requires the user to confirm that the canister is firmly attached (FIG. 19F), that all tubing is connected (FIG. 19G), and that the tubing is properly clamped (FIG. 19H). At this point the user can begin the self-check (FIG. 19I). During the self-check, the system may check for presence of the drainage canister via a reflective tab and for airtightness of the system via pressure measurements (FIG. 19J). The self-check process may include the controller pulling suction to a specified level and monitoring changes in pressure to verify air-tightness of the drainage canister, connections of the drainage tubing are properly made, and the seals pneumatically connecting the drainage canister to the controller are secure.

As part of the system initialization and drainage canister replacement processes, the controller may check for the presence and proper connection of a drainage canister before continuing to normal operation. The drainage canister may be equipped with a highly-reflective tab. The controller utilizes a built-in, infrared reflectivity sensor to detect the proper installation of the drainage canister using the reflective tab. The reflectivity of the reflective tab is acutely sensitive to the relative angle of the reflective tab to the sensor and can determine whether the drainage canister is fully seated or not. The controller may verify that the canister attached is an authentic drainage canister.

Figure 19K:
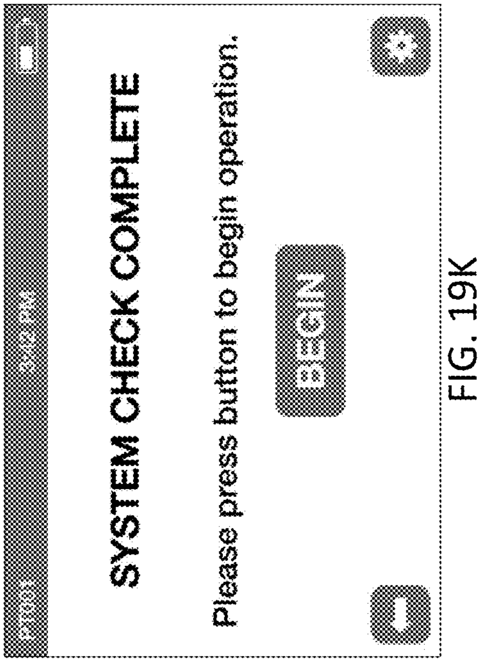
Figure 19L:
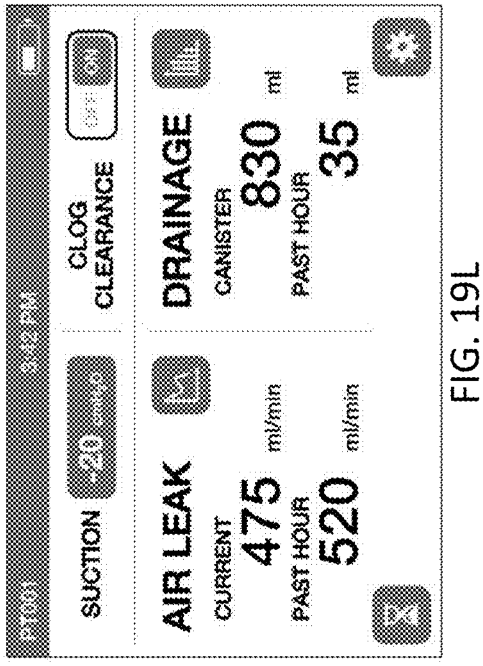

If the system check is successful, the controller then allows the user to begin using the system (FIG. 19K). At this point, the system's main screen is displayed, which provides information on the suction setting, the status of clog clearance, the amount of air leak (current and over the past hour, or other time frame), and the amount of drainage (in the canister and over the past hour or other time frame) (FIG. 19L).

Figure 19M:
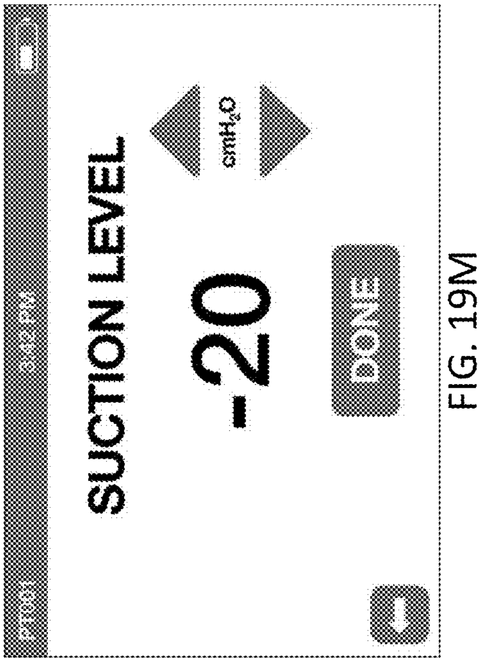
Figure 19N:
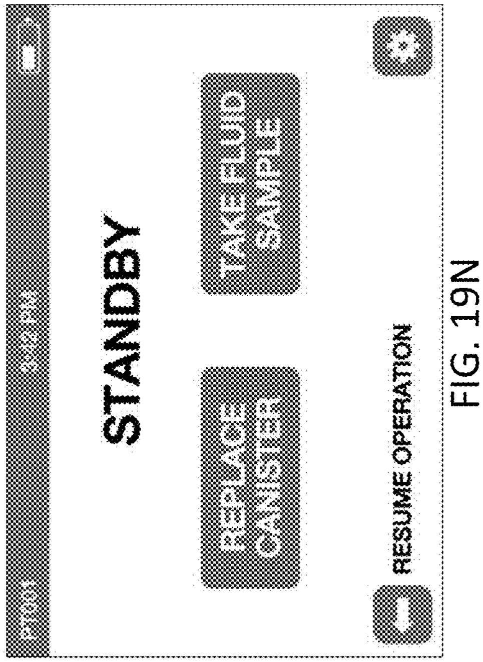
Figure 19O:
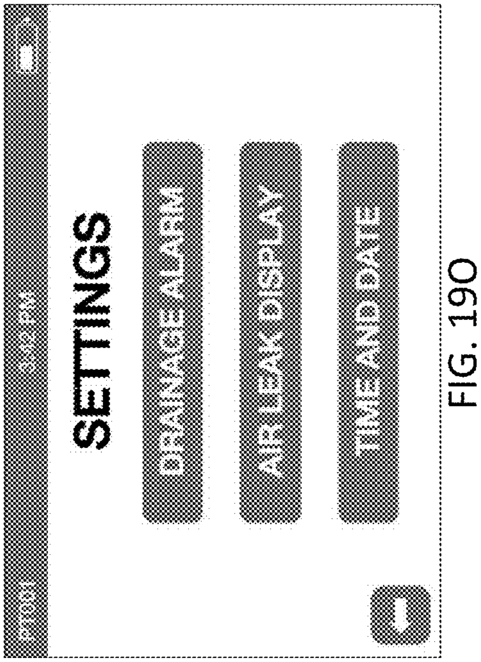
Figure 19P:
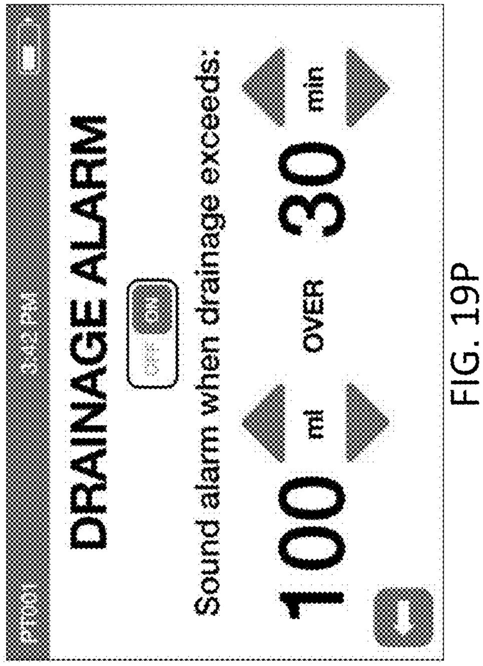
Figure 19Q:
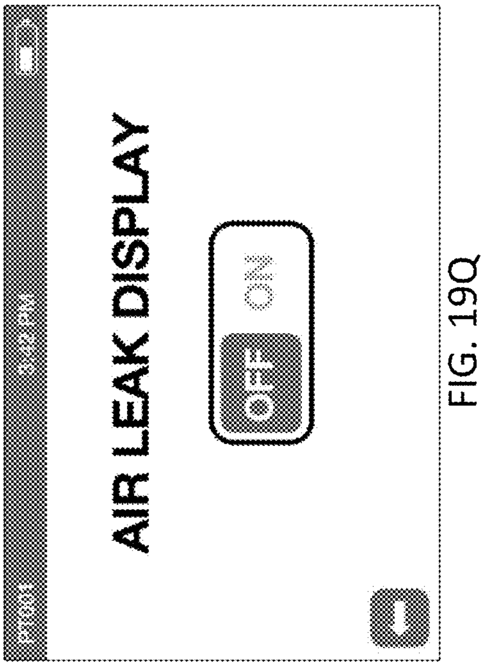
Figure 19R:
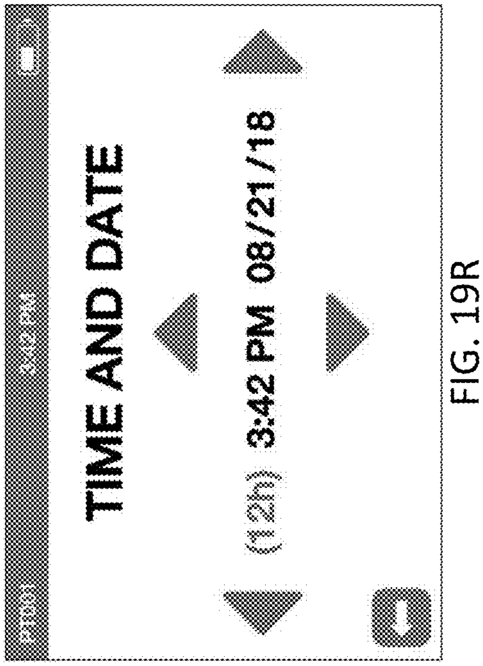
Figure 19S:
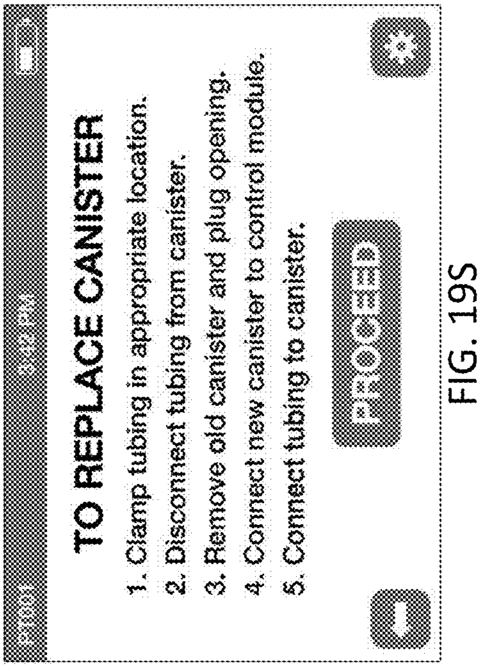
Figure 19T:
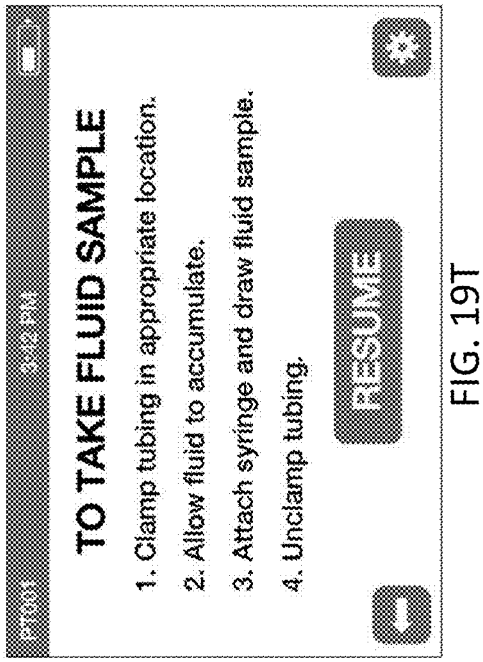
Figure 19U:
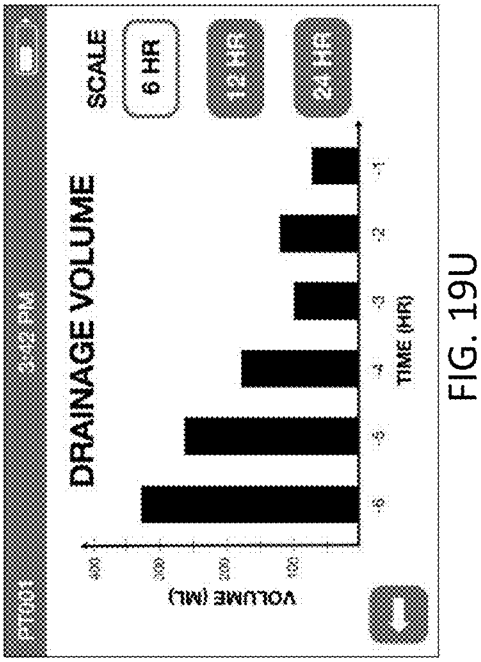
Figure 19V:
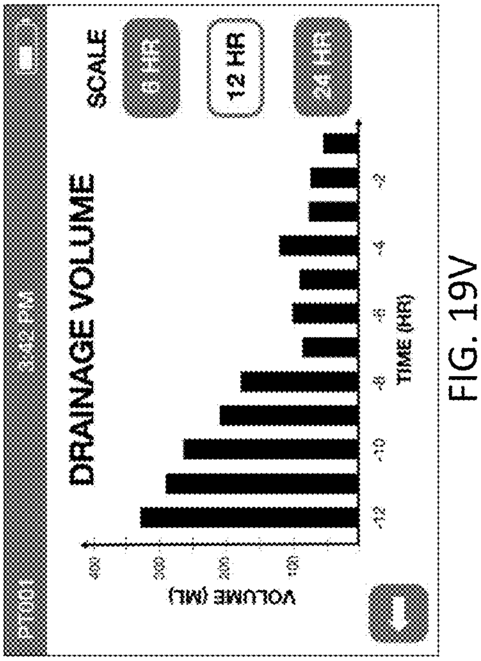
Figure 19W:
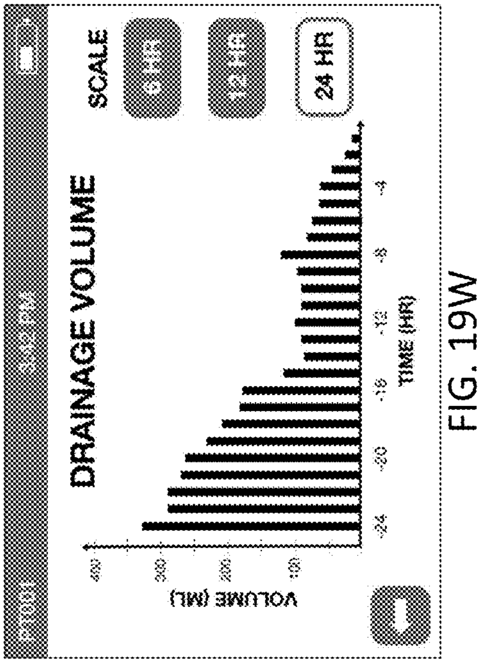
Figure 19X:
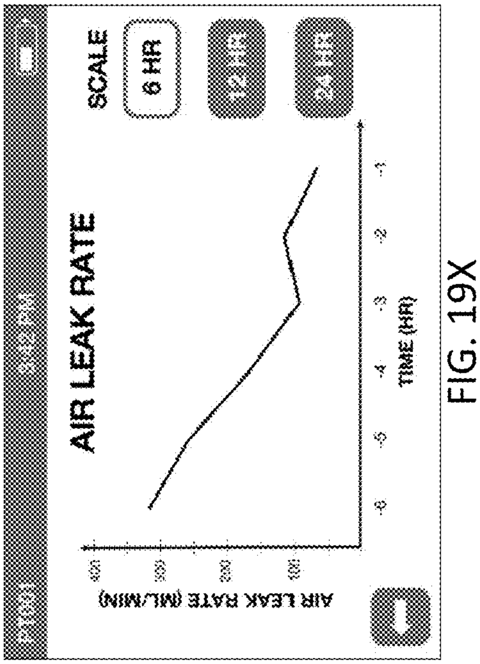
Figure 19Y:
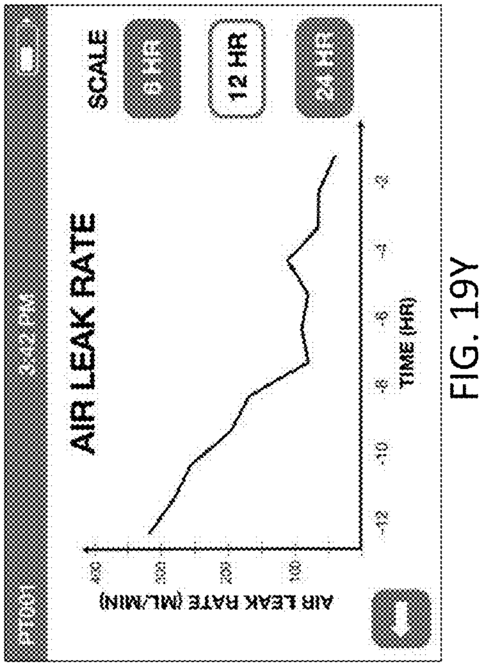
Figure 19Z:
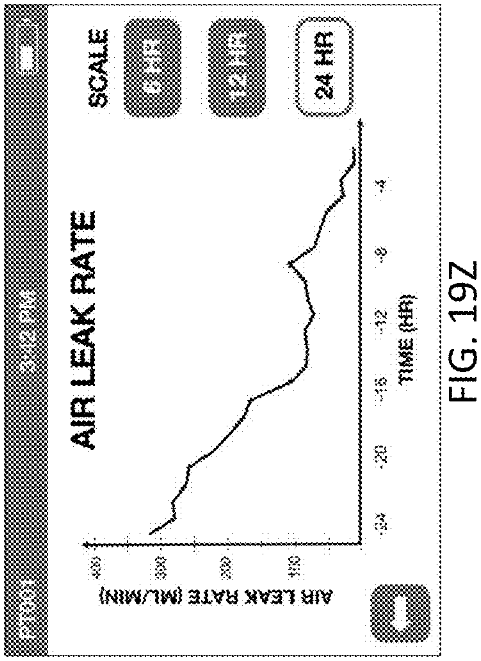

If the user presses the suction level on the main screen, he/she is taken to the suction setting screen, where it can be adjusted (FIG. 19M). Also accessible on the main screen is the standby button (hourglass icon at bottom left). When the user presses this button, he/she is prompted to either resume operation, replace the canister, or take a fluid sample (FIG. 19N). Also accessible on the main screen is the settings button (gear icon at bottom right). When the user presses this button, he/she is prompted to access the drainage alarm, air leak display, or time and date (FIG. 19O). Upon pressing the drainage alarm button, the user can turn the alarm on and off as well as adjust the drainage rate threshold for alarm activation (FIG. 19P). Upon pressing the air leak display button, the user can turn on or off the display of air leak information on the main screen (FIG. 19Q). Upon pressing the time and date button, the user can adjust the time and date of the system (FIG. 19R). When the replace canister button is pressed via the standby screen, the user is prompted to follow the on-screen instructions (FIG. 19S). Similarly, when the fluid sample screen is pressed via the standby screen, the user is prompted to follow the on-screen instructions (FIG. 19T).

In addition, the controller may display a screen and/or sound an alarm when the canister is full if the capacitive sensor detects that the drainage canister has reached its maximum capacity. The controller will alert and prompt the attending physician to replace the canister. If the alert is ignored or an attempt to use a full canister is made, the controller may not allow normal operation until a new, or empty, drainage canister is attached.

In addition, the controller may display a screen and/or sound an alarm if the canister is disconnected from the controller. This may be determined using IR sensor(s) which determine when the drainage canister is no longer connected or not fully connected, to the controller. The controller will alert and/or prompt the attending physician to re-attach the canister. If the alert is ignored or not addressed properly, the controller may not allow normal operation until the drainage canister is properly attached.

In addition, the controller may display a screen and/or sound an alarm if the battery level is below a set threshold. The controller may prompt the user to plug the device into wall power to recharge the battery. If the alert is ignored and the battery level approaches dangerously low levels, the controller may place the system in a safe state before power is lost. The controller may display remaining battery life as a time or percentage. The battery icon may also implement color coding to indicate battery level.

In addition, the controller may display a screen and/or sound an alarm if the air leak rate is above a set threshold. The controller may alert and prompt the attending physician of the leak presence and prompt the physician to check the system for signs of leaks coming from tubing connections, chest tube drainage hole placement, etc. The controller may continue to alert until the air leak is resolved.

In addition, the controller may display a screen and/or sound an alarm if the drainage volume rate has exceeded the acceptable value as defined by the attending physician in the settings. The controller may alert and prompt the attending physician to verify the volume in the drainage canister using physical graduations or other means. The controller may continue to alert until the issue is resolved.

In addition, the controller may display a screen and/or sound an alarm if an obstruction is detected in the chest tube. If the controller attempts to run a clog clearance cycle and the pressure readings at the tube-tube interface exceed the maximum suction threshold, it will alert and prompt the attending physician to check the chest tube for any kinks or obstructions within the tube. The controller may continue to alert until the issue is resolved.

In addition, the controller may display a screen and/or sound an alarm if an obstruction is detected in the drainage line. If the controller attempts to draw suction and the suction level in the drainage canister increases (the pressure becomes more negative) but the suction level at the tube-tube interface doesn't change significantly, it will alert and prompt the attending physician to verify that the tubing clamp is disengaged and check for any kinks or obstructions within the drainage tubing. The controller may continue to alert until the issue is resolved.

In addition, the controller may display a screen and/or sound an alarm if the device is knocked over. If the controller detects a change in position of the system beyond the acceptable range, it will alert and prompt the attending physician to return the device to its upright position. The position detection may be done with accelerometers, a gyroscope, camera, etc. The controller may continue to alert and place the system in a safe state until the issue is resolved.

Also accessible on the main screen are the air leak and drainage volume trend buttons (graph icons next to respective text). When the user presses these buttons, they are taken to screens displaying historical data over the past 6, 8, 12, or 24 hours, depending on the user selection (FIGS. 19U-Z). On all screens, the time and battery status may be displayed.

The battery icon is shown with a lightning bolt in its center when it is plugged in, and becomes red when critically low. On screens other than the patient selection screen, the patient ID number may be displayed.

In some embodiments, the system may display an icon or alert when the patient has met predetermined criteria for air leak rate and/or drainage volume that indicate the chest tube is ready to be removed.

Controller/Monitor Mount

In some embodiments of the device, the controller has a handle which incorporates a hook or multiple hooks, to hold the controller in a desired location, such as on a bed, an IV pole, or other location.

Figure 48A:
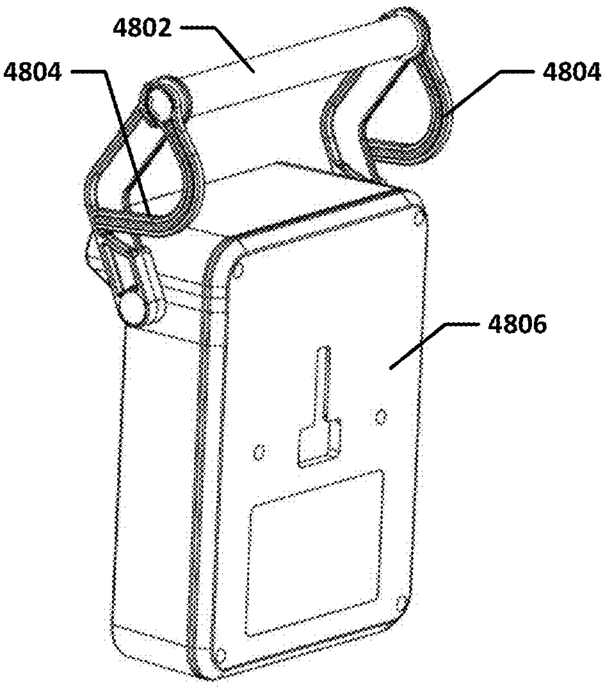
FIGS. 48A-48C show an embodiment of a controller/monitor mount which includes handle 802 which incorporates hooks.
Figure 48B:
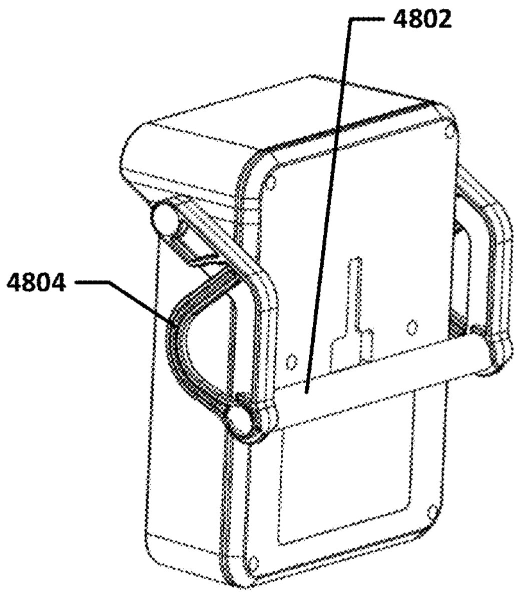
Figure 48C:
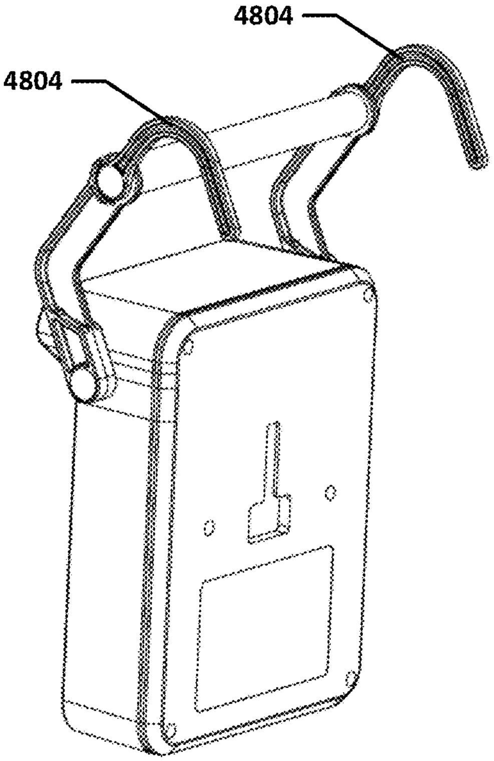

FIGS. 48A-48C show an embodiment of a controller/monitor mount which includes handle 4802 which incorporates hooks 4804. The handle is attached to controller/monitor 4806. FIG. 48A shows this embodiment in a position where handle 4802 is pivoted upward so that it can be easily grabbed to carry the monitor. FIG. 48C shows this embodiment where hooks 4804 are in a position which allows them to be hooked onto a table, poke, bed, etc. FIG. 48B shows this embodiment where both handle 4802 and hooks 4804 are folded down and out of the way.

Figure 49:
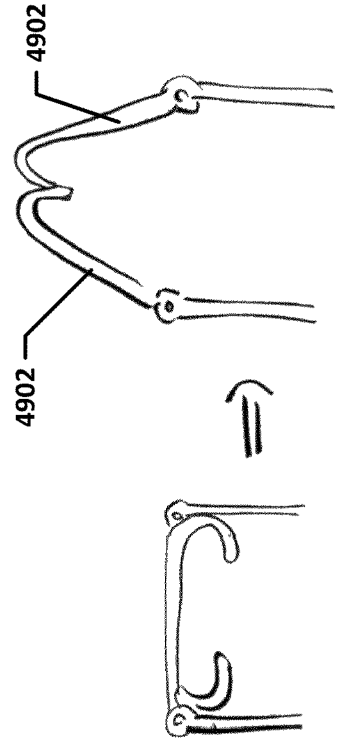
FIG. 49 shows an embodiment of a controller/monitor where hooks come together to form a handle.

FIG. 49 shows an embodiment where hooks 4902 come together to form a handle.

Figure 50:
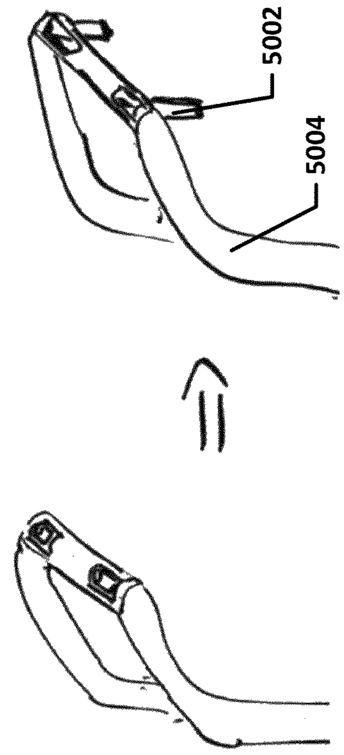
FIG. 50 shows an embodiment of a controller/monitor where hooks are nested within the handle and pivot outward or downward when needed.

FIG. 50 shows an embodiment where hooks 5002 are nested within handle 5004 and pivot outward or downward when needed. In this configuration, there may be one or multiple hooks, which may be positioned at the ends of the handle to straddle the device as shown here, or alternatively in the middle of the handle.

Figure 51:
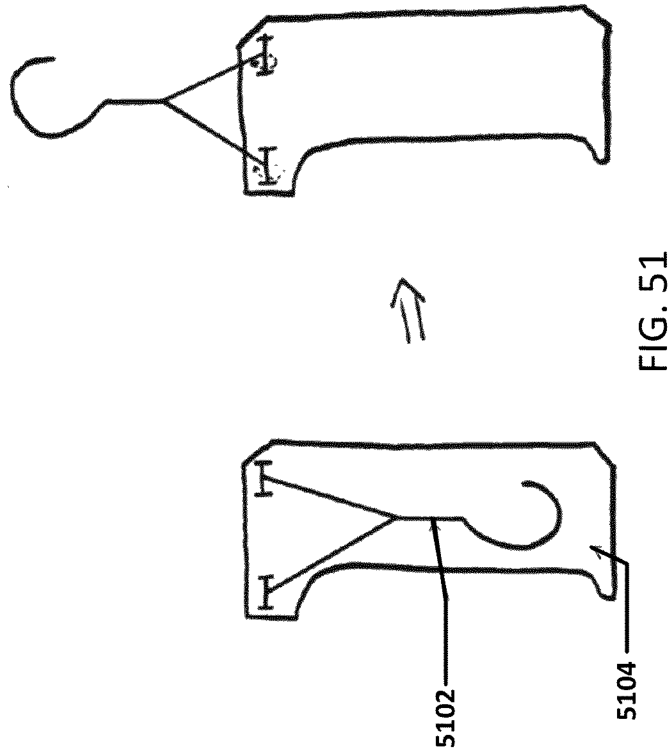
FIG. 51 shows another embodiment of a controller/monitor where hooks are attached to either side of the controller/monitor.

FIG. 51 shows another embodiment where hooks 5102 are attached to either side of controller/monitor 5104. When not in use, the hooks rest along the side of the device and rotate about the connection point(s) up into position for use.

In some embodiments of the device, the mounting/hook mechanism may incorporate a mounting clip, which has geometries to both connect and align the clip appropriately to the device. The mounting clip may include a feature(s) to prevent accidental removal of the clip (e.g. a tab that activates once the clip is in position, locking it in place). In some embodiments, the mounting clip may be attachable to various mounting options for the control module, including but not limited to, a handle for carrying the device, a hook or hooks used to hang the device from a hospital bed or IV pole, or a floor mount which elevates the device off the ground.

Figure 52:
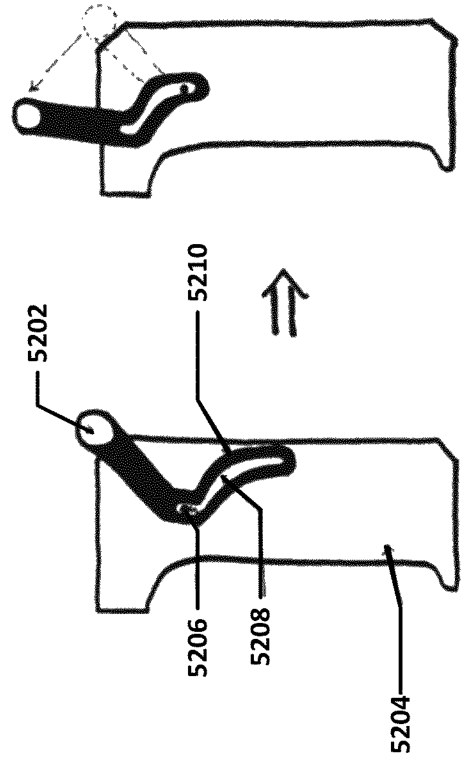
FIG. 52 shows another embodiment of the controller/monitor mount where a handle is attached to the sides of controller/monitor.

FIG. 52 shows another embodiment of the controller/monitor mount where handle 5202 is attached to the sides of controller/monitor 5204 and rests along the backside of the controller/monitor when not in use. The handle may include guide post 5206, guide slot 5208, and slotted bracket 5210. The handle may be pulled upwards to move it into position, so that the device may be easily carried.

Figure 53:
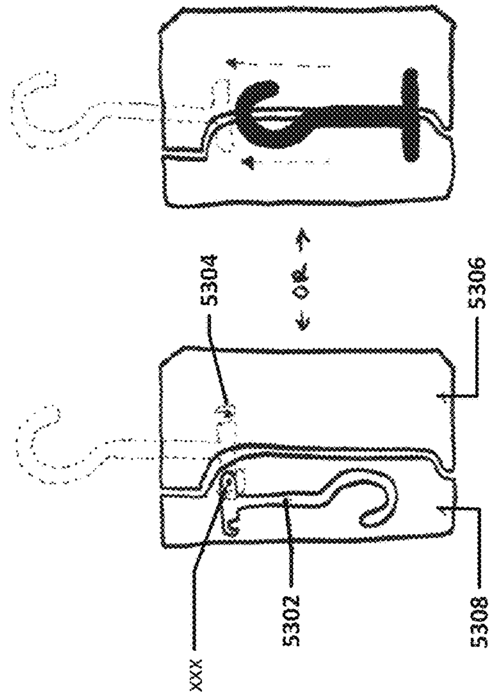
FIG. 53 shows hooks rotated into a vertical position for use.

In some embodiments, hooks or similar features are affixed to the sides of drainage canister 5308 instead of, or in addition to, the controller/monitor. FIG. 53 shows hooks 5302 which can rotate into a vertical position for use. In the vertical position, the hooks are supported by support feature 5304 incorporated into the sides of controller/monitor 5306 which supports the hook so that the entire system is supported. In some embodiments, the hook features slide up into position to accomplish the same function as above. In a similar embodiment, these hook features are incorporated into the controller/monitor and the supporting features are located on the drainage canister.

Figure 54:
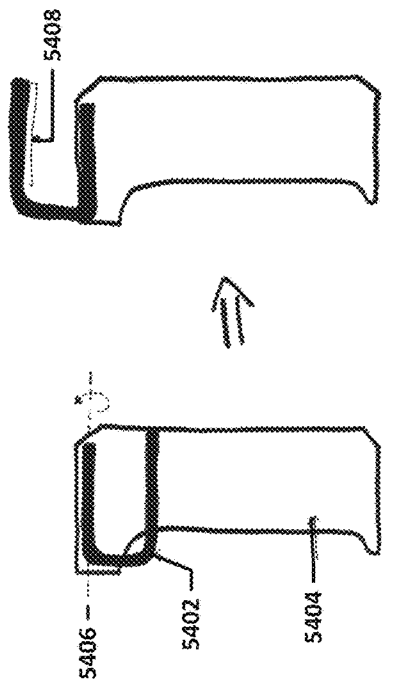
FIG. 54 shows an embodiments of the controller/monitor mount which includes collapsible hooks mounted to the sides of the controller/monitor.

FIG. 54 shows an embodiments of the controller/monitor mount which includes collapsible hooks 5402 mounted to the sides of controller/monitor 5404 which can be rotated or pivoted around axis 5406 into a position above the controller/monitor for supporting the device via mounting surface 5408. These hooks may have a geometry to capture the center of mass of the system to help keep the system upright.

Figure 55:
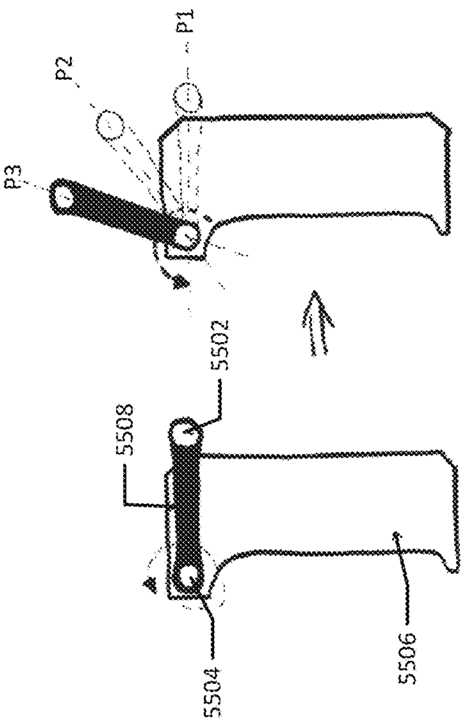
FIGS. 55 and 66 show embodiments of the control module where a handle may rotate from a resting position along the back side to a position for hand carrying above the top side of the control module.
Figure 56:
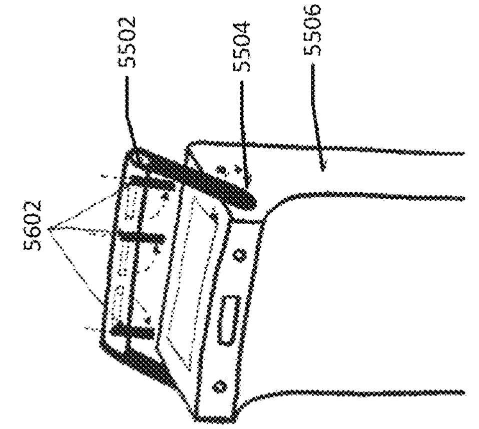

In some embodiments of the control module, a handle assembly is affixed to control module 5506 and can rotate from a resting position along the back side to a position for hand carrying above the top side of the control module as shown in FIGS. 55 and 56. The mechanism for the limited rotation may be, for example but not limited to, a pair of cylindrical pieces, which may include connecting bracket 5508, which can rotate about a shared axis, but which may have physical geometries that only allow rotation within a certain range. Within this handle, there may exist hook features 5602 that are stored within handle 5502 while not in use and are able to swivel, pivot, slide out, or move by some other mechanism to provide mounting features. In some embodiments of the handle assembly, the handle and/or hook features can lock into place at various positions about pivot point 5504, for example P1, P2 and P3, so as to allow for a wider variety of mounting options, for example but not limited to, a lock position where the hook features are able to engage with a bed rail or other mounting location where the hook must be slightly behind the control module to provide adequate support.

Figure 57:
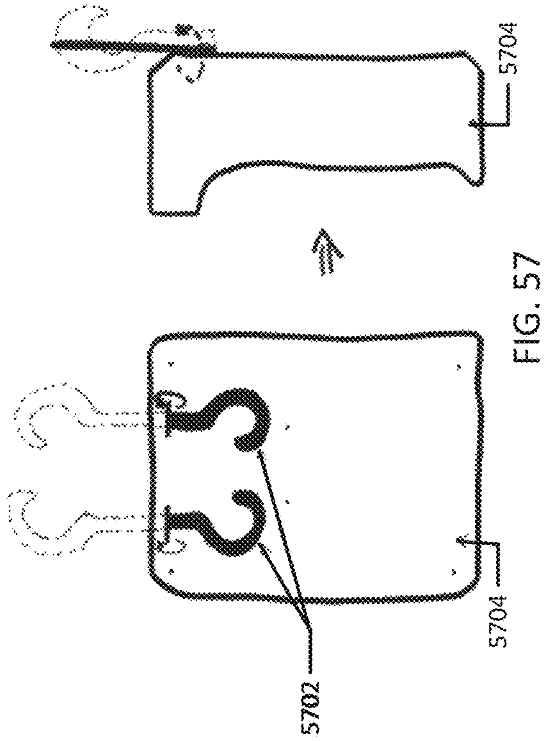
FIG. 57 shows an embodiment of the device where hook features are stored along the backside of control module when not in use.

FIG. 57 shows an embodiment of the device where hook features 5702 are stored along the backside of control module 5704 when not in use. The hooks can pivot and swivel into a position that allows them to be used to support the system. These hooks may be separated by some distance to allow for a connection with multiple points of contact, or nearly adjacent to provide a single-point connection.

Figure 58:
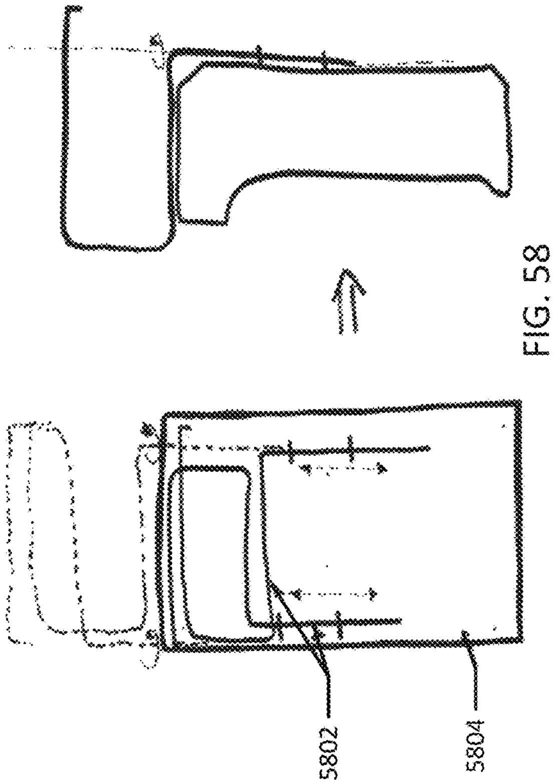
FIGS. 58 and 59 show another embodiment of the control module mount where a pair of hooks are attached to the backside of the control module and are able to be hidden away when not in use.
Figure 59:
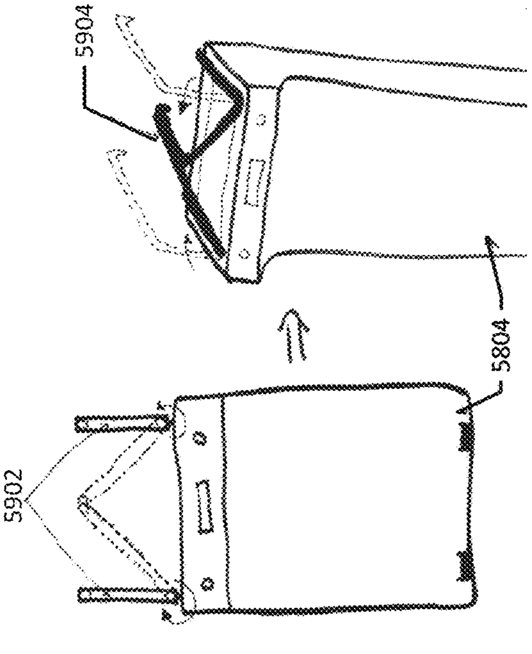

FIGS. 58 and 59 show another embodiment of the control module mount where a pair of hooks are attached to the backside of the control module and are able to be hidden away when not in use. In use, these hooks have a geometry so as to capture the center of mass of the system to provide a stable, upright mount. Hooks 5802 are able to slide, pivot, and rotate from their hidden position to a position on the top side of control module 5804. For dual-point mounting, the hooks can remain parallel to each other shown by hooks in position 5902. For a single-point mount, the hooks are able to rotate and meet in the middle, shown by hooks in position 5904, effectively creating a single mounting point or surface. When the hooks are in this position, they can also act as a carrying handle. In some embodiments, the hooks have a way of temporarily connecting to one another, so as to make the handle feature more rigid and prevent the hooks from moving relative to one another, for example but not limited to, a rotary piece that moves to capture a stud feature on the other hook.

Figure 60:
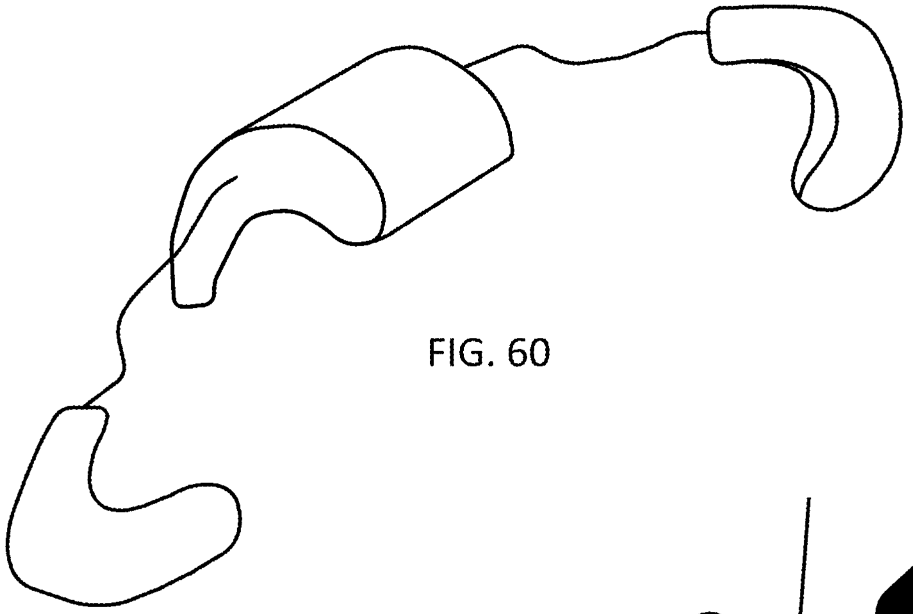
FIG. 60 shows an embodiment of the control module mount where hook features are collapsible into the cross-sectional geometry of a handle feature and can be stored out of sight when not in use.

In some embodiments of the control module mount, hook features are collapsible into the cross-sectional geometry of a handle feature and can be stored out of sight when not in use, as shown in FIG. 60.

Figure 61:
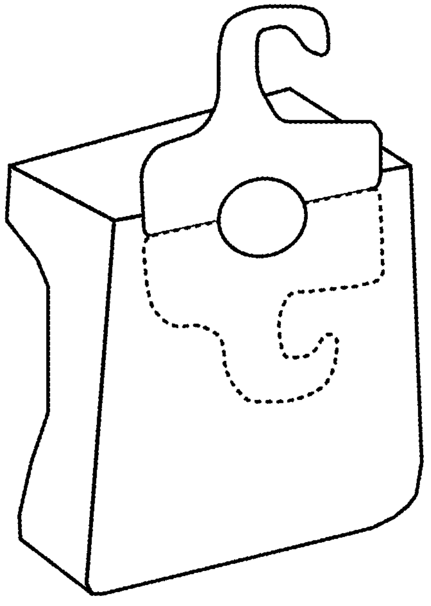
FIG. 61 shows an embodiment of the control module mount where a collapsible hook feature for single point mounting is embedded into the back of the control module for storage and rotates into place for mounting.

In some embodiments of the control module mount, a collapsible hook feature for single point mounting is embedded into the back of the control module for storage and rotates into place for mounting, as shown in FIG. 61.

Figure 62:
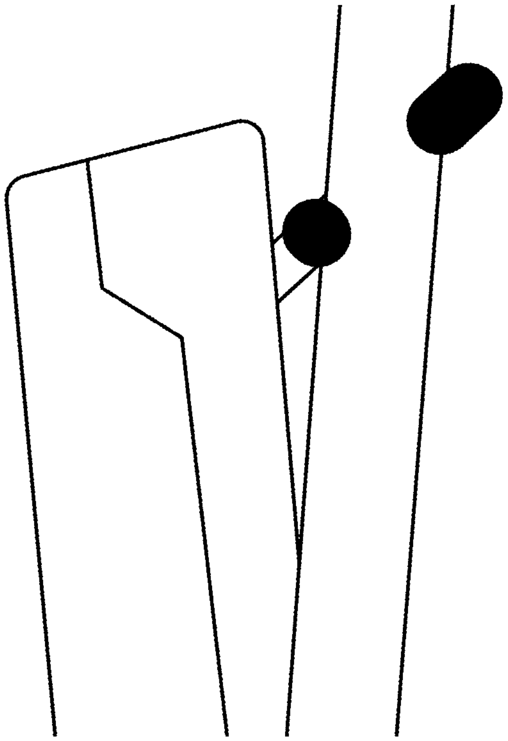
FIG. 62 shows an embodiment of the control module which has a feature attached to it that allows for vertical mounting onto.

In some embodiments, the control module has a feature attached to it that allows for vertical mounting onto, for example, an IV pole using the force of gravity and friction between the mount and the pole to hold the control module in place, as shown in FIG. 62.

Software

In some embodiments of the system, the location of a clog can be determined to be either in the chest tube or the drainage tubing. When the system attempts to clear a clog in the chest tube, it temporarily increases the level of suction by running the pump. If, after the pump is turned off, this increased suction (which may be measured at the canister) does not attenuate substantially within a set time period, this indicates that the chest tube relief valve has not opened and air has not entered the system. This means that a clog has been detected. As a result of this condition, the controller may open the drainage tube relief valve connected to the relief lumen of the drainage tubing. If the suction (negative pressure) measured in the canister still has not attenuated substantially (become less negative), the controller may determine that the clog is likely in the drainage tubing. If adequate attenuation of the pressure measured in the canister does occur after opening the drainage tube relief valve, the controller may determine that the clog is likely in the chest tube.

In some embodiments, the controller can determine the clog location based on pressures sensed in both the drainage canister and at the tube-tube interface. In these embodiments, suction is increased in order to clear the chest tube. If the suction (negative pressure) measured in the drainage canister increases (becomes more negative) above a set threshold, including but not limited to −40, −60, −80, −100, −120, −140, or −160 cmH2O, while the pressure at the tube-tube junction remains at a lower (less negative) suction value, the controller may determine that the clog is in the drainage tubing. If the canister suction does not differ substantially relative to pressure at the tube-tube junction after increased suction is pulled, and attenuation of suction in the system does not occur after the pump has been turned off or decreased, the controller may determine that the clog is in the chest tube. The controller may also be able to determine what type (size, brand, configuration, etc.) or quantity of chest tube(s) is connected to the system based on the measured pressure(s) within the system.

In some embodiments of the system, the minimum suction necessary to keep up with the patient's air leak rate is used to minimize the differential pressure between the inside and outside of the patient's lung in order to expedite healing of the site of the air leak. In this mode, the user is not required to choose a specific suction level, as the system controller will automatically maintain the minimum level necessary to keep the patient's lung inflated.

In some embodiments, the system may have pre-set recommendations for drainage volume or air leak rates which indicate when it is appropriate for removing the patient's chest tube. The system may indicate when the air leak rate and/or drainage volume values are within acceptable levels, or may instruct the user to remove the patient's chest tube. In some embodiments, these recommendations may be based on the historical trends of data from a specific patient, or from aggregated patient data. These data are not limited to drainage volume and air leak rate data, other data collected, or associated with a patient or patient population, may be used.

Connectivity and Additional Functionality

Some embodiments of the system may transfer data either to or from the chest drainage system controller via hard wire connection or wirelessly. Wireless connections may include wi-fi, NFC, Bluetooth, cellular transmission, proprietary RF channel, or similar methods. Information transmission may be one-way or two-way. Communication may be with computers including servers, personal devices (phones, tablets, watches, etc.), other medical devices, cloud/remote based software, or electric systems.

Data may include, but are not limited to, any one or more of the following:

Data collected by the system: fluid volume drainage status and changes, air leak status and changes, response to certain air leak challenges, drainage tube and/or chest tube patency status and changes, pressure status and changes at one or more points in the system, respiratory rate status and changes, tidal volume status and changes, fluid drainage rate, system status, alarm notifications, air leak rate, system usage levels, system usage duration, battery level, average suction, applied changes, maintenance requirements, other programmed notifications, etc.

Data in other systems: patient health data, patient demographic data, aggregated patient data, etc.

Data may be transmitted actively or passively. Recipients of the data may have the option to view data or make system operating changes or both, either manually or defined by an algorithm. Data transmission may be collated for transmission into different sub-groups based on predefined user groups, access level, or allowable remote inquiry.

In some embodiments, the patient's drainage volume output as measured by the device is transmitted to an infusion pump and/or feeding pump, and the amount of fluids being administered are automatically adjusted accordingly. In this manner, the system may be part of a closed-loop fluid balance system, which may include, for example, systems for measuring fluids such as urine output, fecal output, wound drainage, perspiration, and moisture lost during respiration, and systems for administering fluids, such as infusion pumps and feeding pumps.

In some embodiments, the system is capable of communicating with other control modules, hospital monitoring systems, electronic health records, electronic medical systems, or other devices to either share and display information to physicians (e.g. air leak rate or drainage volume over the past hour), to receive information about the patient to be used for various actions (e.g. heart rate, body temperature, or O2 levels to gain insight on patient stability), or to send information about the patient to other devices for various actions (e.g. drainage volume output to inform autotransfusion machine of necessary input to compensate).

In some embodiments, the controller has the capability of wireless charging, for example but not limited to, exposed electrodes that engage with the charging electrodes of a charging station or dock; integrated wireless charging functionality in bedside or floor mount.

In some embodiments, the system makes use of mechanisms to prevent tampering or re-use of disposable components. In one such embodiment, the system may require authorization via PIN or swiping an RFID enabled badge, for example, in order to enable or disable device settings or functionality. In some embodiments, the system requires a specific set of screen touches in order to unlock the device and modify settings or functionality. The disposable components may become unusable after being removed from the controller, for example but not limited to a break-away latch connector that snaps off when the drainage canister is removed from the controller.

In some embodiments, the system has a "check for air leak" mode in which the system monitors various characteristics, including but not limited to, pump activation and pressure, to help identify the presence of an air leak as a final check before removing the chest tube from the patient. One embodiment of this functionality may include a 1-minute data collection period during which the patient coughs, sits up, or does some other action as cause for an air leak to show up; afterwards, the controller screen may indicate the results, for example but not limited to, a plot of chest pressure over time, pump activation over time, air leak in mL/min over time, or an info screen that displays the results in a text or graphic format.

Figure 20:
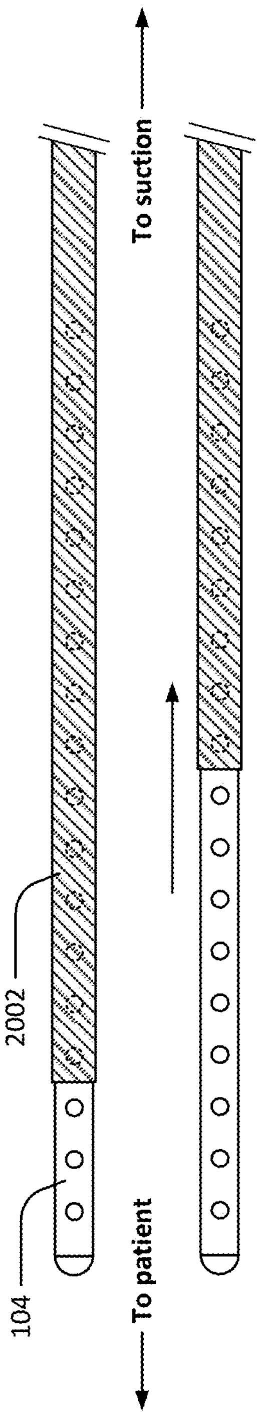
FIG. 20 shoes an embodiment of the chest tube which includes a sheath.

Depending on the physician and/or patient, the desired length of drainage holes or channels may vary; therefore, it may be desirable for the chest tube to have a modular drainage area length to adapt to each clinical situation. In one embodiment of the chest tube, a sheath, such as silicone sheath 2002, is preinstalled, or may be installed by the user, along the length of chest tube 104. The sheath may be moved or removed as desired to expose additional drainage holes as shown in FIG. 20. The sheath may be on the inside or the outside of the chest tube. The method for moving the sheath, or removal of all or part of the sheath, may include: rolling or stretching the chest tube to allow the sheath to move freely around the chest tube, sliding the sheath along the chest tube, cutting the sheath, optionally with a specially designed instrument or tool, tearing the sheath, pulling a suture or thread to change the length of the sheath, etc. The sheath may include weakened sections or objects to facilitate removal.

Figure 21:
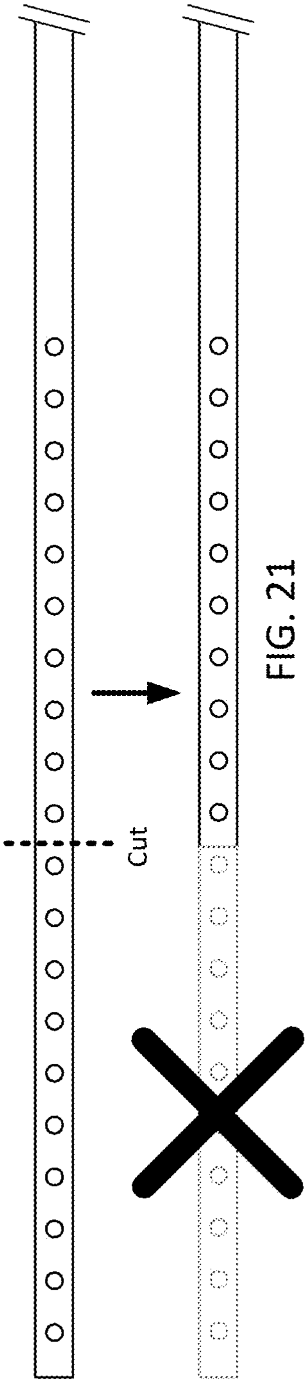
FIG. 21 shows an embodiment of the chest tube which can be cut to length.

In some embodiments, the chest tube may come with an excessive drainage area length to allow the physician to cut the drainage area to the desired length, by cutting the chest tube to length. This is shown in FIG. 21. In this embodiment, the system may include a special tool to create the connection hole between the chest tube drainage lumen and the chest tube relief lumen after the chest tube has been cut to length.

In some embodiments of the chest tube, various drainage area lengths may be offered, for example, 4", 5", or 6", less than 4" or longer than 6".

Figure 22:
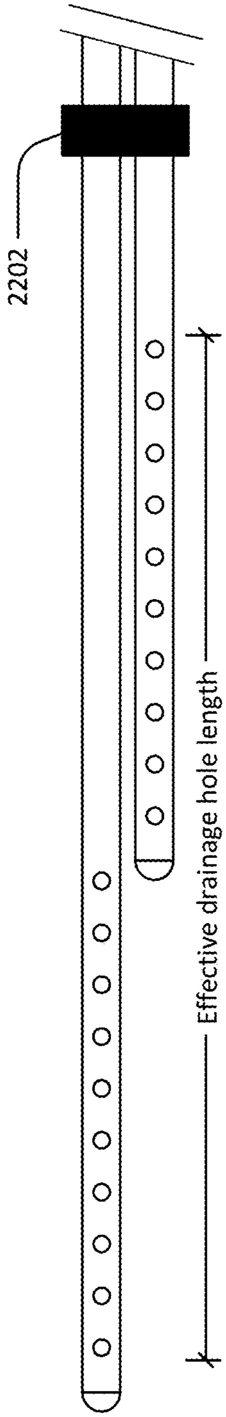
FIG. 22 shows an embodiment of the system which combines more than one chest tube.

In some embodiments of the chest tube kit, an additional component, such as connecting, or holding, component 2202 is included with the system. Component 2202 holds more than one chest tube together such that the effective hole length is increased, as shown in FIG. 22.

Figure 23:
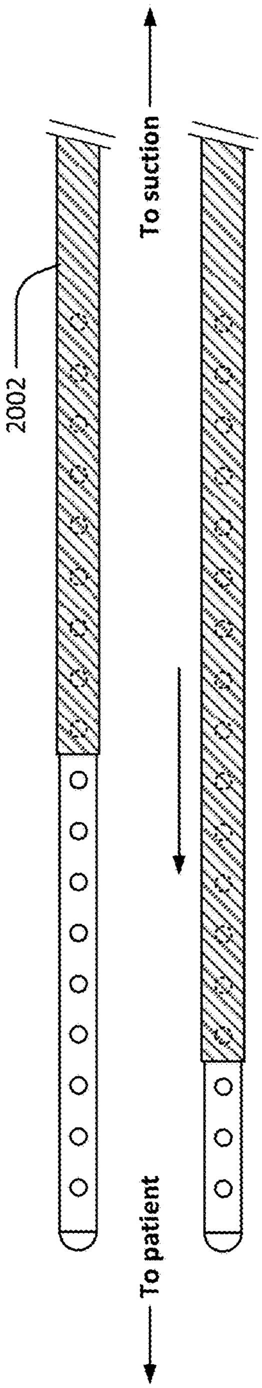
FIG. 23 shoes an embodiment of the chest tube which includes a sheath.

In some embodiments of the chest tube, a silicone, or other material, sheath is incorporated at the proximal end of the chest tube and can be pulled toward the distal end (the patient end), or in the opposite direction, to cover or uncover exposed holes, until the desired drainage area length is achieved as shown in FIG. 23.

In some embodiments of the chest tube kit, a silicone, or other material, tape is included to cover drainage holes until the desired drainage area length is achieved.

Figure 24:
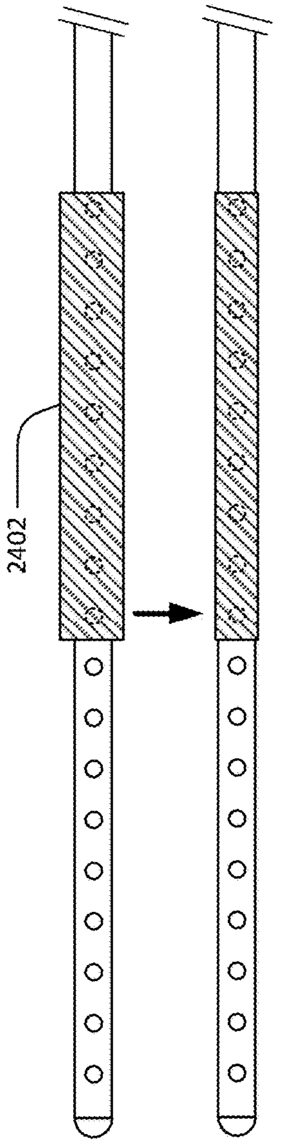
FIG. 24 shoes an embodiment of the chest tube which includes heat shrink tubing.
Figure 25:
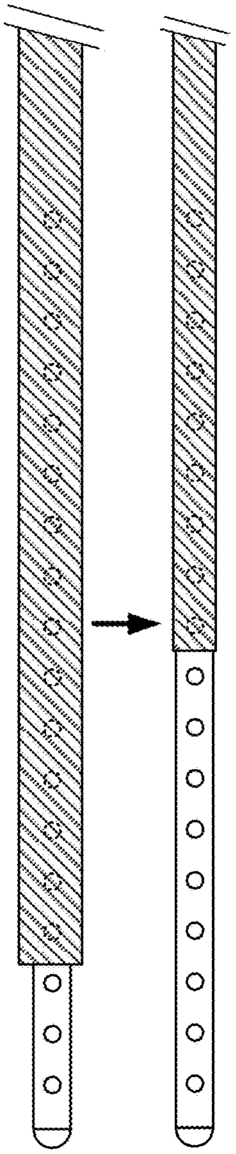
FIG. 25 shoes an embodiment of the chest tube which includes heat shrink tubing.

In some embodiments of the chest tube, heat-shrink tubing 2402 may be placed over the undesired drainage areas, as shown in FIG. 24, and shrunk down to cover undesired drainage areas. The heat shrink tubing may or may not shrink in length as it shrinks in diameter. If the heat shrink tubing does shrink in length as heated, it may be used to expose more drainage holes by fixing the tubing at the proximal end, forcing the length of the tubing to decrease as heat is applied, as shown in FIG. 25.

In some embodiments of the chest tube kit, a mandrel and punch are included to allow physicians to punch additional holes as desired. Pad-printed markers may indicate where surgeon-generated hole creation is acceptable and where it should not be cut.

Figure 26:
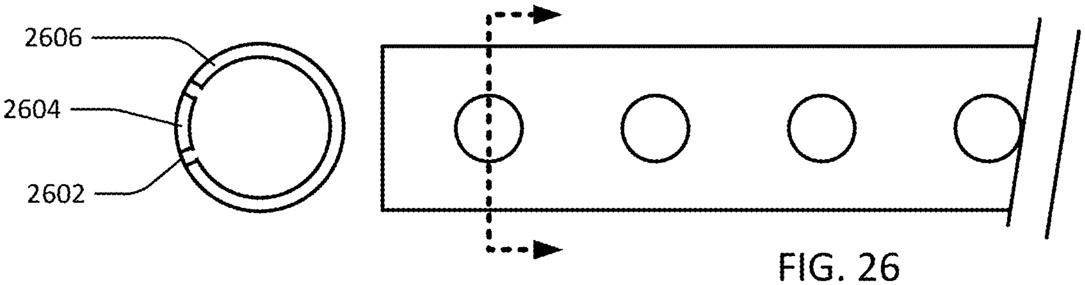

In some embodiments of the chest tube, the drainage holes are not completely punched, leaving thin film 2602 attaching hole slug 2604 to chest tube 2606. The physicians would then pull or punch out the desired number of slugs to create an appropriate drainage hole length or number as shown in FIG. 26. The thin film may dissolve in the presence of fluid, such that the appropriate drainage area length is automatically created when the chest tube is placed in the patient.

In some embodiments of the chest tube, drainage area length may be exposed using a silicone-based zipper.

Figure 27:
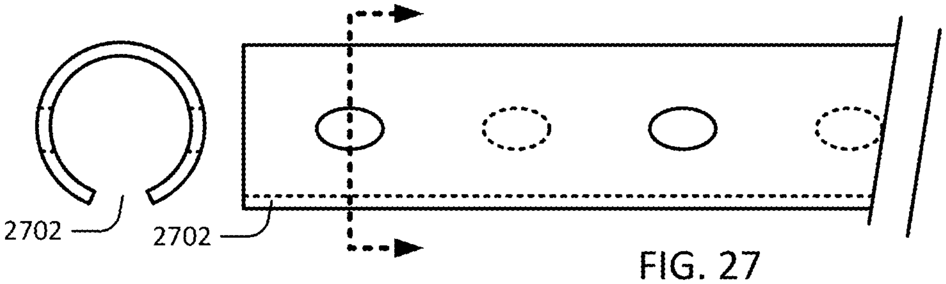
FIG. 27 shoes an embodiment of the chest tube which includes a drainage channel opening.
Figure 28:
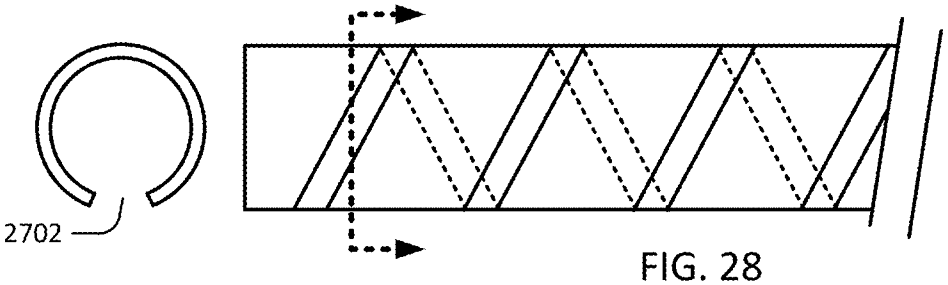
FIG. 28 shoes an embodiment of the chest tube which includes a drainage channel opening.

In some embodiments of the chest tube, the dual-lumen extrusion has continuous drainage channel opening 2702 along one or more sides, with additional holes along the sides, as shown in FIG. 27. The chest tube may be cut to the desired length by the physician; a special tool may then be used to create the connection hole between the chest tube drainage lumen and the chest tube relief lumen. In some embodiments, the channel opening pivots back and forth radially along the length of the extrusion to improve drainage area coverage, as shown in FIG. 28.

Figure 29:
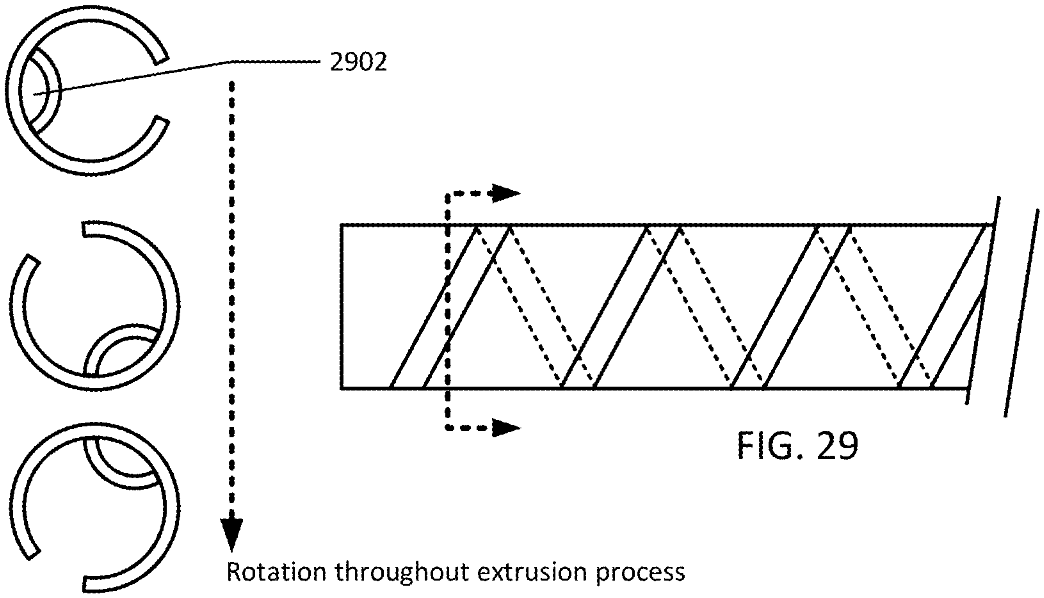
FIG. 29 shoes an embodiment of the chest tube which includes a drainage channel opening.

In some embodiments, the chest tube profile (dual-lumen with a channel on the side) is rotated during the extrusion process, so that the drainage area is present in all directions at some point along the extrusion, as shown in FIG. 29. FIG. 29 shows chest tube relief lumen 2902. Note that any of the embodiments disclosed herein, including the embodiments shown in FIGS. 20-29, may include a chest tube relief lumen, similar to that shown in FIGS. 6A and 6B.

Figure 30:
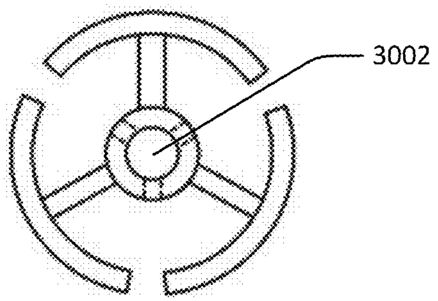
FIG. 30 shoes an embodiment of the chest tube which includes more than one drainage channel opening.

In some embodiments of the chest tube, the extrusion consists of a channel drain with independent relief lumen 3002 running down the center, shown in FIG. 30. The chest tube may be cut to the desired length by the physician; a special tool may then be used to create a connection hole between the independent relief lumen and adjacent channels.

In some embodiments of the chest tube, a single channel is cut into the bottom of the extrusion; then twisted axially and heat set to generate a similar result as described above.

In some embodiments, the canister, or other components of the system, may include a hydrophobic, or other suitable, coating to repel body fluids. For example, if the drainage canister gets tipped over or knocked around, blood may coat the inside of the canister and leave a film, creating the potential for drainage volume measurement interference. In one embodiment of the device, a hydrophobic chemical coating may be applied to the inner surface of the drainage canister to repel bodily fluids. The coating may be on the entire canister, or on only certain areas. For example, for example, the coating may be placed on the inner wall nearest to the volume sensing mechanism.

In some embodiments, a thin film may be applied to the canister to repel bodily fluids. The film may comprise polypropylene, polycarbonate, PTFE, Teflon, or other materials. In some embodiments, modified surface finishes may be utilized to prevent blood and other particulate from sticking to the inner surface of the drainage canister. Any of the aforementioned methods for preventing adhesion of blood and other particulate may also be applied to other components of the system, for example, the chest tube, drainage tube, relief valve, and drainage barb.

In some embodiments, anti-foaming mechanisms and/or chemicals may be incorporated into the drainage system, and in particular, into the canister. For example, an anti-foaming additive may be added to the canister to reduce bubbling of drained fluid. In some embodiments, the drainage canister material itself may provide anti-foaming functionality. Hydrophobic and/or oleophobic materials and/or additives may be used for different applications throughout the system. For example, in some embodiments, a blood-repellant barrier may be utilized at the entrance to the drainage tube relief line of the drainage barb to prevent ingress of fluid. The anti-foaming mechanism may be in the form of an anti-foaming tablet, which is incorporated into the canister. The tablet may comprise simethicone, or other anti-foaming ingredient(s).

Figure 31:
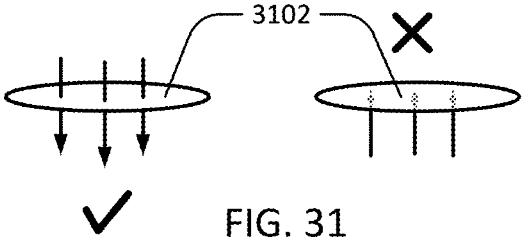
FIG. 31 shows a repellant barrier.

In some embodiments, a blood-repellant barrier may be incorporated within the drainage canister at the entrance to the suction inlet to act as a protection mechanism to the suction source, in the event of an overfilled canister. In some embodiments, blood-repellant barrier 3102 may be incorporated within the drainage canister at the drainage inlet to allow blood and other fluids to pass through into the canister while being repelled from passing through the opposite direction, out of the drainage inlet, as shown in FIG. 31.

In some embodiments of the device, the system may allow for autotransfusion of blood to be re-introduced to the patient. For example, the drainage canister may feature a luer lock valve, stopcock, or other port that can be connected to an autotransfusion machine. This port may also be used to remove contents of the drainage canister during use, if so desired by the physician.

Figure 32:
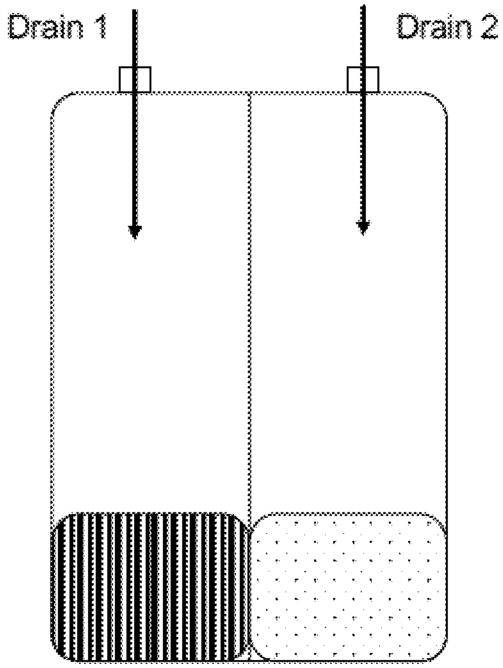
FIG. 32 shows an embodiment of the drainage canister with more than one collection chamber.

In some embodiments, the drainage canister may consist of a single chamber for collecting the drainage fluid. In some embodiments, one or more rib(s) or support(s) may be added to the drainage canister main body or front plate to provide additional rigidity and strength to the canister. In some embodiments, the drainage canister may comprise two or more separate chambers to collect draining fluid(s) as shown in FIG. 32. The canister may have multiple drainage inlets to be connected in various configurations; for example, one chamber may be connected to a chest tube in the mediastinum, while the other chamber may be connected to a chest tube in the pleural space. Or, for example, both chambers may be connected to chest tubes that reside in the same space but in different locations, so that drainage output based on location of chest tube placement may be investigated. In some embodiments, the system may provide different functions to each chamber independently. For example, one chamber may be set to a suction level of −20 cmH2O with clog clearance activated, while the other chamber is set to a suction level of −40 cmH2O without clog clearance active.

Figure 33:
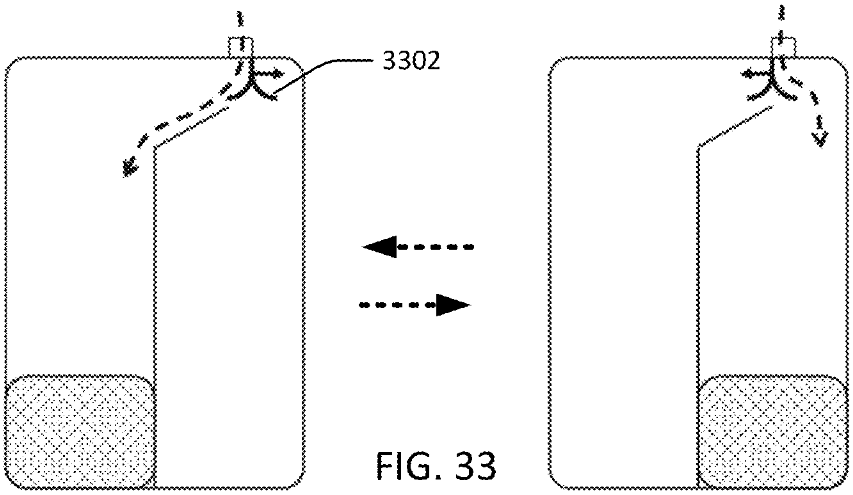
FIG. 33 shows an embodiment of the drainage canister with more than one collection chamber.

In some embodiments, the drainage canister may function as either a single chamber or dual chamber device as shown in FIG. 33. The functionality of the canister may be toggled manually by a clinician, for example, using slide lever 3302 to manipulate into which chamber the draining fluid is drained. In a similar embodiment, the functionality of the canister may be toggled through software/hardware by the controller, for example, using a manifold to control the path of fluid drainage.

In some embodiments of the drainage canister, the suction port may automatically seal off when disconnected from the controller, for example, by using an umbrella valve, diaphragm valve, or duckbill valve to allow flow out of the canister but not in, making it possible for patient ambulation with the drainage canister alone. In this embodiment, the suction within the canister is maintained even when disconnected from the controller. The drainage tubing remains connected to the canister the entire time, making the use of this functionality simple and easy.

In some embodiments, the drainage tubing may be clamped via a mechanism incorporated into the drainage tubing, such as a valve, switch, or manifold. The clamping mechanism may be internal to, or external to, the drainage tubing. This clamping device may be activated manually by the attending physician or automatically by the controller. In some embodiments of the drainage canister, the drainage canister is offered in a variety of sizes with different volumetric capacities, for example 800 mL, 1600 mL, and 2000 mL.

In some embodiments of the drainage canister, the controller is able to detect specific information about the drainage canister in use, such as total volumetric capacity, relevant features (for example, anti-foaming, hydrophobic, etc.), and patient identification information (to prevent cross-contamination of bodily fluids when used in conjunction with autotransfusion). This information may be provided to the controller by, for example, RFID detection, color detection, or magnetic field detection.

In some embodiments of the drainage canister, data may be stored on the canister (stored to EPROM) in the event that a controller needs to be swapped out, to prevent data loss.

Alarms

In some embodiments, the device has alarms for various conditions that may affect the performance of the device and/or the safety of the patient, such as when the canister is full, the battery is low, or the chest tube is clogged. Some of these alarms and the user actions to be taken to resolve them are shown in FIG. 34.

In some embodiments of the device, alarms may have the option to be muted for some length of time, such as 1 hour, 4 hours, or similarly, alarms may have defined limits on how frequently they can occur, for example as often as 15 minutes or 30 minutes.

In some embodiments of the device, alarms are accompanied by an on-screen prompt that provides a list of relevant actions available to the clinician based on the type of alarm triggered. For example, if a chest tube clogged alarm has sounded, the screen may prompt the user to run a clog clearance cycle again immediately or to run a sweep cycle for 30 minutes.

Pathogen Filtration/Containment

In some embodiments of the chest drainage system, particles or contaminants, such as virus and bacteria particles, which may be in the fluid evacuated from the patient, may be filtered and/or contained by the controller/monitor. Some embodiments of this functionality may include a filter membrane within the collection canister to filter air prior to exhausting the air through the control module. The filter may have a pore size sized to filter viruses and/or bacteria from the air. If rated in terms of pore size, the pore size may be, for example, 0.45 μm, 0.2 um μm 0.02 μm, etc. The filter material itself may be, but not limited to, polytetrafluoroethylene (PTFE), expanded PTFE, acrylic copolymer, or any other suitable membrane for filtration of viruses and/or bacteria.

In one embodiment which includes this functionality, the controller/monitor of the system may include a filter membrane on either side of the suction pump. In some embodiments of this functionality, the controller/monitor of the system may include a custom exhaust port which may receive an exhaust filter to filter air exhausted from the system. In some embodiments of the system, a filter membrane may be placed between the collection canister and the controller/monitor of the system. In this configuration, the filter may filter air as air exits the collection canister and enters the controller/monitor. In some embodiments, a filter membrane may be placed between the patient and the collection canister, for example between the chest tube and the drainage line, to allow for filtration of pathogen material prior to entering the collection canister. Filter membranes may filter air, liquid, or both. Different types of filters may be placed at different locations within the system.

In an alternative embodiment, the system may incorporate a ultraviolet (UV) light source to sterilize, or significantly reduce active pathogens within, the exhausted air, for example by causing cell death. In one embodiment, the controller/monitor may contain a UV light source which directs the UV light toward air passing through the system. A sufficient dose (intensity×time) of UV light may reduce the danger of pathogens in the air. In some embodiments, the controller/monitor may direct the UV light toward the drainage canister to reduce pathogens in the air and/or fluid within the drainage canister. In some embodiments, the drainage canister itself may incorporate a UV light source. In this embodiment, for example, the UV light may be generated by means of a UV LED or multiple UV LEDs powered by, for example, a coin cell battery.

In some embodiments, the system may reduce the transmission of aerosolized pathogens through reduction or elimination of humidity in the exhausted air from the system. In some embodiments, the controller/monitor contains a compressor dehumidifier which dehumidifies the air as it passes through the system. The dehumidifier may be elsewhere in the system as well. In this embodiment, the collected moisture may be re-introduced into the collection canister from within the control module. As a secondary benefit to this embodiment, the system may provide additional accuracy to the patient fluid output readings by collecting any fluid that may have been aerosolized during wound or surgical drainage. In some embodiments, the system contains replaceable and/or disposable desiccant dehumidifiers which absorb the moisture from the air prior to being exhausted from the system. The desiccant dehumidifiers may be in any suitable location, such as but not limited to, within the controller/monitor, in the path of the air being exhausted by the system, such as the chest tube and/or drainage tube, or within the drainage canister.

Some embodiments of the chest drainage system include a mechanical positive pressure safety valve (PPSV) with integrated filtration, which prevents contaminants within the exhaled air from being expelled into the environment if pressure is vented through the mechanical PPSV instead of being pumped out of the system via the controller (for example, in the event that the controller is powered down). These embodiments may use the hospital's central suction system to remove exhaled air from the environment. This exhaled air may be filtered to reduce contamination. The filters may be replaceable/disposable. The filter may be made from a hydrophobic material. The filter may filter viruses and/or bacteria and/or other contaminants. The filter may be configured to filter viruses and/or particles larger than 0.001 μm.

Figure 63:
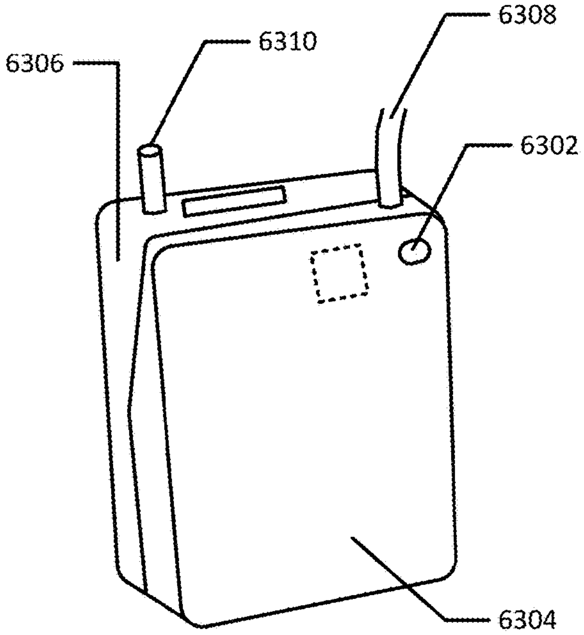
FIG. 63 shows an embodiment of the system designed for pathogen control.

FIG. 63 shows an embodiment of the system with positive pressure safety valve (PPSV) 6302, which is incorporated into canister 6304, and in communication with controller/monitor 6306. Also shown are drainage tube 6308 and output port 6310. The drainage tube receives drained fluids from the patient. The output port connects to hospital suction or any other suction source. A filter may be present in one or more of these components. Canister 6304 may be sealed, i.e. not in fluid communication with the atmosphere surrounding it.

Figure 64:
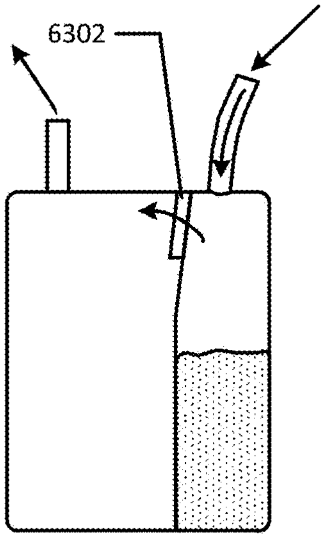
FIG. 64 shows a side view of the embodiment shown in FIG. 63.

FIG. 64 shows a side view of the embodiment shown in FIG. 63. The arrows indicate air flow through the system. Rather than air escaping canister 6304 via a vent, the external vacuum source of this embodiment pulls the collected air through the controller/monitor and forces it to exit via output port 6310.

Figure 65:
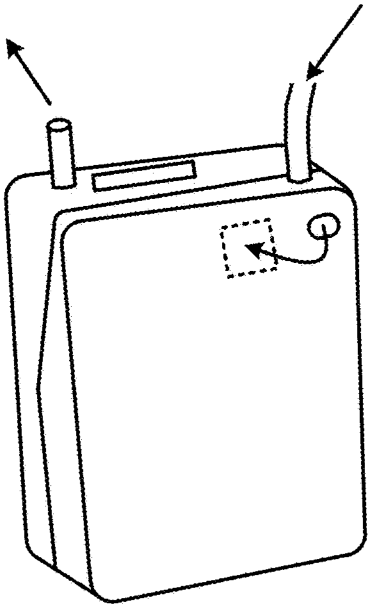
FIG. 65 shows the flow of air from the front view of the system shown in FIG. 63.

FIG. 65 shows the flow of air from the front view.

Figure 66:
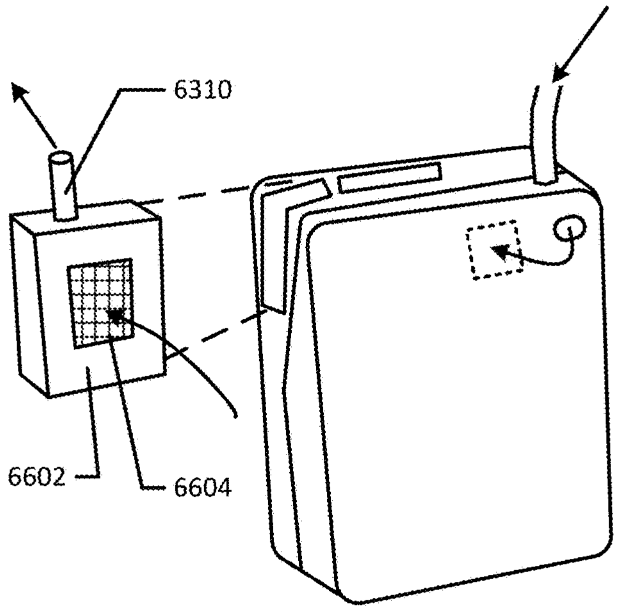

FIG. 66 shows an embodiment which includes sealed cartridge 6602 which is configured to capture virtually all the contaminants in the collected air. The cartridge may include filter 6604 and output port 6310.

The embodiments shown in FIGS. 64-66 allow for a stand-alone chest drain system that may utilize hospital wall suction to provide continuous removal of all expelled air from the patient.

Alternatively, the system may utilize an independent external suction source and the system may filter the collected air to prevent contaminants from entering the room.

Any air expelled from the internal suction pump (the pump which applies a negative pressure to the drainage line) may also be removed via output port 6310.

PPSV 6302 may include a valve with a crack pressure equal to, or less than, for example, 1 cmH20, 2 cmH2O, 5 cmH2O, or 10 cmH2O.

OTHER EMBODIMENTS

In some embodiments of the chest drainage system, the monitor provides pulsatile suction (whether via the valve device or via the pump in the monitor to maintain chest tube patency. This suction may be in the form of a sine wave, square wave, or any other suitable oscillatory waveform, and may oscillate between, for example but not limited to 0 to −40 cmH2O, 0 to −60 cmH2O, 0 to −80 cmH2O, 0 to −100 cmH2O, −10 to −40 cmH2O, −20 to −60 cmH2O, and so on. These embodiments may or may not include a chest tube relief lumen.

Some embodiments of the chest drainage system may include a fluid sample port to allow for easy access to draining fluids, for sampling, testing, etc. The port may include a luer-lock valve for the purposes of sampling. The sampling port may be anywhere in the system where drained or draining fluids may be accessed. For example, at the tube-tube junction, along the drainage tube, within the collection chamber, at connection point(s) along the system, etc. The system may provide intuitive, step-by-step sampling instructions via the controller display screen. These instructions may include how to properly clamp the drainage tubing, attach a syringe to the sampling port, and collect a fluid sample. The controller may be placed (or place itself) in standby mode during the sampling process, which may pause normal operation and hold the system in a safe state until the sample is collected.

Some embodiments of the chest drainage system may include an integrated drainage tubing clamp. This claim may slide along all or part of the length of the drainage tubing set and may be pre-installed.

Some embodiments of the chest drainage system may include a positive pressure relief valve. The drainage canister may include an overpressure valve designed to provide an outlet for positively pressurized air to escape the system, for example, when a patient coughs.

Some embodiments of the chest drainage system may include a canister plug for easy disposal of the drainage canister. For example, the drainage canister may have an integrated slot designed to hold a silicone rubber plug, which can be used to close off the drainage canister inlet port after use.

Some embodiments of the chest drainage system may include allow for the use of multiple drainage canisters per patient. Step-by-step instructions may be displayed on the monitor by the controller. These steps may include disconnecting the drainage tubing from the drainage canister, removing and disposing of the drainage canister, installing and attaching a new drainage canister, re-connecting the drainage tubing, etc. During this process, the controller may be placed, or place itself, in standby mode which pauses normal operation and holds the system in a safe state until the drainage canister is replaced.

Some embodiments of the chest drainage system may include physical graduations on the drainage canister, for example, graduation markings on the front face of the canister, ranging from 20-1200 ml in increments of 10 mL.

Some embodiments of the chest drainage system may include drainage canister overfill protection. In some embodiments, the drainage canister includes a filter membrane assembly which acts as a physical barrier to prevent fluid from entering the controller in the case of an overfilled drainage canister or if the system is tipped over. The "filter cage" may be a rigid structure that supports a filter membrane (for example but not limited to 0.2, 1.2, or 5 micron pore size) and is located inside the body of the drainage canister. In addition to the physical, filter membrane barrier in the drainage canister, the controller may utilize the built-in capacitive sensor to pre-emptively disable the pump from pulling fluid into the canister, and potentially into the pump of the controller/monitor, when the volume in the drainage canister reaches its capacity. This capacity may be sensed by the controller or preset by the user.

Some embodiments of the chest drainage system may automatically adjust the suction level based on a measured parameter, such as the air leak rate or drainage volume. In some embodiments, the controller may adjust the suction from, for example, −20 cmH2O when the patient has an air leak in excess of, for example, 500 mL/min, and then decrease the suction to a lower level, for example −8 cmH2O, when the air leak diminishes below, for example, 500 mL/min. A similar approach may be taken using drainage volume as the input parameter, whereby the suction level is higher as drainage volume output is higher and then decreases as the patient's drainage output diminishes. These techniques may depend on pre-defined thresholds at which the suction level is adjusted, or may be based on a continuous scale, whereby the suction level is adjusted continuously based on the air leak and/or drainage volume values.

Some embodiments of the chest drainage system may include a battery which allows the system to be portable. For example, the system may include a battery with a 4-hour battery life. Or, for example, the system may include a battery with a 1-hour battery life. Or, for example, the system may include a battery with a 2-hour battery life. Or, for example, the system may include a battery with a 3-hour battery life. Or, for example, the system may include a battery with a 5-hour battery life. Or, for example, the system may include a battery with a 24-hour battery life. Or, for example, the system may include a battery with a greater than 1-hour battery life.

Figure 35:
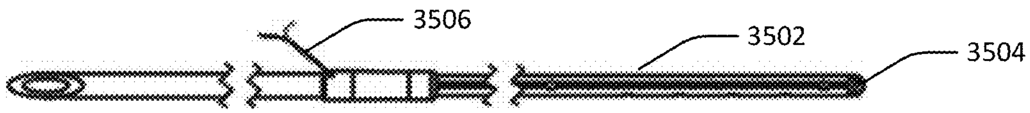
FIG. 35 shows an embodiment of the chest tube which includes sensors.

In some embodiments, the system possesses a body contacting, or non-body contacting, sensor system or biological component with a physicochemical detector incorporated into the chest tube (FIG. 35) in which the patient vital signs (e.g. heart rate, respiration rate, blood pressure, body temperature) and/or chemical signals (e.g. analysis of blood, pulmonary fluid) are transmitted to the controller, hospital monitoring systems, and/or other devices to share and display information to physicians, to receive information about the patient to be used for various action, or to send information about the patient to other devices for various actions. FIG. 35 shows chest tube 3502, sensors 3504 and sensor leads or wires 3506 which connect to the controller. The connection may alternatively be wireless.

Some embodiments of the system include Digital patient identification means including biometric methodologies.

Example of Data Processing System

Figure 36:
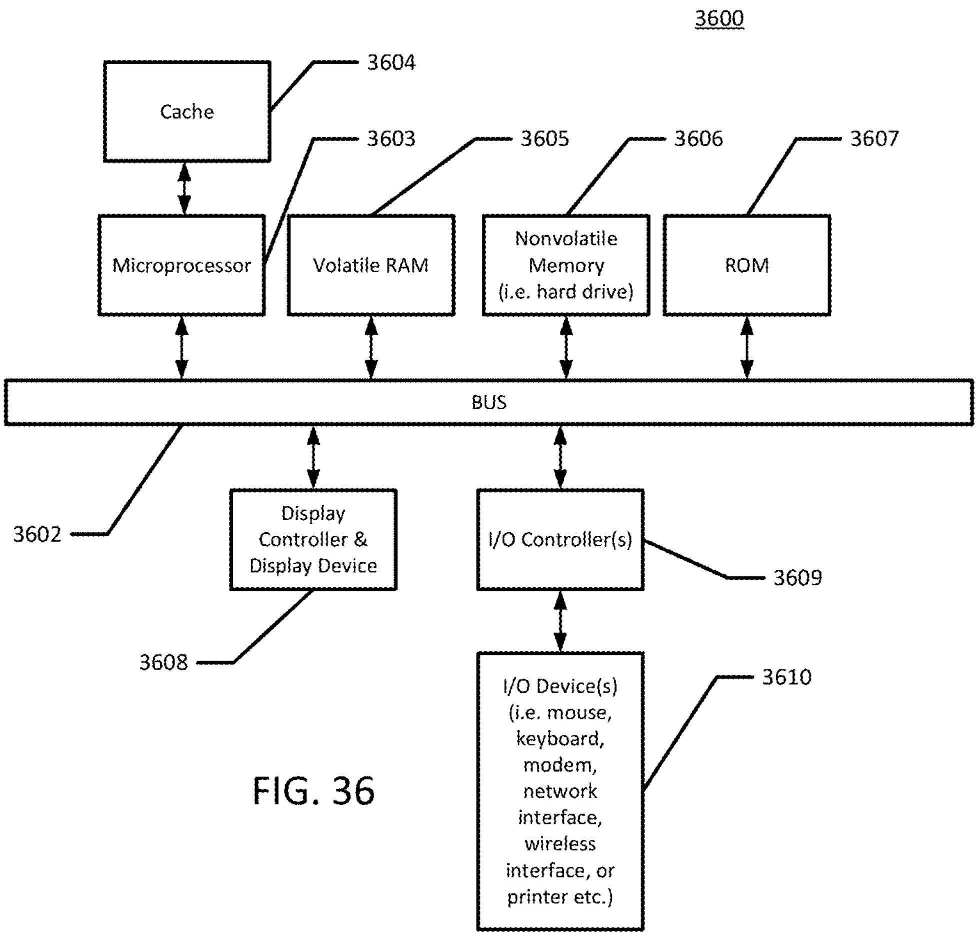
FIG. 36 is a block diagram of a data processing system.

FIG. 36 is a block diagram of a data processing system, which may be used with any embodiment of the invention. For example, the system 3600 may be used as part of a controller/monitor. Note that while FIG. 36 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 36, the computer system 3600, which is a form of a data processing system, includes a bus or interconnect 3602 which is coupled to one or more microprocessors 3603 and a ROM 3607, a volatile RAM 3605, and a non-volatile memory 3606. The microprocessor 3603 is coupled to cache memory 3604. The bus 3602 interconnects these various components together and also interconnects these components 3603, 3607, 3605, and 3606 to a display controller and display device 3608, as well as to input/output (I/O) devices 3610, which may be mice, keyboards, modems, network interfaces, printers, and other devices which are well-known in the art.

Typically, the input/output devices 3610 are coupled to the system through input/output controllers 3609. The volatile RAM 3605 is typically implemented as dynamic RAM (DRAM) which requires power continuously in order to refresh or maintain the data in the memory. The non-volatile memory 3606 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 36 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 3602 may include one or more buses connected to each other through various bridges, controllers, and/or adapters, as is well-known in the art. In one embodiment, the I/O controller 3609 includes a USB (Universal Serial Bus) adapter for controlling USB peripherals. Alternatively, I/O controller 3609 may include IEEE-1394 adapter, also known as FireWire adapter, for controlling FireWire devices, SPI (serial peripheral interface), I2C (inter-integrated circuit) or UART (universal asynchronous receiver/transmitter), or any other suitable technology.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

What is claimed is:

1. A drainage system, comprising:

a chest tube configured for insertion at least partially within a body of a subject;

a drainage tube fluidly coupled with the chest tube;

a reservoir fluidly coupled with the drainage tube;

a pump in communication with the reservoir;

a controller in communication with the reservoir, wherein the controller is configured to determine a readiness for removal of the chest tube from the body based upon removal parameters including a combination of a chest/thoracic air leak rate through the chest tube or drainage tube and a liquid drainage volume from the chest tube or drainage tube where the chest/thoracic air leak rate and the liquid drainage volume are each obtained over a period of time via the controller; and a display in communication with the controller, wherein the controller is further configured to provide a pleural assessment upon the display indicating a presence or lack of presence of pressure oscillations relating to breathing by the subject.

2. The system of claim 1 wherein the controller is further configured to provide an indication of the readiness for removal.

3. The system of claim 2 wherein the controller is further configured to provide the indication of the readiness for removal upon the display.

4. The system of claim 2 wherein the indication of the readiness for removal further comprises an indication of subject progress over the period of time.

5. The system of claim 2 wherein the indication of the readiness for removal further comprises an indication that the chest tube is ready for removal from the body.

6. The system of claim 2 wherein the indication of the readiness for removal further comprises an indication that the chest tube is not ready for removal from the body.

7. The system of claim 1 wherein the air leak rate is obtained over a 6 hour period of time.

8. The system of claim 1 wherein the air leak rate is obtained over a 8 hour period of time.

9. The system of claim 1 wherein the air leak rate is obtained over a 12 hour period of time.

10. The system of claim 1 wherein the air leak rate is obtained over a 24 hour period of time.

11. The system of claim 1 wherein the air leak rate is obtained over a 48 hour period of time.

12. The system of claim 1 wherein the removal parameters comprise a mean and/or median of the air leak rate over the period of time.

13. The system of claim 1 wherein the removal parameters comprise a maximum value of the air leak rate over the period of time.

14. The system of claim 1 wherein the liquid drainage volume is obtained over a 6 hour period of time.

15. The system of claim 1 wherein the liquid drainage volume is obtained over a 8 hour period of time.

16. The system of claim 1 wherein the liquid drainage volume is obtained over a 12 hour period of time.

17. The system of claim 1 wherein the liquid drainage volume is obtained over a 24 hour period of time.

18. The system of claim 1 wherein the liquid drainage volume is obtained over a 48 hour period of time.

19. The system of claim 1 wherein the removal parameters comprise an indication of patency of the chest tube based upon a confirmation of dynamic pressure within the system.

20. The system of claim 1 wherein the controller is further configured to compare the removal parameters against a threshold value in determining readiness for removal.

21. The system of claim 20 wherein the threshold value is stored within the controller.

22. The system of claim 21 wherein the threshold value is entered within the controller for storage via a user.

23. The system of claim 21 wherein the threshold value is selected within the controller via a user.

24. The system of claim 1 wherein the removal parameters are entered or selected within the controller via a user.

25. A method for removing a drainage system, comprising:

receiving a liquid from a body of a subject through a drainage tube and into a reservoir, where the drainage tube is fluidly coupled with a chest tube inserted at least partially within the body;

monitoring the drainage system via a controller for removal parameters including a combination of a chest/thoracic air leak rate through the chest tube or drainage tube and a liquid drainage volume from the chest tube or drainage tube where the chest/thoracic air leak rate and the liquid drainage volume are each obtained over a period of time;

determining a readiness for removal of the chest tube from the body via the controller based upon the removal parameters; and displaying a pleural assessment upon a display in communication with the controller where the pleural assessment indicates a presence or lack of presence of pressure oscillations relating to breathing by the subject.

26. The method of claim 25 further comprising providing an indication of the readiness for removal to a user.

27. The method of claim 26 wherein the controller is further configured to display the indication of the readiness for removal upon the display to the user.

28. The method of claim 26 further comprising indicating a progress of the subject over the period of time.

29. The method of claim 26 further comprising indicating that the chest tube is ready for removal from the body.

30. The method of claim 26 further comprising indicating that the chest tube is not ready for removal from the body.

31. The method of claim 25 wherein monitoring the drainage system comprises monitoring the air leak rate over a 6 hour period of time.

32. The method of claim 25 wherein monitoring the drainage system comprises monitoring the air leak rate over a 8 hour period of time.

33. The method of claim 25 wherein monitoring the drainage system comprises monitoring the air leak rate over a 12 hour period of time.

34. The method of claim 25 wherein monitoring the drainage system comprises monitoring the air leak rate over a 24 hour period of time.

35. The method of claim 25 wherein monitoring the drainage system comprises monitoring the air leak rate over a 48 hour period of time.

36. The method of claim 25 wherein monitoring the drainage system further comprises determining a mean and/or median of the air leak rate over the period of time.

37. The method of claim 25 wherein monitoring the drainage system further comprises determining a maximum value of the air leak rate over the period of time.

38. The method of claim 25 wherein monitoring the drainage system comprises monitoring the liquid drainage volume over a 6 hour period of time.

39. The method of claim 25 wherein monitoring the drainage system comprises monitoring the liquid drainage volume over a 24 hour period of time.

40. The method of claim 25 further comprising determining an indication of patency of the chest tube based upon a confirmation of dynamic pressure within the system.

41. The method of claim 25 further comprising comparing the removal parameters against a threshold value in determining readiness for removal.

42. The method of claim 41 wherein the threshold value is stored within the controller.

43. The method of claim 42 wherein the threshold value is entered within the controller for storage via a user.

44. The method of claim 42 wherein the threshold value is selected within the controller via a user.

45. The method of claim 25 further comprising receiving the removal parameters within the controller.

46. The method of claim 25 wherein receiving the fluid from the body comprises receiving the liquid within a reservoir fluidly coupled with the drainage tube.

* * * * *